US011364258B2

(12) United States Patent
Terek et al.

(10) Patent No.: US 11,364,258 B2
(45) Date of Patent: Jun. 21, 2022

(54) METHODS FOR TREATING CHONDROSARCOMA USING MICRORNA(MIR)

(71) Applicant: Rhode Island Hospital, Providence, RI (US)

(72) Inventors: Richard Terek, Providence, RI (US); Qian Chen, Barrington, RI (US); Xiaojuan Sun, Barrington, RI (US)

(73) Assignee: Rhode Island Hospital, Providence, RI (US)

( * ) Notice: Subject to any disclaimer, the term of this patent is extended or adjusted under 35 U.S.C. 154(b) by 303 days.

(21) Appl. No.: 16/082,222

(22) PCT Filed: Mar. 6, 2017

(86) PCT No.: PCT/US2017/020975
§ 371 (c)(1),
(2) Date: Sep. 4, 2018

(87) PCT Pub. No.: WO2017/152182
PCT Pub. Date: Sep. 8, 2017

(65) Prior Publication Data
US 2020/0289542 A1 Sep. 17, 2020

Related U.S. Application Data

(60) Provisional application No. 62/304,048, filed on Mar. 4, 2016.

(51) Int. Cl.
| | |
|---|---|
| *C12N 15/11* | (2006.01) |
| *A61K 31/7105* | (2006.01) |
| *A61K 9/51* | (2006.01) |
| *A61K 31/395* | (2006.01) |
| *C12N 15/113* | (2010.01) |
| *A61K 9/00* | (2006.01) |
| *A61K 45/06* | (2006.01) |

(52) U.S. Cl.
CPC ........ *A61K 31/7105* (2013.01); *A61K 9/5184* (2013.01); *A61K 31/395* (2013.01); *C12N 15/113* (2013.01); *A61K 9/0019* (2013.01); *A61K 45/06* (2013.01); *C12N 2310/113* (2013.01)

(58) Field of Classification Search
CPC ..... C12N 15/11; C12N 15/111; C12N 15/113; C12N 2310/141; A61K 31/7105
See application file for complete search history.

(56) References Cited

U.S. PATENT DOCUMENTS

| | | |
|---|---|---|
| 4,987,071 A | 1/1991 | Cech et al. |
| 5,093,246 A | 3/1992 | Cech et al. |
| 5,194,599 A | 3/1993 | Froehler et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,527,899 A | 6/1996 | Froehler |
| 5,539,082 A | 7/1996 | Nielsen et al. |
| 5,541,306 A | 7/1996 | Agrawal et al. |
| 5,550,111 A | 8/1996 | Suhadolnik et al. |
| 5,552,540 A | 9/1996 | Haralambidis |
| 5,563,253 A | 10/1996 | Agrawal et al. |
| 5,565,555 A | 10/1996 | Froehler et al. |
| 5,571,799 A | 11/1996 | Tkachuk et al. |
| 5,587,361 A | 12/1996 | Cook et al. |
| 5,587,469 A | 12/1996 | Cook et al. |
| 5,594,121 A | 1/1997 | Froehler et al. |
| 5,596,086 A | 1/1997 | Matteucci et al. |
| 5,596,091 A | 1/1997 | Switzer |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,645,985 A | 7/1997 | Froehler et al. |
| 5,646,269 A | 7/1997 | Matteucci et al. |
| 5,663,312 A | 9/1997 | Chaturvedula |
| 5,672,697 A | 9/1997 | Buhr et al. |
| 5,677,437 A | 10/1997 | Teng et al. |
| 5,677,439 A | 10/1997 | Weis et al. |

(Continued)

FOREIGN PATENT DOCUMENTS

| | | |
|---|---|---|
| WO | 2007/146511 A2 | 12/2007 |
| WO | 2015/139051 A2 | 9/2015 |

(Continued)

OTHER PUBLICATIONS

Galoian et al., Lost miRNA surveillance of Notch, IGFR pathway—road to sarcomagenesis, Tumor Biology, vol. 35, pp. 483-492. (Year: 2014).*
Li et al., MicroRNA-34a inhibits glioblastoma growth by targeting multiple oncogenes, Cancer Research, vol. 69, pp. 7569-7576. (Year: 2009).*
Yan et al., MicroRNA-34a inhibits the proliferation and metastasis of osteosarcoma cells both in vitro and in vivo, PLoS ONE, vol. 7(3):e33778, pp. 1-11. (Year: 2012).*
Sun et al., MicroRNA regulates vascular endothelial growth factor expression in chondrosarcoma cells, Clinical Orthopaedics and Related Research, vol. 473, pp. 907-913. (Year: 2015).*

(Continued)

*Primary Examiner* — Dana H Shin
(74) *Attorney, Agent, or Firm* — Mintz Levin Cohn Ferris Glovsky and Popeo, P.C.; Ingrid A. Beattie

(57) ABSTRACT

This invention is directed to, inter alia, compositions and methods for restoring normal microRNA (miR) expression in chondrosarcoma cells as well as methods for treating and diagnosing chondrosarcoma in individuals in need thereof.

9 Claims, 19 Drawing Sheets

Specification includes a Sequence Listing.

(56) References Cited

U.S. PATENT DOCUMENTS

| | | | |
|---|---|---|---|
| 5,681,941 | A | 10/1997 | Cook et al. |
| 5,714,331 | A | 2/1998 | Buchardt et al. |
| 5,719,262 | A | 2/1998 | Buchardt et al. |
| 5,721,218 | A | 2/1998 | Froehler |
| 5,763,588 | A | 6/1998 | Matteucci et al. |
| 5,792,608 | A | 8/1998 | Swaminathan et al. |
| 5,830,653 | A | 11/1998 | Froehler et al. |
| 5,849,902 | A | 12/1998 | Arrow et al. |
| 6,005,096 | A | 12/1999 | Matteucci et al. |
| 7,399,845 | B2 | 7/2008 | Seth et al. |
| 2002/0173478 | A1 | 11/2002 | Gewirtz |
| 2004/0018176 | A1 | 1/2004 | Tolentino et al. |
| 2004/0224389 | A1 | 11/2004 | Bellgrau et al. |
| 2011/0105583 | A1 | 5/2011 | Cleary et al. |
| 2012/0259001 | A1 | 10/2012 | Khvorova et al. |
| 2015/0258094 | A1 | 9/2015 | Chen et al. |
| 2015/0344883 | A1 | 12/2015 | Brown et al. |

FOREIGN PATENT DOCUMENTS

| | | |
|---|---|---|
| WO | 2016/081522 A1 | 5/2016 |
| WO | 2017/152182 A1 | 9/2017 |

OTHER PUBLICATIONS

Dong et al., MicroRNA-34b/c suppresses uveal melanoma cell proliferation and migration through multiple targets, Molecular Vision, vol. 18, pp. 537-546. (Year: 2012).*

Sun et al. miR-181a Targets RGS16 to Promote Chondrosarcoma Growth, Angiogenesis, and Metastasis. Mol Cancer Res (Sep. 1, 2015) vol. 13., No. 9, pp. 1347-1357, abstract, p. 1348, col. 2, para. 2, Fig. 2A-2B.

Yoshitaka et al. Analysis of MicroRNAs Expressions in Chondrosarcoma. J. Orthop. Res. (Dec. 2013), vol. 31, No. 12, pp. 1992-1998, abstract, p. 1997, col. 2, para. 2, Fig. 3A.

Aili et al. (Nov. 5, 2015) "Microma-10b Suppresses the Migration and Invasion of Chondrosarcoma Cells by Targeting Brain-Derived Neurotrophic Factor", Molecular Medicine Reports, 13(1):1441-446.

Jiang et al. (Nov. 23, 2015) "The Overexpression of Mir-30a Affects Cell Proliferation of Chondrosarcoma via Targeting Runx2", Tumor Biology, 37(5):15933-5940.

Hammann et al. (Jan. 30, 2009) "Length Variation of Helix III in a Hammerhead Ribozyme and Its Influence on Cleavage Activity", Antisense and Nucleic Acid Drug Development, 9(1):25-31.

Khurana et al. (May 23, 2005) "Placental Growth Factor Promotes Atherosclerotic Intimal Thickening and Macrophage Accumulation", Circulation, 111(21):12828-2836.

Krutzfeldt et al. (2005) "Silencing of MicroRNAs in Vivo with 'Antagomirs'", Nature, 438(7068):1685-689.

Kulshrestha et al. (Jun. 15, 2007) "Regulation of MicroRNA Expression", Cell Cycle, 6(12):1426-1431.

Leddy et al. (Jul. 29, 2014) "Chondrosarcoma of Bone", Cancer Treatment and Research, 162:117-130.

Lin et al. (2004) "Hypoxia Induces HIF-1α and VEGF Expression in Chondrosarcoma Cells and Chondrocytes", Journal of Orthopaedic Research, 22:1175-1181.

Liu et al. (Nov. 13, 2014) "CCL5 Promotes Vascular Endothelial Growth Factor Expression and Induces Angiogenesis by Down-Regulating Mir-199a In Human Chondrosarcoma Cells", Cancer Letters, 357(2):476-487.

Mak et al. (Nov. 11, 2014) "The Epigenetic Regulation of SOX9 By Mir-145 in Human Chondrosarcoma", Journal of Cellular Biochemistry, 116(1):37-44.

Nielsen et al. (Dec. 6, 1991) "Sequence-Selective Recognition of DNA by Strand Displacement with a Thymine-Substituted Polyamide", Science, 254(5037):1497-1500.

Qasem et al. (Jan. 2014) "Cartilage-Forming Tumors", Seminars in Diagnostic Pathology, 31(1):10-20.

Rossi (May 1, 1994) "Practical Ribozymes: Making Ribozymes Work in Cells", Current Biology, 4(5):469-471.

Rylova et al. (Mar. 2002) "The CLN3 Gene is a Novel Molecular Target for Cancer Drug Discovery", Cancer Research, 62(3):801-808.

Shim et al. (Oct. 1, 2001) "Inhibition of Angiopoietin-1 Expression in Tumor Cells by an Antisense RNA Approach Inhibited Xenograft Tumor Growth in Immunodeficient Mice", International Journal of Cancer, 94(1):6-15.

Smith et al. (Dec. 2004) "CXCR4 Regulates Growth of Both Primary and Metastatic Breast Cancer", Cancer Research, 64(23):8604-8612.

Stein et al. (Aug. 20, 1993) "Antisense Oligonucleotides as Therapeutic Agents—is the Bullet Really Magical?", Science, 261(5124):1004-1012.

Sun et al. (Jul. 2013) "CXCR4-Targeted Therapy Inhibits VEGF Expression and Chondrosarcoma Angiogenesis and Metastasis", Molecular Cancer Therapeutics, 12(7):1163-1170.

Sun et al. (Oct. 24, 2005) "IGF2 is Critical for Tumorigenesis by Synovial Sarcoma Oncoprotein SYT-SSX1", Oncogene, 25(7):1042-1052.

Susa et al. (Jun. 2009) "Alendronate Inhibits Growth of High-Grade Chondrosarcoma Cells", Anticancer Research, 29(6):1879-1888.

Taraboletti et al. (Nov. 1987) "Thrombospondin-Induced Tumor Cell Migration: Haptotaxis and Chemotaxis are Mediated by Different Molecular Domains", The Journal of Cell Biology, 105:2409-2415.

Wang et al. (Jun. 1995) "Hypoxia-Inducible Factor 1 is a Basic-Helix-Loop-Helix-PAS Heterodimer Regulated by Cellular O2 Tension", PNAS, 92(12):5510-5514.

Werner et al. (Jun. 25, 1995) "The Effect of Base Mismatches in the Substrate Recognition Helices of Hammerhead Ribozymes on Binding and Catalysis", Nucleic Acids Research, 23(12):2092-2096.

Brown, H. et al., "Biology of Bone Sarcomas and New Therapeutic Developments", Calcified Tissue International (2018) 102:174-195.

* cited by examiner

SEQUENCE LISTING

```
<160> NUMBER OF SEQ ID NOS: 201

<210> SEQ ID NO 1
<211> LENGTH: 22
<212> TYPE: RNA
<213> ORGANISM: Artificial Sequence
<220> FEATURE:
<223> OTHER INFORMATION: miR-199a-3p Mature

<400> SEQUENCE: 1
acaguagucu gcacauuggu ua                                          22

<210> SEQ ID NO 2
<211> LENGTH: 71
<212> TYPE: RNA
<213> ORGANISM: Artificial Sequence
<220> FEATURE:
<223> OTHER INFORMATION: miR-199a-3p Stem loop

<400> SEQUENCE: 2
gccaacccag uguucagacu accuguucag gaggcucuca auguguacag uagucugcac    60
auugguuagg c                                                       71

<210> SEQ ID NO 3
<211> LENGTH: 22
<212> TYPE: RNA
<213> ORGANISM: Artificial Sequence
<220> FEATURE:
<223> OTHER INFORMATION: miR-26a Mature

<400> SEQUENCE: 3
uucaaguaau ccaggauagg cu                                          22
```

```
<210> SEQ ID NO 4
<211> LENGTH: 77
<212> TYPE: RNA
<213> ORGANISM: Artificial Sequence
<220> FEATURE:
<223> OTHER INFORMATION: miR-26a Stem Loop

<400> SEQUENCE: 4
guggccucgu ucaaguaauc caggauaggc ugugcagguc ccaaugggcc uauucuuggu    60
uacuugcacg gggacgc                                                   77

<210> SEQ ID NO 5
<211> LENGTH: 22
<212> TYPE: RNA
<213> ORGANISM: Artificial Sequence
<220> FEATURE:
<223> OTHER INFORMATION: miR-762 Mature

<400> SEQUENCE: 5
ggggcugggg ccggggccga gc                                             22

<210> SEQ ID NO 6
<211> LENGTH: 83
<212> TYPE: RNA
<213> ORGANISM: Artificial Sequence
<220> FEATURE:
<223> OTHER INFORMATION: miR-762 Stem Loop

<400> SEQUENCE: 6
ggcccggcuc cgggucucgg cccguacagu ccggccggcc augcuggcgg ggcuggggcc    60
ggggccgagc ccgcggcggg gcc                                            83

<210> SEQ ID NO 7
<211> LENGTH: 24
<212> TYPE: RNA
<213> ORGANISM: Artificial Sequence
<220> FEATURE:
<223> OTHER INFORMATION: miR-125a-5p Mature

<400> SEQUENCE: 7
ucccugagac ccuuuaaccu guga                                           24

<210> SEQ ID NO 8
<211> LENGTH: 86
<212> TYPE: RNA
<213> ORGANISM: Artificial Sequence
<220> FEATURE:
<223> OTHER INFORMATION: miR-125a-5p Stem Loop

<400> SEQUENCE: 8
ugccagucuc uaggucccug agacccuuua accugugagg acauccaggg ucacaggugo    60 gguucuuggg agccuggcgu cuggcc                                         86

<210> SEQ ID NO 9
<211> LENGTH: 22
<212> TYPE: RNA
<213> ORGANISM: Artificial Sequence
<220> FEATURE:
<223> OTHER INFORMATION: miR-let-7G Mature

<400> SEQUENCE: 9
ugagguagua guuuguacag uu                                             22
```

```
<210> SEQ ID NO 10
<211> LENGTH: 84
<212> TYPE: RNA
<213> ORGANISM: Artificial Sequence
<220> FEATURE:
<223> OTHER INFORMATION: miR-let-7G Stem Loop

<400> SEQUENCE: 10
aggcugaggu aguaguuugu acaguuugag ggucuaugau accacccggu acaggagaua    60
acuguacagg ccacugccuu gcca                                          84

<210> SEQ ID NO 11
<211> LENGTH: 22
<212> TYPE: RNA
<213> ORGANISM: Artificial Sequence
<220> FEATURE:
<223> OTHER INFORMATION: miR-16 Mature

<400> SEQUENCE: 11
uagcagcacg uaaauauugg cg                                            22

<210> SEQ ID NO 12
<211> LENGTH: 89
<212> TYPE: RNA
<213> ORGANISM: Artificial Sequence
<220> FEATURE:
<223> OTHER INFORMATION: miR-16 Stem Loop

<400> SEQUENCE: 12
gucagcagug ccuuagcagc acguaaauau uggcguuaag auucuaaaau uaucuccagu    60
auuaacugug cugcugaagu aagguugac                                     89

<210> SEQ ID NO 13
<211> LENGTH: 22
<212> TYPE: RNA
<213> ORGANISM: Artificial Sequence
<220> FEATURE:
<223> OTHER INFORMATION: let-7f Mature

<400> SEQUENCE: 13
ugagguagua gauuguauag uu                                            22

<210> SEQ ID NO 14
<211> LENGTH: 87
<212> TYPE: RNA
<213> ORGANISM: Artificial Sequence
<220> FEATURE:
<223> OTHER INFORMATION: let-7f Stem Loop

<400> SEQUENCE: 14
ucagagugag guaguagauu guauaguugu ggguaguga uuuuacccug uucaggagau     60
aacuauacaa ucuauugccu ucccuga                                       87

<210> SEQ ID NO 15
<211> LENGTH: 22
<212> TYPE: RNA
<213> ORGANISM: Artificial Sequence
<220> FEATURE:
<223> OTHER INFORMATION: miR-21 Mature

<400> SEQUENCE: 15
uagcuuauca gacugauguu ga                                            22

<210> SEQ ID NO 16
```

```
<211> LENGTH: 72
<212> TYPE: RNA
<213> ORGANISM: Artificial Sequence
<220> FEATURE:
<223> OTHER INFORMATION: miR-21 Stem loop

<400> SEQUENCE: 16
ugucggguag cuuaucagac ugauguugac uguugaaucu cauggcaaca ccagucgaug    60
ggcugucuga ca                                                       72

<210> SEQ ID NO 17
<211> LENGTH: 22
<212> TYPE: RNA
<213> ORGANISM: Artificial Sequence
<220> FEATURE:
<223> OTHER INFORMATION: miR-Let-7a Mature

<400> SEQUENCE: 17
ugagguagua gguuguauag uu                                            22

<210> SEQ ID NO 18
<211> LENGTH: 80
<212> TYPE: RNA
<213> ORGANISM: Artificial Sequence
<220> FEATURE:
<223> OTHER INFORMATION: miR-Let-7a Stem Loop

<400> SEQUENCE: 18
ugggaugagg uaguagguug uauaguuuua gggucacacc caccacuggg agauaacuau    60
acaaucuacu gucuuuccua                                               80

<210> SEQ ID NO 19
<211> LENGTH: 25
<212> TYPE: RNA
<213> ORGANISM: Artificial Sequence
<220> FEATURE:
<223> OTHER INFORMATION: miR-638 Mature

<400> SEQUENCE: 19
agggaucgcg ggcggguggc ggccu                                         25

<210> SEQ ID NO 20
<211> LENGTH: 21
<212> TYPE: RNA
<213> ORGANISM: Artificial Sequence
<220> FEATURE:
<223> OTHER INFORMATION: miR-23a Mature

<400> SEQUENCE: 20
aucacauugc cagggauuuc c                                             21

<210> SEQ ID NO 21
<211> LENGTH: 73
<212> TYPE: RNA
<213> ORGANISM: Artificial Sequence
<220> FEATURE:
<223> OTHER INFORMATION: miR-23a Stem Loop

<400> SEQUENCE: 21
ggccggcugg gguuccuggg gaugggauuu gcuuccuguc acaaaucaca uugccaggga    60
uuuccaaccg acc                                                      73

<210> SEQ ID NO 22
<211> LENGTH: 22
```

```
<212> TYPE: RNA
<213> ORGANISM: Artificial Sequence
<220> FEATURE:
<223> OTHER INFORMATION: miR-92a Mature

<400> SEQUENCE: 22
uauugcacuu gucccggccu gu                                                  22

<210> SEQ ID NO 23
<211> LENGTH: 78
<212> TYPE: RNA
<213> ORGANISM: Artificial Sequence
<220> FEATURE:
<223> OTHER INFORMATION: miR-92a Stem Loop

<400> SEQUENCE: 23
cuuucuacac agguugggau cgguugcaau gcuguguuuc uguaugguau ugcacuuguc          60
ccggccuguu gaguuugg                                                       78

<210> SEQ ID NO 24
<211> LENGTH: 22
<212> TYPE: RNA
<213> ORGANISM: Artificial Sequence
<220> FEATURE:
<223> OTHER INFORMATION: miR-15b Mature

<400> SEQUENCE: 24
uagcagcaca ucaugguuua ca                                                  22

<210> SEQ ID NO 25
<211> LENGTH: 98
<212> TYPE: RNA
<213> ORGANISM: Artificial Sequence
<220> FEATURE:
<223> OTHER INFORMATION: miR-15b Stem Loop

<400> SEQUENCE: 25
uugaggccuu aaaguacugu agcagcacau caugguuuac augcuacagu caagaugcga          60
aucauuauuu gcugcucuag aaauuuaagg aaauucau                                 98

<210> SEQ ID NO 26
<211> LENGTH: 21
<212> TYPE: RNA
<213> ORGANISM: Artificial Sequence
<220> FEATURE:
<223> OTHER INFORMATION: miR-23b Mature

<400> SEQUENCE: 26
aucacauugc cagggauuac c                                                   21

<210> SEQ ID NO 27
<211> LENGTH: 97
<212> TYPE: RNA
<213> ORGANISM: Artificial Sequence
<220> FEATURE:
<223> OTHER INFORMATION: miR-23b Stem Loop

<400> SEQUENCE: 27
cucaggugcu cuggcugcuu ggguuccugg caugcugauu ugugacuuaa gauuaaaauc          60
acauugccag ggauuaccac gcaaccacga ccuuggc                                  97

<210> SEQ ID NO 28
<211> LENGTH: 22
<212> TYPE: RNA
```

```
<213> ORGANISM: Artificial Sequence
<220> FEATURE:
<223> OTHER INFORMATION: miR-451 Mature

<400> SEQUENCE: 28
aaaccguuac cauuacugag uu                                                    22

<210> SEQ ID NO 29
<211> LENGTH: 72
<212> TYPE: RNA
<213> ORGANISM: Artificial Sequence
<220> FEATURE:
<223> OTHER INFORMATION: miR-451 Stem Loop

<400> SEQUENCE: 29
cuugggaaug gcaaggaaac cguuaccauu acugaguuua guaaugguaa gguucucuu            60 gcuauaccca ga                                                               72

<210> SEQ ID NO 30
<211> LENGTH: 22
<212> TYPE: RNA
<213> ORGANISM: Artificial Sequence
<220> FEATURE:
<223> OTHER INFORMATION: miR-483-5P Mature

<400> SEQUENCE: 30
aagacgggag gaaagaaggg ag                                                    22

<210> SEQ ID NO 31
<211> LENGTH: 22
<212> TYPE: RNA
<213> ORGANISM: Artificial Sequence
<220> FEATURE:
<223> OTHER INFORMATION: miR-15a Mature

<400> SEQUENCE: 31
uagcagcaca uaaugguuug ug                                                    22

<210> SEQ ID NO 32
<211> LENGTH: 83
<212> TYPE: RNA
<213> ORGANISM: Artificial Sequence
<220> FEATURE:
<223> OTHER INFORMATION: miR-15a Stem Loop

<400> SEQUENCE: 32
ccuuggagua aaguagcagc acauaauggu uuguggauuu ugaaaaggug caggccauau           60
ugugcugccu caaaaauaca agg                                                   83

<210> SEQ ID NO 33
<211> LENGTH: 21
<212> TYPE: RNA
<213> ORGANISM: Artificial Sequence
<220> FEATURE:
<223> OTHER INFORMATION: miR-27a Mature

<400> SEQUENCE: 33
uucacagugg cuaaguuccg c                                                     21

<210> SEQ ID NO 34
<211> LENGTH: 78
<212> TYPE: RNA
<213> ORGANISM: Artificial Sequence
<220> FEATURE:
<223> OTHER INFORMATION: miR-27a Stem Loop
```

```
<400> SEQUENCE: 34
cugaggagca gggcuuagcu gcuugugagc agggucccaca ccaagucgug uucacagugg      60
cuaaguuccg ccccccag                                                    78

<210> SEQ ID NO 35
<211> LENGTH: 21
<212> TYPE: RNA
<213> ORGANISM: Artificial Sequence
<220> FEATURE:
<223> OTHER INFORMATION: miR-26b Mature

<400> SEQUENCE: 35
uucaaguaau ucaggauagg u                                                21

<210> SEQ ID NO 36
<211> LENGTH: 77
<212> TYPE: RNA
<213> ORGANISM: Artificial Sequence
<220> FEATURE:
<223> OTHER INFORMATION: miR-26b Stem Loop

<400> SEQUENCE: 36
ccgggaccca guucaaguaa uucaggauag guugugugcu guccagccug uucuccauua      60
cuuggcucgg ggaccgg                                                     77

<210> SEQ ID NO 37
<211> LENGTH: 22
<212> TYPE: RNA
<213> ORGANISM: Artificial Sequence
<220> FEATURE:
<223> OTHER INFORMATION: miR-let-7d Mature

<400> SEQUENCE: 37
agagguagua gguugcauag uu                                               22

<210> SEQ ID NO 38
<211> LENGTH: 87
<212> TYPE: RNA
<213> ORGANISM: Artificial Sequence
<220> FEATURE:
<223> OTHER INFORMATION: miR-let-7d Stem Loop

<400> SEQUENCE: 38
ccuaggaaga gguaguaggu ugcauaguuu uagggcaggg auuuugccca caaggaggua      60
acuauacgac cugcugccuu ucuuagg                                          87

<210> SEQ ID NO 39
<211> LENGTH: 21
<212> TYPE: RNA
<213> ORGANISM: Artificial Sequence
<220> FEATURE:
<223> OTHER INFORMATION: miR-27b Mature

<400> SEQUENCE: 39
uucacagugg cuaaguucug c                                                21

<210> SEQ ID NO 40
<211> LENGTH: 22
<212> TYPE: RNA
<213> ORGANISM: Artificial Sequence
<220> FEATURE:
<223> OTHER INFORMATION: miR-98 Mature
```

```
<400> SEQUENCE: 40
ugagguagua aguuguauug uu                                             22

<210> SEQ ID NO 41
<211> LENGTH: 119
<212> TYPE: RNA
<213> ORGANISM: Artificial Sequence
<220> FEATURE:
<223> OTHER INFORMATION: miR-98 Stem Loop

<400> SEQUENCE: 41
aggauucugc ucaugccagg gugagguagu aaguuguauu guuguggggu agggauauua    60
ggccccaauu agaagauaac uauacaacuu acuacuuucc cuggugugug gcauauuca    119

<210> SEQ ID NO 42
<211> LENGTH: 23
<212> TYPE: RNA
<213> ORGANISM: Artificial Sequence
<220> FEATURE:
<223> OTHER INFORMATION: miR-145 Mature

<400> SEQUENCE: 42
guccaguuuu cccaggaauc ccu                                            23

<210> SEQ ID NO 43
<211> LENGTH: 88
<212> TYPE: RNA
<213> ORGANISM: Artificial Sequence
<220> FEATURE:
<223> OTHER INFORMATION: miR-145 Stem Loop

<400> SEQUENCE: 43
caccuugucc ucacggucca guuucccag gaaucccuua gaugcuaaga ugggauucc     60 uggaaauacu guucuugagg ucaugguu                                       88

<210> SEQ ID NO 44
<211> LENGTH: 21
<212> TYPE: RNA
<213> ORGANISM: Artificial Sequence
<220> FEATURE:
<223> OTHER INFORMATION: miR-143 Mature

<400> SEQUENCE: 44
ugagaugaag cacuguagcu c                                              21

<210> SEQ ID NO 45
<211> LENGTH: 106
<212> TYPE: RNA
<213> ORGANISM: Artificial Sequence
<220> FEATURE:
<223> OTHER INFORMATION: miR-143 Stem Loop

<400> SEQUENCE: 45
gcgcagcgcc cugucuccca gccugaggug cagugcugca ucucuggguca guugggaguc   60 ugagaugaag cacuguagcu caggaagaga gaaguuguuc ugcagc                  106

<210> SEQ ID NO 46
<211> LENGTH: 20
<212> TYPE: RNA
<213> ORGANISM: Artificial Sequence
<220> FEATURE:
<223> OTHER INFORMATION: miR-1915 Mature

<400> SEQUENCE: 46
```

```
cccagggcg acgcggcggg                                                  20

<210> SEQ ID NO 47
<211> LENGTH: 80
<212> TYPE: RNA
<213> ORGANISM: Artificial Sequence
<220> FEATURE:
<223> OTHER INFORMATION: miR-1915 Stem Loop

<400> SEQUENCE: 47
ugagaggccg caccuugccu ugcugcccgg gccgugcacc cgugggcccc agggcgacgc      60 ggcggggcg gcccuagcga                                                  80

<210> SEQ ID NO 48
<211> LENGTH: 21
<212> TYPE: RNA
<213> ORGANISM: Artificial Sequence
<220> FEATURE:
<223> OTHER INFORMATION: mir-149* Mature

<400> SEQUENCE: 48
agggagggac gggggcugug c                                               21

<210> SEQ ID NO 49
<211> LENGTH: 89
<212> TYPE: RNA
<213> ORGANISM: Artificial Sequence
<220> FEATURE:
<223> OTHER INFORMATION: mir-149* Stem Loop

<400> SEQUENCE: 49
gccggcgccc gagcucuggc uccgugucuu cacucccgug cuuguccgag gagggaggga      60
gggacggggg cugugcuggg gcagcugga                                       89

<210> SEQ ID NO 50
<211> LENGTH: 22
<212> TYPE: RNA
<213> ORGANISM: Artificial Sequence
<220> FEATURE:
<223> OTHER INFORMATION: miR-7i Mature

<400> SEQUENCE: 50
ugagguagua guuugugcug uu                                              22

<210> SEQ ID NO 51
<211> LENGTH: 84
<212> TYPE: RNA
<213> ORGANISM: Artificial Sequence
<220> FEATURE:
<223> OTHER INFORMATION: miR-7i Stem Loop

<400> SEQUENCE: 51
cuggcugagg uaguaguuug ugcuguuggu cgguuguga cauugcccgc uguggagaua       60
acugcgcaag cuacugccuu gcua                                            84

<210> SEQ ID NO 52
<211> LENGTH: 22
<212> TYPE: RNA
<213> ORGANISM: Artificial Sequence
<220> FEATURE:
<223> OTHER INFORMATION: let-7c Mature

<400> SEQUENCE: 52
```

```
ugagguagua gguuguaugg uu                                              22

<210> SEQ ID NO 53
<211> LENGTH: 84
<212> TYPE: RNA
<213> ORGANISM: Artificial Sequence
<220> FEATURE:
<223> OTHER INFORMATION: let-7c Stem Loop

<400> SEQUENCE: 53
gcauccgggu ugagguagua gguuguaugg uuuagaguua cacccuggga guuaacugua     60
caaccuucua gcuuccuug gagc                                             84

<210> SEQ ID NO 54
<211> LENGTH: 22
<212> TYPE: RNA
<213> ORGANISM: Artificial Sequence
<220> FEATURE:
<223> OTHER INFORMATION: let-7e Mature

<400> SEQUENCE: 54
ugagguagga gguuguauag uu                                              22

<210> SEQ ID NO 55
<211> LENGTH: 79
<212> TYPE: RNA
<213> ORGANISM: Artificial Sequence
<220> FEATURE:
<223> OTHER INFORMATION: let-7e Stem Loop

<400> SEQUENCE: 55
cccgggcuga gguaggaggu uguauaguug aggaggacac ccaaggagau cacuauacgg     60
ccuccuagcu uuccccagg                                                  79

<210> SEQ ID NO 56
<211> LENGTH: 22
<212> TYPE: RNA
<213> ORGANISM: Artificial Sequence
<220> FEATURE:
<223> OTHER INFORMATION: miR-936 Mature

<400> SEQUENCE: 56
acaguagagg gaggaaucgc ag                                              22

<210> SEQ ID NO 57
<211> LENGTH: 98
<212> TYPE: RNA
<213> ORGANISM: Artificial Sequence
<220> FEATURE:
<223> OTHER INFORMATION: miR-936 Stem Loop

<400> SEQUENCE: 57
ucaaggccac uggacagua gagggaggaa ucgcagaaau cacuccagga gcaacugaga     60
gaccuugcuu cuacuuuacc agguccugcu ggcccaga                             98

<210> SEQ ID NO 58
<211> LENGTH: 22
<212> TYPE: RNA
<213> ORGANISM: Artificial Sequence
<220> FEATURE:
<223> OTHER INFORMATION: miR-let-7b Mature

<400> SEQUENCE: 58
ugagguagua gguugugugg uu                                              22
```

```
<210> SEQ ID NO 59
<211> LENGTH: 83
<212> TYPE: RNA
<213> ORGANISM: Artificial Sequence
<220> FEATURE:
<223> OTHER INFORMATION: miR-let-7b Stem Loop

<400> SEQUENCE: 59
cggggugagg uaguagguug ugugguuuca gggcagugau guugccccuc ggaagauaac      60
uauacaaccu acugccuucc cug                                             83

<210> SEQ ID NO 60
<211> LENGTH: 23
<212> TYPE: RNA
<213> ORGANISM: Artificial Sequence
<220> FEATURE:
<223> OTHER INFORMATION: miR-30c Mature

<400> SEQUENCE: 60
uguaaacauc cuacacucuc agc                                             23

<210> SEQ ID NO 61
<211> LENGTH: 72
<212> TYPE: RNA
<213> ORGANISM: Artificial Sequence
<220> FEATURE:
<223> OTHER INFORMATION: miR-30c Stem Loop

<400> SEQUENCE: 61
agauacugua aacauccuac acucucagcu guggaaagua agaaagcugg gagaaggcug      60
uuuacucuuu cu                                                         72

<210> SEQ ID NO 62
<211> LENGTH: 23
<212> TYPE: RNA
<213> ORGANISM: Artificial Sequence
<220> FEATURE:
<223> OTHER INFORMATION: miR-181d Mature

<400> SEQUENCE: 62
aacauucauu guugucggug ggu                                             23

<210> SEQ ID NO 63
<211> LENGTH: 137
<212> TYPE: RNA
<213> ORGANISM: Artificial Sequence
<220> FEATURE:
<223> OTHER INFORMATION: miR-181d Stem Loop

<400> SEQUENCE: 63
gucccucccc cuaggccaca gccgagguca caaucaacau ucauuguugu cggugggguug     60 ugaggacuga ggccagaccc accggggggau gaaugucacu guggcugggc cagacacggc   120
uuaaggggaa ugggggac                                                  137

<210> SEQ ID NO 64
<211> LENGTH: 22
<212> TYPE: RNA
<213> ORGANISM: Artificial Sequence
<220> FEATURE:
<223> OTHER INFORMATION: miR-148a Mature

<400> SEQUENCE: 64
```

```
ucagugcacu acagaacuuu gu                                              22
```

<210> SEQ ID NO 65
<211> LENGTH: 68
<212> TYPE: RNA
<213> ORGANISM: Artificial Sequence
<220> FEATURE:
<223> OTHER INFORMATION: miR-148a Stem Loop

<400> SEQUENCE: 65

```
gaggcaaagu ucugagacac uccgacucug aguaugauag aagucagugc acuacagaac     60
uuugucuc                                                              68
```

<210> SEQ ID NO 66
<211> LENGTH: 22
<212> TYPE: RNA
<213> ORGANISM: Artificial Sequence
<220> FEATURE:
<223> OTHER INFORMATION: miR-181c Mature

<400> SEQUENCE: 66

```
aacauucaac cugucgguga gu                                              22
```

<210> SEQ ID NO 67
<211> LENGTH: 109
<212> TYPE: RNA
<213> ORGANISM: Artificial Sequence
<220> FEATURE:
<223> OTHER INFORMATION: miR-181c Stem Loop

<400> SEQUENCE: 67

```
cggaaaauuu gccaaggguu uggggaaca uucaaccugu cggugaguuu gggcagcuca      60
ggcaaaccau cgaccguuga guggacccug aggccuggaa uugccaucu                 109
```

<210> SEQ ID NO 68
<211> LENGTH: 22
<212> TYPE: RNA
<213> ORGANISM: Artificial Sequence
<220> FEATURE:
<223> OTHER INFORMATION: miR-196a Mature

<400> SEQUENCE: 68

```
uagguaguuu cauguuguug gg                                              22
```

<210> SEQ ID NO 69
<211> LENGTH: 70
<212> TYPE: RNA
<213> ORGANISM: Artificial Sequence
<220> FEATURE:
<223> OTHER INFORMATION: miR-196a Stem Loop

<400> SEQUENCE: 69

```
gugaauuagg uaguuucaug uuguuggcc uggguuucug aacacaacaa cauuaaacca      60
cccgauucac                                                            70
```

<210> SEQ ID NO 70
<211> LENGTH: 22
<212> TYPE: RNA
<213> ORGANISM: Artificial Sequence
<220> FEATURE:
<223> OTHER INFORMATION: miR-30a Mature

<400> SEQUENCE: 70

```
uguaaacauc cucgacugga ag                                              22
```

<210> SEQ ID NO 71
<211> LENGTH: 71
<212> TYPE: RNA
<213> ORGANISM: Artificial Sequence
<220> FEATURE:
<223> OTHER INFORMATION: miR-30a Stem Loop

<400> SEQUENCE: 71
gcgacuguaa acauccucga cuggaagcug ugaagccaca gaugggcuuu cagucggaug    60
uuugcagcug c                                                        71

<210> SEQ ID NO 72
<211> LENGTH: 22
<212> TYPE: RNA
<213> ORGANISM: Artificial Sequence
<220> FEATURE:
<223> OTHER INFORMATION: miR-214 Mature

<400> SEQUENCE: 72
acagcaggca cagacaggca gu                                            22

<210> SEQ ID NO 73
<211> LENGTH: 109
<212> TYPE: RNA
<213> ORGANISM: Artificial Sequence
<220> FEATURE:
<223> OTHER INFORMATION: miR-214 Stem Loop

<400> SEQUENCE: 73
ggccuggcug gacagaguug ucaugugucu gccugucuac acuugcugug cagaacaucc    60
gcucaccugu acagcaggca cagacaggca gucacaugac aacccagcu               109

<210> SEQ ID NO 74
<211> LENGTH: 22
<212> TYPE: RNA
<213> ORGANISM: Artificial Sequence
<220> FEATURE:
<223> OTHER INFORMATION: miR-187* Mature

<400> SEQUENCE: 74
ggcuacaaca caggacccgg gc                                            22

<210> SEQ ID NO 75
<211> LENGTH: 109
<212> TYPE: RNA
<213> ORGANISM: Artificial Sequence
<220> FEATURE:
<223> OTHER INFORMATION: miR-187* Stem Loop

<400> SEQUENCE: 75
ggucgggcuc accaugacac agugugagac cucgggcuac aacacaggac ccgggcgcug    60
cucugacccc ucgugucuug uguugcagcc ggagggacgc aggccgca                109

<210> SEQ ID NO 76
<211> LENGTH: 22
<212> TYPE: RNA
<213> ORGANISM: Artificial Sequence
<220> FEATURE:
<223> OTHER INFORMATION: miR-663 Mture

<400> SEQUENCE: 76
aggcggggcg ccgcgggacc gc                                            22

<210> SEQ ID NO 77
<211> LENGTH: 93
<212> TYPE: RNA
<213> ORGANISM: Artificial Sequence
<220> FEATURE:
<223> OTHER INFORMATION: miR-663 Stem Loop

<400> SEQUENCE: 77
ccuuccggcg ucccaggcgg ggcgccgcgg gaccgcccuc gugucugugg cgguggauc    60 ccgcggccgu guuuuccugg uggcccggcc aug                                93

<210> SEQ ID NO 78
<211> LENGTH: 22
<212> TYPE: RNA
<213> ORGANISM: Artificial Sequence
<220> FEATURE:
<223> OTHER INFORMATION: miR-146a Mature

<400> SEQUENCE: 78
ugagaacuga auuccauggg uu                                            22

<210> SEQ ID NO 79
<211> LENGTH: 99
<212> TYPE: RNA
<213> ORGANISM: Artificial Sequence
<220> FEATURE:
<223> OTHER INFORMATION: miR-146a Stem Loop

<400> SEQUENCE: 79
ccgaugugua uccucagcuu ugagaacuga auuccauggg uugugucagu gucagaccuc    60
ugaaauucag uucuucagcu gggauaucuc ugucaucgu                          99

<210> SEQ ID NO 80
<211> LENGTH: 22
<212> TYPE: RNA
<213> ORGANISM: Artificial Sequence
<220> FEATURE:
<223> OTHER INFORMATION: miR-30d Mature

<400> SEQUENCE: 80
uguaaacauc cccgacugga ag                                            22

<210> SEQ ID NO 81
<211> LENGTH: 70
<212> TYPE: RNA
<213> ORGANISM: Artificial Sequence
<220> FEATURE:
<223> OTHER INFORMATION: miR-30d Stem Loop

<400> SEQUENCE: 81
guuguuguaa acaucccga cuggaagcug uaagacacag cuaagcuuuc agucagaugu    60
uugcugcuac                                                          70

<210> SEQ ID NO 82
<211> LENGTH: 22
<212> TYPE: RNA
<213> ORGANISM: Artificial Sequence
<220> FEATURE:
<223> OTHER INFORMATION: miR-365 Mature

<400> SEQUENCE: 82
uaaugccccu aaaaauccuu au                                            22

```
<210> SEQ ID NO 83
<211> LENGTH: 87
<212> TYPE: RNA
<213> ORGANISM: Artificial Sequence
<220> FEATURE:
<223> OTHER INFORMATION: miR-365 Stem Loop

<400> SEQUENCE: 83
accgcaggga aaaugaggga cuuuuggggg cagaugugguu ccauuccac uaucauaaug      60 ccccuaaaaa uccuuauugc ucuugca                                         87

<210> SEQ ID NO 84
<211> LENGTH: 22
<212> TYPE: RNA
<213> ORGANISM: Artificial Sequence
<220> FEATURE:
<223> OTHER INFORMATION: miR-424 Mature

<400> SEQUENCE: 84
cagcagcaau ucauguuuug aa                                              22

<210> SEQ ID NO 85
<211> LENGTH: 98
<212> TYPE: RNA
<213> ORGANISM: Artificial Sequence
<220> FEATURE:
<223> OTHER INFORMATION: miR-424 Stem Loop

<400> SEQUENCE: 85 cgagggaua cagcagcaau ucauguuuug aaguguucua aauggguucaa aacgugaggc      60 gcugcuauac ccccucgugg ggaagguaga aggugggg                             98

<210> SEQ ID NO 86
<211> LENGTH: 20
<212> TYPE: RNA
<213> ORGANISM: Artificial Sequence
<220> FEATURE:
<223> OTHER INFORMATION: miR-1231 Mature

<400> SEQUENCE: 86
gugucugggc ggacagcugc                                                 20

<210> SEQ ID NO 87
<211> LENGTH: 92
<212> TYPE: RNA
<213> ORGANISM: Artificial Sequence
<220> FEATURE:
<223> OTHER INFORMATION: miR-1231 Stem Loop

<400> SEQUENCE: 87
gucagugucu gggcggacag cugcaggaaa gggaagacca aggcuugcug ucugccagu      60 cugccacccu acccugucug uucuugccac ag                                   92

<210> SEQ ID NO 88
<211> LENGTH: 21
<212> TYPE: RNA
<213> ORGANISM: Artificial Sequence
<220> FEATURE:
<223> OTHER INFORMATION: miR-424* Mature

<400> SEQUENCE: 88
caaaacguga ggcgcugcua u                                               21

<210> SEQ ID NO 89
```

<211> LENGTH: 98
<212> TYPE: RNA
<213> ORGANISM: Artificial Sequence
<220> FEATURE:
<223> OTHER INFORMATION: miR-424* Stem Loop

<400> SEQUENCE: 89
cgaggggaua cagcagcaau ucauguuuug aaguguucua aaugguucaa aacgugaggc    60
gcugcuauac ccccucgugg ggaagguaga aggugggg                            98

<210> SEQ ID NO 90
<211> LENGTH: 23
<212> TYPE: RNA
<213> ORGANISM: Artificial Sequence
<220> FEATURE:
<223> OTHER INFORMATION: miR-454 Mature

<400> SEQUENCE: 90
uagugcaaua uugcuuauag ggu                                            23

<210> SEQ ID NO 91
<211> LENGTH: 115
<212> TYPE: RNA
<213> ORGANISM: Artificial Sequence
<220> FEATURE:
<223> OTHER INFORMATION: miR-454 Stem Loop

<400> SEQUENCE: 91
ucuguuuauc accagauccu agaacccuau caauauuguc ucugcugugu aaauaguucu    60
gaguagugca auauugcuua uagguuuug guguuuggaa agaacaaugg cagg          115

<210> SEQ ID NO 92
<211> LENGTH: 22
<212> TYPE: RNA
<213> ORGANISM: Artificial Sequence
<220> FEATURE:
<223> OTHER INFORMATION: miR-455-5p Mature

<400> SEQUENCE: 92
uaugugccuu uggacuacau cg                                             22

<210> SEQ ID NO 93
<211> LENGTH: 96
<212> TYPE: RNA
<213> ORGANISM: Artificial Sequence
<220> FEATURE:
<223> OTHER INFORMATION: miR-455-5p Stem Loop

<400> SEQUENCE: 93
ucccuggcgu gaggguaugu gccuuuggac uacaucgugg aagccagcac caugcagucc    60
augggcauau acacuugccu caaggccuau gucauc                              96

<210> SEQ ID NO 94
<211> LENGTH: 22
<212> TYPE: RNA
<213> ORGANISM: Artificial Sequence
<220> FEATURE:
<223> OTHER INFORMATION: miR-337-3p Mature

<400> SEQUENCE: 94
cuccuauaug augccuuucu uc                                             22

<210> SEQ ID NO 95
<211> LENGTH: 93

```
<212> TYPE: RNA
<213> ORGANISM: Artificial Sequence
<220> FEATURE:
<223> OTHER INFORMATION: miR-337-3p Stem Loop

<400> SEQUENCE: 95
guagucagua guuggggggu gggaacggcu ucauacagga guugaugcac aguuauccag      60
cuccuauaug augccuuucu ucauccccuu caa                                  93

<210> SEQ ID NO 96
<211> LENGTH: 22
<212> TYPE: RNA
<213> ORGANISM: Artificial Sequence
<220> FEATURE:
<223> OTHER INFORMATION: miR-381 Mature

<400> SEQUENCE: 96
uauacaaggg caagcucucu gu                                              22

<210> SEQ ID NO 97
<211> LENGTH: 75
<212> TYPE: RNA
<213> ORGANISM: Artificial Sequence
<220> FEATURE:
<223> OTHER INFORMATION: miR-381 Stem Loop

<400> SEQUENCE: 97
uacuuaaagc gagguugccc uuuguauauu cgguuuauug acuggaaua uacaagggca      60 agcucucugu gagua                                                      75

<210> SEQ ID NO 98
<211> LENGTH: 22
<212> TYPE: RNA
<213> ORGANISM: Artificial Sequence
<220> FEATURE:
<223> OTHER INFORMATION: miR-30e Mature

<400> SEQUENCE: 98
uguaaacauc cuugacugga ag                                              22

<210> SEQ ID NO 99
<211> LENGTH: 92
<212> TYPE: RNA
<213> ORGANISM: Artificial Sequence
<220> FEATURE:
<223> OTHER INFORMATION: miR-30e Stem Loop

<400> SEQUENCE: 99
gggcagucuu ugcuacugua aacauccuug acuggaagcu guaaggguuu cagaggagcu      60
uucagucgga uguuuacagc ggcaggcugc ca                                   92

<210> SEQ ID NO 100
<211> LENGTH: 23
<212> TYPE: RNA
<213> ORGANISM: Artificial Sequence
<220> FEATURE:
<223> OTHER INFORMATION: miR-181a Mature

<400> SEQUENCE: 100
aacauucaac gcugucggug agu                                             23

<210> SEQ ID NO 101
<211> LENGTH: 110
<212> TYPE: RNA
```

```
<213> ORGANISM: Artificial Sequence
<220> FEATURE:
<223> OTHER INFORMATION: miR-181a Stem Loop

<400> SEQUENCE: 101
agaagggcua ucaggccagc cuucagagga cuccaaggaa cauucaacgc ugucggugag     60
uuugggauuu gaaaaaacca cugaccguug acuguaccuu gggguccuua                110

<210> SEQ ID NO 102
<211> LENGTH: 100
<212> TYPE: RNA
<213> ORGANISM: Artificial Sequence
<220> FEATURE:
<223> OTHER INFORMATION: miR-638 Stem Loop

<400> SEQUENCE: 102
gugagcgggc gcggcaggga ucgcgggcgg guggcggccu agggcgcgga gggcggaccg     60
ggaauggcgc gccgugcgcc gccggcguaa cugcggcgcu                           100

<210> SEQ ID NO 103
<211> LENGTH: 76
<212> TYPE: RNA
<213> ORGANISM: Artificial Sequence
<220> FEATURE:
<223> OTHER INFORMATION: miR-483-5P Stem Loop

<400> SEQUENCE: 103 gaggggggaag acgggaggaa agaagggagu gguuccauca cgccuccuca cuccucuccu    60
cccgucuucu ccucuc                                                     76

<210> SEQ ID NO 104
<211> LENGTH: 20
<212> TYPE: RNA
<213> ORGANISM: Artificial Sequence
<220> FEATURE:
<223> OTHER INFORMATION: miR-320c Mature

<400> SEQUENCE: 104
aaaagcuggg uugagagggu                                                 20

<210> SEQ ID NO 105
<211> LENGTH: 22
<212> TYPE: RNA
<213> ORGANISM: Artificial Sequence
<220> FEATURE:
<223> OTHER INFORMATION: miR-320b Mature

<400> SEQUENCE: 105
aaaagcuggg uugagagggc aa                                              22

<210> SEQ ID NO 106
<211> LENGTH: 79
<212> TYPE: RNA
<213> ORGANISM: Artificial Sequence
<220> FEATURE:
<223> OTHER INFORMATION: miR-320b Stem Loop

<400> SEQUENCE: 106
aauuaauccc ucucuuucua guucuuccua gagugaggaa aagcuggguu gagagggcaa     60
acaaauuaac uaauuaauu                                                  79

<210> SEQ ID NO 107
<211> LENGTH: 22
```

```
<212> TYPE: RNA
<213> ORGANISM: Artificial Sequence
<220> FEATURE:
<223> OTHER INFORMATION: miR-320a Mature

<400> SEQUENCE: 107
aaaagcuggg uugagagggc ga                                             22

<210> SEQ ID NO 108
<211> LENGTH: 82
<212> TYPE: RNA
<213> ORGANISM: Artificial Sequence
<220> FEATURE:
<223> OTHER INFORMATION: miR-320a Stem Loop

<400> SEQUENCE: 108
gcuucgcucc ccuccgccuu cucuucccgg uucuucccgg agucgggaaa agcuggguug    60
agagggcgaa aaaggaugag gu                                             82

<210> SEQ ID NO 109
<211> LENGTH: 22
<212> TYPE: RNA
<213> ORGANISM: Artificial Sequence
<220> FEATURE:
<223> OTHER INFORMATION: miR-127-3p Mature

<400> SEQUENCE: 109
ucggauccgu cugagcuugg cu                                             22

<210> SEQ ID NO 110
<211> LENGTH: 97
<212> TYPE: RNA
<213> ORGANISM: Artificial Sequence
<220> FEATURE:
<223> OTHER INFORMATION: miR-127-3p Stem Loop

<400> SEQUENCE: 110
ugugaucacu gucuccagcc ugcugaagcu cagagggcuc ugauucagaa agaucaucgg    60
auccgucuga gcuuggcugg ucggaagucu caucauc                             97

<210> SEQ ID NO 111
<211> LENGTH: 18
<212> TYPE: RNA
<213> ORGANISM: Artificial Sequence
<220> FEATURE:
<223> OTHER INFORMATION: miR-1260 Mature

<400> SEQUENCE: 111
aucccaccuc ugccacca                                                  18

<210> SEQ ID NO 112
<211> LENGTH: 73
<212> TYPE: RNA
<213> ORGANISM: Artificial Sequence
<220> FEATURE:
<223> OTHER INFORMATION: miR-1260 Stem Loop

<400> SEQUENCE: 112
accuuuccag cucaucccac cucugccacc aaaacacuca ucgcggguc agagggagug     60 ccaaaaaagg uaa                                                       73

<210> SEQ ID NO 113
<211> LENGTH: 21
<212> TYPE: RNA
```

```
<213> ORGANISM: Artificial Sequence
<220> FEATURE:
<223> OTHER INFORMATION: miR-140-3p Mature

<400> SEQUENCE: 113
uaccacaggg uagaaccacg g                                               21

<210> SEQ ID NO 114
<211> LENGTH: 100
<212> TYPE: RNA
<213> ORGANISM: Artificial Sequence
<220> FEATURE:
<223> OTHER INFORMATION: miR-140-3p Stem Loop

<400> SEQUENCE: 114
ugugucucuc ucuguguccu gccagugguu uuacccuaug guagguuacg ucaugcuguu     60
cuaccacagg guagaaccac ggacaggaua ccggggcacc                          100

<210> SEQ ID NO 115
<211> LENGTH: 22
<212> TYPE: RNA
<213> ORGANISM: Artificial Sequence
<220> FEATURE:
<223> OTHER INFORMATION: miR-22 Mature

<400> SEQUENCE: 115
aagcugccag uugaagaacu gu                                              22

<210> SEQ ID NO 116
<211> LENGTH: 85
<212> TYPE: RNA
<213> ORGANISM: Artificial Sequence
<220> FEATURE:
<223> OTHER INFORMATION: miR-22 Stem Loop

<400> SEQUENCE: 116
ggcugagccg caguaguucu ucagugggcaa gcuuuauguc cugacccagc uaaagcugcc    60
aguugaagaa cuguugcccu cugcc                                           85

<210> SEQ ID NO 117
<211> LENGTH: 22
<212> TYPE: RNA
<213> ORGANISM: Artificial Sequence
<220> FEATURE:
<223> OTHER INFORMATION: miR-146b-5p Mature

<400> SEQUENCE: 117
ugagaacuga auuccauagg cu                                              22

<210> SEQ ID NO 118
<211> LENGTH: 73
<212> TYPE: RNA
<213> ORGANISM: Artificial Sequence
<220> FEATURE:
<223> OTHER INFORMATION: miR-146b-5p Stem Loop

<400> SEQUENCE: 118
ccuggcacug agaacugaau uccauaggcu gugagcucua gcaaugcccu guggacucag     60
uucuggugcc cgg                                                        73

<210> SEQ ID NO 119
<211> LENGTH: 23
<212> TYPE: RNA
<213> ORGANISM: Artificial Sequence
```

```
<220> FEATURE:
<223> OTHER INFORMATION: miR-107 Mature

<400> SEQUENCE: 119
agcagcauug uacagggcua uca                                            23

<210> SEQ ID NO 120
<211> LENGTH: 81
<212> TYPE: RNA
<213> ORGANISM: Artificial Sequence
<220> FEATURE:
<223> OTHER INFORMATION: miR-107 Stem Loop

<400> SEQUENCE: 120
cucucugcuu ucagcuucuu uacaguguug ccuuguggca uggaguucaa gcagcauugu    60
acagggcuau caaagcacag a                                              81

<210> SEQ ID NO 121
<211> LENGTH: 19
<212> TYPE: RNA
<213> ORGANISM: Artificial Sequence
<220> FEATURE:
<223> OTHER INFORMATION: miR-320d Mature

<400> SEQUENCE: 121
aaaagcuggg uugagagga                                                 19

<210> SEQ ID NO 122
<211> LENGTH: 48
<212> TYPE: RNA
<213> ORGANISM: Artificial Sequence
<220> FEATURE:
<223> OTHER INFORMATION: miR-320d Stem Loop

<400> SEQUENCE: 122
uucucguccc aguucuuccc aaaguugaga aaagcugggu ugagagga                 48

<210> SEQ ID NO 123
<211> LENGTH: 23
<212> TYPE: RNA
<213> ORGANISM: Artificial Sequence
<220> FEATURE:
<223> OTHER INFORMATION: miR-423-5p Mature

<400> SEQUENCE: 123
ugaggggcag agagcgagac uuu                                            23

<210> SEQ ID NO 124
<211> LENGTH: 94
<212> TYPE: RNA
<213> ORGANISM: Artificial Sequence
<220> FEATURE:
<223> OTHER INFORMATION: miR-423-5p Stem Loop

<400> SEQUENCE: 124
auaaaggaag uuaggcugag gggcagagag cgagacuuuu cuauuuucca aaagcucggu    60
cugaggcccc ucagucuugc uuccuaaccc gcgc                                94

<210> SEQ ID NO 125
<211> LENGTH: 23
<212> TYPE: RNA
<213> ORGANISM: Artificial Sequence
<220> FEATURE:
<223> OTHER INFORMATION: miR-1974 Mature
```

```
<400> SEQUENCE: 125
ugguuguagu ccgugcgaga aua                                              23

<210> SEQ ID NO 126
<211> LENGTH: 70
<212> TYPE: RNA
<213> ORGANISM: Artificial Sequence
<220> FEATURE:
<223> OTHER INFORMATION: miR-1974 Stem Loop

<400> SEQUENCE: 126
uguucuugua guugaaauac aacgaugguu uuucauauca uggucgugg uuguagaccg        60 ugcgagaaua                                                             70

<210> SEQ ID NO 127
<211> LENGTH: 21
<212> TYPE: RNA
<213> ORGANISM: Artificial Sequence
<220> FEATURE:
<223> OTHER INFORMATION: miR-455-3p Mature

<400> SEQUENCE: 127
gcaguccaug ggcauauaca c                                                21

<210> SEQ ID NO 128
<211> LENGTH: 96
<212> TYPE: RNA
<213> ORGANISM: Artificial Sequence
<220> FEATURE:
<223> OTHER INFORMATION: miR-455-3p Stem Loop

<400> SEQUENCE: 128
ucccuggcgu gaggguaugu gccuuuggac uacaucgugg aagccagcac caugcaguacc     60 augggcauau acacuugccu caaggccuau gucauc                                96

<210> SEQ ID NO 129
<211> LENGTH: 22
<212> TYPE: RNA
<213> ORGANISM: Artificial Sequence
<220> FEATURE:
<223> OTHER INFORMATION: miR-193b* Mature

<400> SEQUENCE: 129
aacuggcccu caaaguccccg cu                                              22

<210> SEQ ID NO 130
<211> LENGTH: 83
<212> TYPE: RNA
<213> ORGANISM: Artificial Sequence
<220> FEATURE:
<223> OTHER INFORMATION: miR-193b* Stem Loop

<400> SEQUENCE: 130 gugggucucag aaucggggguu uugagggcga gaugaguuua guuuuauucc aacuggcccu    60 caaaguccccg cuuuuggggu cau                                             83

<210> SEQ ID NO 131
<211> LENGTH: 23
<212> TYPE: RNA
<213> ORGANISM: Artificial Sequence
<220> FEATURE:
<223> OTHER INFORMATION: miR-103 Mature

<400> SEQUENCE: 131
```

```
agcagcauug uacagggcua uga                                              23

<210> SEQ ID NO 132
<211> LENGTH: 77
<212> TYPE: RNA
<213> ORGANISM: Artificial Sequence
<220> FEATURE:
<223> OTHER INFORMATION: miR-103 Stem Loop

<400> SEQUENCE: 132
uugugcuuuc agcuucuuua cagugcugcc uuguagcauu caggucaagc agcuuguaca      60
gggcuaugaa agaacca                                                    77

<210> SEQ ID NO 133
<211> LENGTH: 23
<212> TYPE: RNA
<213> ORGANISM: Artificial Sequence
<220> FEATURE:
<223> OTHER INFORMATION: miR-432 Matuer

<400> SEQUENCE: 133
ucuuggagua ggucauuggg ugg                                              23

<210> SEQ ID NO 134
<211> LENGTH: 94
<212> TYPE: RNA
<213> ORGANISM: Artificial Sequence
<220> FEATURE:
<223> OTHER INFORMATION: miR-432 Stem Loop

<400> SEQUENCE: 134
ugacuccucc aggucuugga guaggucauu ggguggaucc ucuauuuccu uacgugggcc      60
acuggauggc uccuccaugu cuuggaguag auca                                  94

<210> SEQ ID NO 135
<211> LENGTH: 21
<212> TYPE: RNA
<213> ORGANISM: Artificial Sequence
<220> FEATURE:
<223> OTHER INFORMATION: miR-151-3p Mature

<400> SEQUENCE: 135
cuagacugaa gcuccuugag g                                                21

<210> SEQ ID NO 136
<211> LENGTH: 90
<212> TYPE: RNA
<213> ORGANISM: Artificial Sequence
<220> FEATURE:
<223> OTHER INFORMATION: miR-151-3p Stem Loop

<400> SEQUENCE: 136
uuuccugccc ucgaggagcu cacagucuag uaugucucau ccccuacuag acugaagcuc      60
cuugaggaca gggaugguca uacucaccuc                                       90

<210> SEQ ID NO 137
<211> LENGTH: 21
<212> TYPE: RNA
<213> ORGANISM: Artificial Sequence
<220> FEATURE:
<223> OTHER INFORMATION: miR-31 Matre

<400> SEQUENCE: 137
```

|   |   |
|---|---|
| aggcaagaug cuggcauagc u | 21 |

<210> SEQ ID NO 138
<211> LENGTH: 71
<212> TYPE: RNA
<213> ORGANISM: Artificial Sequence
<220> FEATURE:
<223> OTHER INFORMATION: miR-31 Stem Loop

<400> SEQUENCE: 138

|   |   |
|---|---|
| ggagaggagg caagaugcug gcauagcugu ugaacuggga accugcuaug ccaacauauu | 60 |
| gccaucuuuc c | 71 |

<210> SEQ ID NO 139
<211> LENGTH: 24
<212> TYPE: RNA
<213> ORGANISM: Artificial Sequence
<220> FEATURE:
<223> OTHER INFORMATION: miR-664* Mature

<400> SEQUENCE: 139

|   |   |
|---|---|
| acuggcuagg gaaaaugauu ggau | 24 |

<210> SEQ ID NO 140
<211> LENGTH: 82
<212> TYPE: RNA
<213> ORGANISM: Artificial Sequence
<220> FEATURE:
<223> OTHER INFORMATION: miR-664* Stem Loop

<400> SEQUENCE: 140

|   |   |
|---|---|
| gaacauugaa acuggcuagg gaaaaugauu ggauagaaac uauuauucua uucauuuauc | 60 |
| cccagccuac aaaaugaaaa aa | 82 |

<210> SEQ ID NO 141
<211> LENGTH: 22
<212> TYPE: RNA
<213> ORGANISM: Artificial Sequence
<220> FEATURE:
<223> OTHER INFORMATION: miR-486-5p Mature

<400> SEQUENCE: 141

|   |   |
|---|---|
| uccuguacug agcugccccg ag | 22 |

<210> SEQ ID NO 142
<211> LENGTH: 68
<212> TYPE: RNA
<213> ORGANISM: Artificial Sequence
<220> FEATURE:
<223> OTHER INFORMATION: miR-486-5p Stem Loop

<400> SEQUENCE: 142

|   |   |
|---|---|
| gcauccugua cugagcugcc ccgaggcccu ucaugcugcc cagcucgggg cagcucagua | 60 |
| caggauac | 68 |

<210> SEQ ID NO 143
<211> LENGTH: 22
<212> TYPE: RNA
<213> ORGANISM: Artificial Sequence
<220> FEATURE:
<223> OTHER INFORMATION: miR-99a Mature

<400> SEQUENCE: 143

|   |   |
|---|---|
| aacccguaga uccgaucuug ug | 22 |

```
<210> SEQ ID NO 144
<211> LENGTH: 81
<212> TYPE: RNA
<213> ORGANISM: Artificial Sequence
<220> FEATURE:
<223> OTHER INFORMATION: miR-99a Stem Loop

<400> SEQUENCE: 144
cccauuggca uaaacccgua gauccgaucu uguggugaag uggaccgcac aagcucgcuu      60
cuaugggucu gugucagugu g                                                81

<210> SEQ ID NO 145
<211> LENGTH: 22
<212> TYPE: RNA
<213> ORGANISM: Artificial Sequence
<220> FEATURE:
<223> OTHER INFORMATION: miR-24 Mature

<400> SEQUENCE: 145
uggcucaguu cagcaggaac ag                                               22

<210> SEQ ID NO 146
<211> LENGTH: 68
<212> TYPE: RNA
<213> ORGANISM: Artificial Sequence
<220> FEATURE:
<223> OTHER INFORMATION: miR-24 Stem Loop

<400> SEQUENCE: 146
cuccggugcc uacugagcug auaucaguuc ucauuuuaca cacuggcuca guucagcagg      60
aacaggag                                                              68

<210> SEQ ID NO 147
<211> LENGTH: 23
<212> TYPE: RNA
<213> ORGANISM: Artificial Sequence
<220> FEATURE:
<223> OTHER INFORMATION: miR-191 Mature

<400> SEQUENCE: 147
caacggaauc ccaaaagcag cug                                              23

<210> SEQ ID NO 148
<211> LENGTH: 92
<212> TYPE: RNA
<213> ORGANISM: Artificial Sequence
<220> FEATURE:
<223> OTHER INFORMATION: miR-191 Stem Loop

<400> SEQUENCE: 148
cggcuggaca gcgggcaacg gaaucccaaa agcagcuguu gucuccagag cauuccagcu      60
gcgcuuggau uucguccccu gcucuccugc cu                                    92

<210> SEQ ID NO 149
<211> LENGTH: 22
<212> TYPE: RNA
<213> ORGANISM: Artificial Sequence
<220> FEATURE:
<223> OTHER INFORMATION: miR-99b Mature

<400> SEQUENCE: 149
cacccguaga accgaccuug cg                                               22
```

```
<210> SEQ ID NO 150
<211> LENGTH: 70
<212> TYPE: RNA
<213> ORGANISM: Artificial Sequence
<220> FEATURE:
<223> OTHER INFORMATION: miR-99b Stem Loop

<400> SEQUENCE: 150
ggcacccacc cguagaaccg accuugcggg gccuucgccg cacacaagcu cgugucugug    60
gguccguguc                                                          70

<210> SEQ ID NO 151
<211> LENGTH: 23
<212> TYPE: RNA
<213> ORGANISM: Artificial Sequence
<220> FEATURE:
<223> OTHER INFORMATION: miR-574-5p Mature

<400> SEQUENCE: 151
ugagugugug ugugagaugug ugu                                          23

<210> SEQ ID NO 152
<211> LENGTH: 96
<212> TYPE: RNA
<213> ORGANISM: Artificial Sequence
<220> FEATURE:
<223> OTHER INFORMATION: miR-574-5p Stem Loop

<400> SEQUENCE: 152
gggaccugcg ugggugcggg cgugugagug ugugugugug agugugoguc gcuccggguc    60 cacgcucaug cacacaccca cacgcccaca cucagg                             96

<210> SEQ ID NO 153
<211> LENGTH: 21
<212> TYPE: RNA
<213> ORGANISM: Artificial Sequence
<220> FEATURE:
<223> OTHER INFORMATION: miR-151-5p Mature

<400> SEQUENCE: 153
ucgaggagcu cacagucuag u                                             21

<210> SEQ ID NO 154
<211> LENGTH: 90
<212> TYPE: RNA
<213> ORGANISM: Artificial Sequence
<220> FEATURE:
<223> OTHER INFORMATION: miR-151-5p Stem Loop

<400> SEQUENCE: 154
uuuccugccc ucgaggagcu cacagucuag uaugucucau ccccuacuag acugaagcuc    60
cuugaggaca gggauggauca uacucaccuc                                   90

<210> SEQ ID NO 155
<211> LENGTH: 22
<212> TYPE: RNA
<213> ORGANISM: Artificial Sequence
<220> FEATURE:
<223> OTHER INFORMATION: miR-193a-5p Mature

<400> SEQUENCE: 155
ugggucuuug cgggcgagau ga                                            22
```

```
<210> SEQ ID NO 156
<211> LENGTH: 88
<212> TYPE: RNA
<213> ORGANISM: Artificial Sequence
<220> FEATURE:
<223> OTHER INFORMATION: miR-193a-5p Stem Loop

<400> SEQUENCE: 156
cgaggauggg agcugagggc ugggucuuug cgggcgagau gagggugucg gaucaacugg    60
ccuacaaagu cccaguucuc ggcccccg                                       88

<210> SEQ ID NO 157
<211> LENGTH: 19
<212> TYPE: RNA
<213> ORGANISM: Artificial Sequence
<220> FEATURE:
<223> OTHER INFORMATION: miR-1246 Mature

<400> SEQUENCE: 157
aauggauuuu uggagcagg                                                 19

<210> SEQ ID NO 158
<211> LENGTH: 73
<212> TYPE: RNA
<213> ORGANISM: Artificial Sequence
<220> FEATURE:
<223> OTHER INFORMATION: miR-1246 Stem Loop

<400> SEQUENCE: 158
uguauccuug aauggauuuu uggagcagga guggacaccu gacccaaagg aaaucaaucc    60
auaggcuagc aau                                                       73

<210> SEQ ID NO 159
<211> LENGTH: 20
<212> TYPE: RNA
<213> ORGANISM: Artificial Sequence
<220> FEATURE:
<223> OTHER INFORMATION: miR-877 Mature

<400> SEQUENCE: 159
guagaggaga uggcgcaggg                                                20

<210> SEQ ID NO 160
<211> LENGTH: 86
<212> TYPE: RNA
<213> ORGANISM: Artificial Sequence
<220> FEATURE:
<223> OTHER INFORMATION: miR-877 Stem Loop

<400> SEQUENCE: 160
guagaggaga uggcgcaggg gacacgggca aagacuuggg gguuccuggg acccucagac    60 gugguccuc uucucccucc ucccag                                          86

<210> SEQ ID NO 161
<211> LENGTH: 21
<212> TYPE: RNA
<213> ORGANISM: Artificial Sequence
<220> FEATURE:
<223> OTHER INFORMATION: miR-940 Mature

<400> SEQUENCE: 161
aaggcagggc ccccgcuccc c                                              21

<210> SEQ ID NO 162
```

```
<211> LENGTH: 94
<212> TYPE: RNA
<213> ORGANISM: Artificial Sequence
<220> FEATURE:
<223> OTHER INFORMATION: miR-940 Stem Loop

<400> SEQUENCE: 162
gugaggugug ggcccggccc caggagcggg gccugggcag ccccgugugu ugaggaagga    60
aggcagggcc cccgcucccc gggccugacc ccac                               94

<210> SEQ ID NO 163
<211> LENGTH: 17
<212> TYPE: RNA
<213> ORGANISM: Artificial Sequence
<220> FEATURE:
<223> OTHER INFORMATION: miR-1281 Mature

<400> SEQUENCE: 163
ucgccuccuc cucuccc                                                  17

<210> SEQ ID NO 164
<211> LENGTH: 54
<212> TYPE: RNA
<213> ORGANISM: Artificial Sequence
<220> FEATURE:
<223> OTHER INFORMATION: miR-1281 Stem Loop

<400> SEQUENCE: 164 aggggggcacc gggaggaggu gagugucucu gucgccucc uccucuccccc ccuu         54

<210> SEQ ID NO 165
<211> LENGTH: 22
<212> TYPE: RNA
<213> ORGANISM: Artificial Sequence
<220> FEATURE:
<223> OTHER INFORMATION: miR-494 Mature

<400> SEQUENCE: 165
ugaaacauac acgggaaacc uc                                            22

<210> SEQ ID NO 166
<211> LENGTH: 81
<212> TYPE: RNA
<213> ORGANISM: Artificial Sequence
<220> FEATURE:
<223> OTHER INFORMATION: miR-494 Stem Loop

<400> SEQUENCE: 166
gauacucgaa ggagagguug uccguguugu cuucucuuua uuuaugauga aacauacacg    60
ggaaaccucu uuuuaguau c                                              81

<210> SEQ ID NO 167
<211> LENGTH: 22
<212> TYPE: RNA
<213> ORGANISM: Artificial Sequence
<220> FEATURE:
<223> OTHER INFORMATION: miR-125b-2* Mature

<400> SEQUENCE: 167
ucacaaguca ggcucuuggg ac                                            22

<210> SEQ ID NO 168
<211> LENGTH: 89
<212> TYPE: RNA
<213> ORGANISM: Artificial Sequence
```

<220> FEATURE:
<223> OTHER INFORMATION: miR-125b-2* Stem Loop

<400> SEQUENCE: 168
accagacuuu uccuaguccc ugagacccua acuugugagg uauuuuagua acaucacaag    60
ucaggcucuu gggaccuagg cggagggga                                     89

<210> SEQ ID NO 169
<211> LENGTH: 22
<212> TYPE: RNA
<213> ORGANISM: Artificial Sequence
<220> FEATURE:
<223> OTHER INFORMATION: miR-210 Mature

<400> SEQUENCE: 169
cugugcgugu gacagcggcu ga                                            22

<210> SEQ ID NO 170
<211> LENGTH: 110
<212> TYPE: RNA
<213> ORGANISM: Artificial Sequence
<220> FEATURE:
<223> OTHER INFORMATION: miR-210 Stem loop

<400> SEQUENCE: 170
acccggcagu gccuccaggc gcagggcagc cccugcccac cgcacacugc gcugcccag    60 acccacugug cgugugacag cggcugaucu gugccugggc agcgcgaccc              110

<210> SEQ ID NO 171
<211> LENGTH: 22
<212> TYPE: RNA
<213> ORGANISM: Artificial Sequence
<220> FEATURE:
<223> OTHER INFORMATION: miR-1249 Mature

<400> SEQUENCE: 171
acgcccuucc cccccuucuu ca                                            22

<210> SEQ ID NO 172
<211> LENGTH: 66
<212> TYPE: RNA
<213> ORGANISM: Artificial Sequence
<220> FEATURE:
<223> OTHER INFORMATION: miR-1249 Stem Loop

<400> SEQUENCE: 172
gggaggaggg aggagauggg ccaaguuccc ucuggcugga acgcccuucc cccccuucuu    60
caccug                                                              66

<210> SEQ ID NO 173
<211> LENGTH: 22
<212> TYPE: RNA
<213> ORGANISM: Artificial Sequence
<220> FEATURE:
<223> OTHER INFORMATION: miR-874 Mature

<400> SEQUENCE: 173
cugcccuggc ccgagggacc ga                                            22

<210> SEQ ID NO 174
<211> LENGTH: 78
<212> TYPE: RNA
<213> ORGANISM: Artificial Sequence
<220> FEATURE:

<223> OTHER INFORMATION: miR-874 Stem Loop

<400> SEQUENCE: 174
uuagcccugc ggccccacgc accaggguaa gagagacucu cgcuuccugc ccuggcccga    60
gggaccgacu ggcugggc                                                 78

<210> SEQ ID NO 175
<211> LENGTH: 22
<212> TYPE: RNA
<213> ORGANISM: Artificial Sequence
<220> FEATURE:
<223> OTHER INFORMATION: miR-23a* Mature

<400> SEQUENCE: 175
gggguuccug gggaugggau uu                                            22

<210> SEQ ID NO 176
<211> LENGTH: 73
<212> TYPE: RNA
<213> ORGANISM: Artificial Sequence
<220> FEATURE:
<223> OTHER INFORMATION: miR-23a* Stem Loop

<400> SEQUENCE: 176
ggccggcugg gguuccuggg gaugggauuu gcuuccuguc acaaaucaca uugccaggga    60
uuuccaaccg acc                                                      73

<210> SEQ ID NO 177
<211> LENGTH: 22
<212> TYPE: RNA
<213> ORGANISM: Artificial Sequence
<220> FEATURE:
<223> OTHER INFORMATION: miR-30b* Mature

<400> SEQUENCE: 177
cugggaggug gauguuuacu uc                                            22

<210> SEQ ID NO 178
<211> LENGTH: 88
<212> TYPE: RNA
<213> ORGANISM: Artificial Sequence
<220> FEATURE:
<223> OTHER INFORMATION: miR-30b* Stem Loop

<400> SEQUENCE: 178
accaaguuuc aguucaugua aacauccuac acucagcugu aauacaugga uuggcuggga    60 ggugauguu uacuucagcu gacuugga                                       88

<210> SEQ ID NO 179
<211> LENGTH: 21
<212> TYPE: RNA
<213> ORGANISM: Artificial Sequence
<220> FEATURE:
<223> OTHER INFORMATION: miR-296-5p Mature

<400> SEQUENCE: 179
agggcccccc cucaauccug u                                             21

<210> SEQ ID NO 180
<211> LENGTH: 80
<212> TYPE: RNA
<213> ORGANISM: Artificial Sequence
<220> FEATURE:
<223> OTHER INFORMATION: miR-296-5p Stem Loop

<400> SEQUENCE: 180
aggacccuuc cagagggccc ccccucaauc cuguugugcc uaauucagag gguugggugg    60
aggcucuccu gaagggcucu                                                80

<210> SEQ ID NO 181
<211> LENGTH: 22
<212> TYPE: RNA
<213> ORGANISM: Artificial Sequence
<220> FEATURE:
<223> OTHER INFORMATION: miR-744 Mature

<400> SEQUENCE: 181
ugcggggcua gggcuaacag ca                                             22

<210> SEQ ID NO 182
<211> LENGTH: 22
<212> TYPE: RNA
<213> ORGANISM: Artificial Sequence
<220> FEATURE:
<223> OTHER INFORMATION: miR-197 Mature

<400> SEQUENCE: 182
uucaccaccu ucuccaccca gc                                             22

<210> SEQ ID NO 183
<211> LENGTH: 75
<212> TYPE: RNA
<213> ORGANISM: Artificial Sequence
<220> FEATURE:
<223> OTHER INFORMATION: miR-197 Stem Loop

<400> SEQUENCE: 183
ggcugugccg gguagagagg gcagugggag guaagagcuc uucacccuuc accaccuucu    60
ccacccagca uggcc                                                     75

<210> SEQ ID NO 184
<211> LENGTH: 22
<212> TYPE: RNA
<213> ORGANISM: Artificial Sequence
<220> FEATURE:
<223> OTHER INFORMATION: miR-27b* Mature

<400> SEQUENCE: 184
agagcuuagc ugauuggug ac                                              22

<210> SEQ ID NO 185
<211> LENGTH: 97
<212> TYPE: RNA
<213> ORGANISM: Artificial Sequence
<220> FEATURE:
<223> OTHER INFORMATION: miR-27b* Stem Loop

<400> SEQUENCE: 185
accucucuaa caaggugcag agcuuagcug auuggugaac agugauuggu uuccgcuuug    60
uucacagugg cuaaguucug caccugaaga gaaggug                             97

<210> SEQ ID NO 186
<211> LENGTH: 20
<212> TYPE: RNA
<213> ORGANISM: Artificial Sequence
<220> FEATURE:
<223> OTHER INFORMATION: miR-324-3p *Mature

```
<400> SEQUENCE: 186
acugccccag gugcugcugg                                               20

<210> SEQ ID NO 187
<211> LENGTH: 83
<212> TYPE: RNA
<213> ORGANISM: Artificial Sequence
<220> FEATURE:
<223> OTHER INFORMATION: miR-324-3p * Stem Loop

<400> SEQUENCE: 187
cugacuaugc cuccccgcau ccccuagggc auuggluguaa agcuggagac ccacugcccc   60
aggugcugcu gggggulugua guc                                          83

<210> SEQ ID NO 188
<211> LENGTH: 21
<212> TYPE: RNA
<213> ORGANISM: Artificial Sequence
<220> FEATURE:
<223> OTHER INFORMATION: miR-126 Mature

<400> SEQUENCE: 188
cauuauuacu uuugguacgc g                                             21

<210> SEQ ID NO 189
<211> LENGTH: 85
<212> TYPE: RNA
<213> ORGANISM: Artificial Sequence
<220> FEATURE:
<223> OTHER INFORMATION: miR-126 Mature

<400> SEQUENCE: 189
cgcuggcgac gggacauuau uacuuuuggu acgcgcugug acacuucaaa cucguaccgu   60
gaguaauaau gcgccgucca cggca                                         85

<210> SEQ ID NO 190
<211> LENGTH: 23
<212> TYPE: RNA
<213> ORGANISM: Artificial Sequence
<220> FEATURE:
<223> OTHER INFORMATION: miR-34a Mature

<400> SEQUENCE: 190
aacauucaac gcugucggug agu                                           23

<210> SEQ ID NO 191
<211> LENGTH: 110
<212> TYPE: RNA
<213> ORGANISM: Artificial Sequence
<220> FEATURE:
<223> OTHER INFORMATION: miR-34a Stem Loop

<400> SEQUENCE: 191
ggccagcugu gaguguuucu uuggcagugu cuuagcuggu uguugugagc aauaguaagg   60
aagcaaucag caaguauacu gcccuagaag ugcugcacgu ugugggggccc             110

<210> SEQ ID NO 192
<211> LENGTH: 22
<212> TYPE: RNA
<213> ORGANISM: Artificial Sequence
<220> FEATURE:
<223> OTHER INFORMATION: miR-34b Mature

<400> SEQUENCE: 192
```

-continued uaggcagugu cauuagcuga uu                                              22

<210> SEQ ID NO 193
<211> LENGTH: 84
<212> TYPE: RNA
<213> ORGANISM: Artificial Sequence
<220> FEATURE:
<223> OTHER INFORMATION: miR-34b Stem Loop

<400> SEQUENCE: 193
gugcucgguu uguaggcagu gucauuagcu gauuguacug ugguguuac aaucacuaac      60 uccacugcca ucaaaacaag gcac                                            84

<210> SEQ ID NO 194
<211> LENGTH: 23
<212> TYPE: RNA
<213> ORGANISM: Artificial Sequence
<220> FEATURE:
<223> OTHER INFORMATION: miR-34c Mature

<400> SEQUENCE: 194
aggcagugua guuagcugau ugc                                             23

<210> SEQ ID NO 195
<211> LENGTH: 77
<212> TYPE: RNA
<213> ORGANISM: Artificial Sequence
<220> FEATURE:
<223> OTHER INFORMATION: miR-34c Stem Loop

<400> SEQUENCE: 195
agucuaguua cuaggcagug uaguuagcug auugcuaaua guaccaauca cuaaccacac     60
ggccagguaa aagauu                                                     77

<210> SEQ ID NO 196
<211> LENGTH: 17
<212> TYPE: RNA
<213> ORGANISM: Artificial Sequence
<220> FEATURE:
<223> OTHER INFORMATION: miR-1280 Mature

<400> SEQUENCE: 196
ucccaccgcu gccaccc                                                    17

<210> SEQ ID NO 197
<211> LENGTH: 94
<212> TYPE: RNA
<213> ORGANISM: Artificial Sequence
<220> FEATURE:
<223> OTHER INFORMATION: miR-1280 Stem Loop

<400> SEQUENCE: 197
ucugucccac cgcugccacc cuccccucug ccucagugug ccaggcauca gcacucacuc     60
acagaggcag gcuggauggc ggugggaca acag                                  94

<210> SEQ ID NO 198
<211> LENGTH: 23
<212> TYPE: RNA
<213> ORGANISM: Artificial Sequence
<220> FEATURE:
<223> OTHER INFORMATION: Hs_miR-181a primer

<400> SEQUENCE: 198

```
aacauucaac gcugucggug agu                                              23

<210> SEQ ID NO 199
<211> LENGTH: 17
<212> TYPE: RNA
<213> ORGANISM: Artificial Sequence
<220> FEATURE:
<223> OTHER INFORMATION: Hs_miR-181a primer

<400> SEQUENCE: 199
ucccaccgcu gccaccc                                                     17

<210> SEQ ID NO 200
<211> LENGTH: 88
<212> TYPE: RNA
<213> ORGANISM: Artificial Sequence
<220> FEATURE:
<223> OTHER INFORMATION: miR-320c Stem Loop

<400> SEQUENCE: 200
uuugcauuaa aaaugaggcc uucucuuccc aguucuuccc agagucagga aaagcugggu       60
ugagagggua gaaaaaaaau gauguagg                                         88

<210> SEQ ID NO 201
<211> LENGTH: 98
<212> TYPE: RNA
<213> ORGANISM: Artificial Sequence
<220> FEATURE:
<223> OTHER INFORMATION: miR-744 Stem Loop

<400> SEQUENCE: 201
uugggcaagg ugcggggcua gggcuaacag cagucuuacu gaagguuucc uggaaaccac       60
gcacaugcug uugccacuaa ccucaaccuu acucgguc                              98
```

METHODS FOR TREATING CHONDROSARCOMA USING MICRORNA(MIR)

CROSS-REFERENCE TO RELATED APPLICATIONS

This application is a national stage application filed under 35 U.S.C. § 371, of International Patent Application No. PCT/US2017/20975, filed Mar. 6, 2017, which claims the benefit of and priority to U.S. Provisional Patent Application No. 62/304,048, filed Mar. 4, 2016, the entire contents of which are incorporated by reference herein for all purposes.

GOVERNMENT INTEREST

The invention was made with government support under grant numbers 1R01CA166089-01 and P20GM104937 awarded by The National Institutes of Health. The government has certain rights in the present invention.

INCORPORATION BY REFERENCE OF SEQUENCE LISTING

The contents of the text file named "021486-627N01US_Sequence_Listing_ST25", which was created on Sep. 3, 2018, and is 46,197 bytes in size, are hereby incorporated by reference in their entireties and for all purposes.

FIELD OF INVENTION

This invention is directed to, inter alia, compositions and methods for the treatment and diagnosis of chondrosarcoma via manipulation of cellular levels of microRNAs.

BACKGROUND

Chondrosarcoma is the second most common malignancy in bone and is a highly metastatic cancer with no effective systemic treatments. Chondrosarcoma results from unregulated growth of mesenchymal stem cells and is a cancer of cartilage. It tends to be locally invasive and then metastatic. One of the biggest problems associated with chondrosarcoma is that it does not respond to either chemotherapy or radiation. In the past several decades, mesenchymal malignancies such as osteosarcoma and Ewing sarcoma have seen a dramatic increase in long term survival. However, other mesenchymal malignancies, such as human chondrosarcoma, have a poor prognosis due to the absence of an effective adjuvant therapy. The failure of currently available treatments to offer significant increases in long-term survival for individuals with chondrosarcoma indicates an urgent need for the development of new therapies for the treatment of this disease.

SUMMARY

The invention provides a solution to the clinical problem of treatment for chondrosarcoma, e.g., an adjuvant-based therapy. Adjuvant therapy is an additional cancer treatment given after the primary treatment to lower the risk that the cancer will come back. In the case of chrondrosarcoma, primary treatment is typically surgical resection. Adjuvant therapy may include chemotherapy, radiation therapy, hormone therapy, targeted therapy, or biological therapy. Accordingly, in some aspects, a method for treating an individual with chondrosarcoma is provided by administering to the individual a therapeutically effective amount of an inhibitor of one or more microRNA (miR) selected from the group consisting of miR-199a-3p, miR-26a, miR-762, miR-125a-5p, miR-let-7g, miR-16, miR-let-7f, miR-21, miR-let-7a, miR-638, miR-23a, miR-92a, miR-15b, miR-23b, miR-451, miR-483-5p, miR-15a, miR-27a, miR-26b, miR-let-7d, miR-27-b, miR-98, miR-145, miR-143, miR-1915, miR-149*, miR-7i, miR-7c, miR-7e, miR-93b, miR-let-7b, miR-30c, miR-181d, miR-148a, miR-181c, miR-196a, miR-30a, miR-214, miR-187*, miR-663, miR-146a, miR-30d, miR-365, miR-424, miR-1231, miR-424*, miR-454, miR-455-5p, miR-337-3p, miR-381, miR-let-7a-2*, miR-181a, and miR-30e. The methods described herein leads to inhibition of tumor progression (i.e. growth and metastasis) and can be used alone or in combination with other treatments for chondrosarcoma, such as surgical ablation.

Suitable compounds for inhibiting miR gene expression include, without limitation, antagomirs, double-stranded RNA (such as short- or small-interfering RNA or "siRNA"), antisense nucleic acids, enzymatic RNA molecules such as ribozymes, or molecules capable of forming a triple helix with the miR gene. In some embodiments, the inhibitor molecule causes post-transcriptional silencing of the miR. In some embodiments, the inhibitor molecule inhibits maturation of the miR (i.e. inhibits or prevents expression or function of the stem-loop-based precursor molecule). In some embodiments, the inhibitor molecule is administered as naked RNA, in conjunction with a delivery agent (such as, for example, an anionic lipid-based delivery agent).

Nucleotide sequences of miRs targeted for inhibition by the methods disclosed herein (and their corresponding mature forms) are listed below. Exemplary miRs range in size from 50-90 nucleotides in length (or any length within that range, with an average length of approximately 70 nucleotides) for miR stem-loop precursors and exemplary mature oligonucleotide compounds are 17 to 25 nucleotides in length, e.g., are 17, 18, 19, 20, 21, 22, 23, 24 or 25 nucleotides in length. For example, a stem-loop precursor is approximately 70 nucleotides and the mature nucleotide product is approximately 22 nucleotides (such as any of about 16, 17, 18, 19, 20, 21, 22, 23, 24, 25, 26, or 27 nucleotides) in length. A stem-loop precursor comprises a stem-loop secondary structure.

```
miR-199a-3p (MIMAT0000232):
Mature:
                                      (SEQ ID NO: 1)
ACAGUAGUCUGCACAUUGGUUA Stem loop:
                                      (SEQ ID NO: 2)
GCCAACCCAGUGUUCAGACUACCUGUUCAGGAGGCUCUCAAUGUGUACAG

UAGUCUGCACAUUGGUUAGGC miR-26a (MIMAT0000082):
Mature:
                                      (SEQ ID NO: 3)
UUCAAGUAAUCCAGGAUAGGCU Stem loop:
                                      (SEQ ID NO: 4)
GUGGCCUCGUUCAAGUAAUCCAGGAUAGGCUGUGCAGGUCCCAAUGGGCC

UAUUCUUGGUUACUUGCACGGGACGC
``` miR-762 (MIMAT0010313):
Mature:
(SEQ ID NO: 5)
GGGGCUGGGGCCGGGGCCGAGC

Stem loop:
(SEQ ID NO: 6)
GGCCCGGCUCCGGGUCUCGGCCCGUACAGUCCGGCCGGCCAUGCUGGCGG

GGCUGGGGCCGGGGCCGAGCCCGCGGCGGGGCC miR-125a-5p (MIMAT0000443):
Mature:
(SEQ ID NO: 7)
UCCCUGAGACCCUUUAACCUGUGA Stem loop:
(SEQ ID NO: 8)
UGCCAGUCUCUAGGUCCCUGAGACCCUUUAACCUGUGAGGACAUCCAGGG

UCACAGGUGAGGUUCUUGGGAGCCUGGCGUCUGGCC miR-let-7G (MIMAT0000414):
Mature:
(SEQ ID NO: 9)
UGAGGUAGUAGUUUGUACAGUU Stem loop:
(SEQ ID NO: 10)
AGGCUGAGGUAGUAGUUUGUACAGUUUGAGGGUCUAUGAUACCACCCGGU

ACAGGAGAUAACUGUACAGGCCACUGCCUUGCCA miR-16 (MIMAT0000069):
Mature:
(SEQ ID NO: 11)
UAGCAGCACGUAAAUAUUGGCG Stem loop:
(SEQ ID NO: 12)
GUCAGCAGUGCCUUAGCAGCACGUAAAUAUUGGCGUUAAGAUUCUAAAAU

UAUCUCCAGUAUUAACUGUGCUGCUGAAGUAAGGUUGAC let-7f (MIMAT0000067):
Mature:
(SEQ ID NO: 13)
UGAGGUAGUAGAUUGUAUAGUU Stem loop:
(SEQ ID NO: 14)
UCAGAGUGAGGUAGUAGAUUGUAUAGUUGUGGGGUAGUGAUUUUACCCUG

UUCAGGAGAUAACUAUACAAUCUAUUGCCUUCCCUGA miR-21 (MIMAT0000076):
Mature:
(SEQ ID NO: 15)
UAGCUUAUCAGACUGAUGUUGA Stem loop:
(SEQ ID NO: 16)
UGUCGGGUAGCUUAUCAGACUGAUGUUGACUGUUGAAUCUCAUGGCAACA

CCAGUCGAUGGGCUGUCUGACA miR-Let-7a (MIMAT0000062):
Mature:
(SEQ ID NO: 17)
UGAGGUAGUAGGUUGUAUAGUU Stem loop:
(SEQ ID NO: 18)
UGGGAUGAGGUAGUAGGUUGUAUAGUUUUAGGGUCACACCCACCACUGGG

AGAUAACUAUACAAUCUACUGUCUUUCCUA miR-638 (MIMAT0003308):
Mature:
(SEQ ID NO: 19)
AGGGAUCGCGGGCGGGUGGCGGCCU Stem loop:
(SEQ ID NO: 102)
GUGAGCGGGCGCGGCAGGGAUCGCGGGCGGGUGGCGGCCUAGGGCGCGGA

GGGCGGACCGGGAAUGGCGCGCCGUGCGCCGCCGGCGUAACUGCGGCGCU miR-23a (MIMAT0000078):
Mature:
(SEQ ID NO: 20)
AUCACAUUGCCAGGGAUUUCC Stem loop:
(SEQ ID NO: 21)
GGCCGGCUGGGGUUCCUGGGGAUGGGAUUUGCUUCCUGUCACAAAUCACA

UUGCCAGGGAUUUCCAACCGACC miR-92a (MIMAT0000092):
Mature:
(SEQ ID NO: 22)
UAUUGCACUUGUCCCGGCCUGU Stem loop:
(SEQ ID NO: 23)
CUUUCUACACAGGUUGGGAUCGGUUGCAAUGCUGUGUUUCUGUAUGGUAU

UGCACUUGUCCCGGCCUGUUGAGUUUGG miR-15b (MIMAT0000417):
Mature:
(SEQ ID NO: 24)
UAGCAGCACAUCAUGGUUUACA Stem loop:
(SEQ ID NO: 25)
UUGAGGCCUUAAAGUACUGUAGCAGCACAUCAUGGUUUACAUGCUACAGU

CAAGAUGCGAAUCAUUAUUUGCUGCUCUAGAAAUUUAAGGAAAUUCAU miR-23b (MIMAT0000418):
Mature:
(SEQ ID NO: 26)
AUCACAUUGCCAGGGAUUACC Stem loop:
(SEQ ID NO: 27)
CUCAGGUGCUCUGGCUGCUUGGGUUCCUGGCAUGCUGAUUUGUGACUUAA

GAUUAAAAUCACAUUGCCAGGGAUUACCACGCAACCACGACCUUGGC miR-451 (MIMAT0001631):
Mature:
(SEQ ID NO: 28)
AAACCGUUACCAUUACUGAGUU Stem loop:
(SEQ ID NO: 29)
CUUGGGAAUGGCAAGGAAACCGUUACCAUUACUGAGUUUAGUAAUGGUAA

UGGUUCUCUUGCUAUACCCAGA miR-483-5P (MIMAT0004761):
Mature:
(SEQ ID NO: 30)
AAGACGGGAGGAAAGAAGGGAG Stem loop:
(SEQ ID NO: 103)
GAGGGGGAAGACGGGAGGAAAGAAGGGAGUGGUUCCAUCACGCCUCCUCA

CUCCUCUCCUCCCGUCUUCUCCUCUC

-continued miR-15a (MIMAT0000068):
Mature:
(SEQ ID NO: 31)
UAGCAGCACAUAAUGGUUUGUG Stem loop:
(SEQ ID NO: 32)
CCUUGGAGUAAAGUAGCAGCACAUAAUGGUUUGUGGAUUUUGAAAAGGUG

CAGGCCAUAUUGUGCUGCCUCAAAAAUACAAGG miR-27a (MIMAT0000084):
Mature:
(SEQ ID NO: 33)
UUCACAGUGGCUAAGUUCCGC Stem loop:
(SEQ ID NO: 34)
CUGAGGAGCAGGGCUUAGCUGCUUGUGAGCAGGGUCCACACCAAGUCGUG

UUCACAGUGGCUAAGUUCCGCCCCCCAG miR-26b (MIMAT0000083):
Mature:
(SEQ ID NO: 35)
UUCAAGUAAUUCAGGAUAGGU Stem loop:
(SEQ ID NO: 36)
CCGGGACCCAGUUCAAGUAAUUCAGGAUAGGUUGUGUGCUGUCCAGCCUG

UUCUCCAUUACUUGGCUCGGGGACCGG miR-let-7d (MIMAT0000065):
Mature:
(SEQ ID NO: 37)
AGAGGUAGUAGGUUGCAUAGUU Stem loop:
(SEQ ID NO: 38)
CCUAGGAAGAGGUAGUAGGUUGCAUAGUUUUAGGGCAGGGAUUUUGCCCA

CAAGGAGGUAACUAUACGACCUGCUGCCUUUCUUAGG miR-27b (MIMAT0000419):
Mature:
(SEQ ID NO: 39)
UUCACAGUGGCUAAGUUCUGC Stem loop:

miR-98 (MIMAT0000096):
Mature:
(SEQ ID NO: 40)
UGAGGUAGUAAGUUGUAUUGUU

Stem loop:
(SEQ ID NO: 41)
AGGAUUCUGCUCAUGCCAGGGUGAGGUAGUAAGUUGUAUUGUUGUGGGGU

AGGGAUAUUAGGCCCCAAUUAGAAGAUAACUAUACAACUUACUACUUUCC

UGGUGUGUGGCAUAUUCA miR-145 (MIMAT0000437):
Mature:
(SEQ ID NO: 42)
GUCCAGUUUUCCCAGGAAUCCCU Stem loop:
(SEQ ID NO: 43)
CACCUUGUCCUCACGGUCCAGUUUUCCCAGGAAUCCCUUAGAUGCUAAGA

UGGGGAUUCCUGGAAAUACUGUUCUUGAGGUCAUGGUU miR-143 (MIMAT0000435):
Mature:
(SEQ ID NO: 44)
UGAGAUGAAGCACUGUAGCUC Stem loop:
(SEQ ID NO: 45)
GCGCAGCGCCCUGUCUCCCAGCCUGAGGUGCAGUGCUGCAUCUCUGGUCA

GUUGGGAGUCUGAGAUGAAGCACUGUAGCUCAGGAAGAGAGAAGUUGUUC

UGCAGC miR-1915 (MIMAT0007892):
Mature:
(SEQ ID NO: 46)
CCCCAGGGCGACGCGGCGGG

Stem loop:
(SEQ ID NO: 47)
UGAGAGGCCGCACCUUGCCUUGCUGCCCGGGCCGUGCACCCGUGGGCCCC

AGGGCGACGCGGCGGGGGCGGCCCUAGCGA mir-149* (MIMAT0004609):
Mature:
(SEQ ID NO: 48)
AGGGAGGGACGGGGGCUGUGC Stem loop:
(SEQ ID NO: 49)
GCCGGCGCCCGAGCUCUGGCUCCGUGUCUUCACUCCCGUGCUUGUCCGAG

GAGGGAGGGAGGGACGGGGGCUGUGCUGGGGCAGCUGGA miR-7i (MIMAT0000415):
Mature:
(SEQ ID NO: 50)
UGAGGUAGUAGUUUGUGCUGUU Stem loop:
(SEQ ID NO: 51)
CUGGCUGAGGUAGUAGUUUGUGCUGUUGGUCGGGUUGUGACAUUGCCCGC

UGUGGAGAUAACUGCGCAAGCUACUGCCUUGCUA let-7c (MIMAT0000064):
Mature:
(SEQ ID NO: 52)
UGAGGUAGUAGGUUGUAUGGUU Stem loop:
(SEQ ID NO: 53)
GCAUCCGGGUUGAGGUAGUAGGUUGUAUGGUUUAGAGUUACACCCUGGGA

GUUAACUGUACAACCUUCUAGCUUUCCUUGGAGC let-7e (MIMAT0000066):
Mature:
(SEQ ID NO: 54)
UGAGGUAGGAGGUUGUAUAGUU Stem loop:
(SEQ ID NO: 55)
CCCGGGCUGAGGUAGGAGGUUGUAUAGUUGAGGAGGACACCCAAGGAGAU

CACUAUACGGCCUCCUAGCUUUCCCCAGG miR-936 (MIMAT0004979):
Mature:
(SEQ ID NO: 56)
ACAGUAGAGGGAGGAAUCGCAG Stem loop:
(SEQ ID NO: 57)
UCAAGGCCACUGGGACAGUAGAGGGAGGAAUCGCAGAAAUCACUCCAGGA

GCAACUGAGAGACCUUGCUUCUACUUUACCAGGUCCUGCUGGCCCAGA miR-let-7b (MIMAT0000063):
Mature:
(SEQ ID NO: 58)
UGAGGUAGUAGGUUGUGUGGUU -continued Stem loop:
(SEQ ID NO: 59)
CGGGGUGAGGUAGUAGGUUGUGUGGUUUCAGGGCAGUGAUGUUGCCCCUC

GGAAGAUAACUAUACAACCUACUGCCUUCCCUG miR-30c (MIMAT0000244):
Mature:
(SEQ ID NO: 60)
UGUAAACAUCCUACACUCUCAGC Stem loop:
(SEQ ID NO: 61)
AGAUACUGUAAACAUCCUACACUCUCAGCUGUGGAAAGUAAGAAAGCUGG

GAGAAGGCUGUUUACUCUUUCU miR-181d (MIMAT0002821):
Mature:
(SEQ ID NO: 62)
AACAUUCAUUGUUGUCGGUGGGU Stem loop:
(SEQ ID NO: 63)
GUCCCCUCCCCUAGGCCACAGCCGAGGUCACAAUCAACAUUCAUUGUUGU

CGGUGGGUUGUGAGGACUGAGGCCAGACCCACCGGGGAUGAAUGUCACU

GUGGCUGGGCCAGACACGGCUUAAGGGGAAUGGGGAC miR-148a (MIMAT0000243):
Mature:
(SEQ ID NO: 64)
UCAGUGCACUACAGAACUUUGU Stem loop:
(SEQ ID NO: 65)
GAGGCAAAGUUCUGAGACACUCCGACUCUGAGUAUGAUAGAAGUCAGUGC

ACUACAGAACUUUGUCUC miR-181c (MIMAT0000258):
Mature:
(SEQ ID NO: 66)
AACAUUCAACCUGUCGGUGAGU Stem loop:
(SEQ ID NO: 67)
CGGAAAAUUUGCCAAGGGUUUGGGGGAACAUUCAACCUGUCGGUGAGUUU

GGGCAGCUCAGGCAAACCAUCGACCGUUGAGUGGACCCUGAGGCCUGGAA

UUGCCAUCU miR-196a (MIMAT0000226):
Mature:
(SEQ ID NO: 68)
UAGGUAGUUUCAUGUUGUUGGG Stem loop:
(SEQ ID NO: 69)
GUGAAUUAGGUAGUUUCAUGUUGUUGGGCCUGGGUUUCUGAACACAACAA

CAUUAAACCACCCGAUUCAC miR-30a (MIMAT0000087):
Mature:
(SEQ ID NO: 70)
UGUAAACAUCCUCGACUGGAAG Stem loop:
(SEQ ID NO: 71)
GCGACUGUAAACAUCCUCGACUGGAAGCUGUGAAGCCACAGAUGGGCUUU

CAGUCGGAUGUUUGCAGCUGC miR-214 (MIMAT0000271):
Mature:
(SEQ ID NO: 72)
ACAGCAGGCACAGACAGGCAGU -continued Stem loop:
(SEQ ID NO: 73)
GGCCUGGCUGGACAGAGUUGUCAUGUGUCUGCCUGUCUACACUUGCUGUG

CAGAACAUCCGCUCACCUGUACAGCAGGCACAGACAGGCAGUCACAUGAC

AACCCAGCU miR-187* (MIMAT0004561):
Mature:
(SEQ ID NO: 74)
GGCUACAACACAGGACCCGGGC Stem loop:
(SEQ ID NO: 75)
GGUCGGGCUCACCAUGACACAGUGUGAGACCUCGGGCUACAACACAGGAC

CCGGGCGCUGCUCUGACCCCUCGUGUCUUGUGUUGCAGCCGGAGGGACGC

AGGUCCGCA miR-663 (MIMAT0003326):
Mature:
(SEQ ID NO: 76)
AGGCGGGGCGCCGCGGGACCGC Stem loop:
(SEQ ID NO: 77)
CCUUCCGGCGUCCCAGGCGGGGCGCCGCGGGACCGCCCCUCGUGUCUGUGG

CGGUGGGAUCCCGCGGCCGUGUUUUCCUGGUGGCCCGGCCAUG miR-146a (MIMAT0000449):
Mature:
(SEQ ID NO: 78)
UGAGAACUGAAUUCCAUGGGUU Stem loop:
(SEQ ID NO: 79)
CCGAUGUGUAUCCUCAGCUUUGAGAACUGAAUUCCAUGGGUUGUGUCAGU

GUCAGACCUCUGAAAUUCAGUUCUUCAGCUGGGAUAUCUCUGUCAUCGU miR-30d (MIMAT0000245):
Mature:
(SEQ ID NO: 80)
UGUAAACAUCCCCGACUGGAAG Stem loop:
(SEQ ID NO: 81)
GUUGUUGUAAACAUCCCCGACUGGAAGCUGUAAGACACAGCUAAGCUUUC

AGUCAGAUGUUUGCUGCUAC miR-365 (MIMAT0000710):
Mature:
(SEQ ID NO: 82)
UAAUGCCCCUAAAAAUCCUUAU Stem loop:
(SEQ ID NO: 83)
ACCGCAGGGAAAAUGAGGGACUUUUGGGGGCAGAUGUGUUUCCAUUCCAC

UAUCAUAAUGCCCCUAAAAAUCCUUAUUGCUCUUGCA miR-424 (MIMAT0001341):
Mature:
(SEQ ID NO: 84)
CAGCAGCAAUUCAUGUUUUGAA Stem loop:
(SEQ ID NO: 85)
CGAGGGGAUACAGCAGCAAUUCAUGUUUUGAAGUGUUCUAAAUGGUUCAA

AACGUGAGGCGCUGCUAUACCCCCUCGUGGGGAAGGUAGAAGGUGGGG miR-1231 (MIMAT0005586):
Mature:
(SEQ ID NO: 86)
GUGUCUGGGCGGACAGCUGC Stem loop:
(SEQ ID NO: 87)
GUCAGUGUCUGGGCGGACAGCUGCAGGAAAGGGAAGACCAAGGCUUGCUG

UCUGUCCAGUCUGCCACCCUACCCUGUCUGUUCUUGCCACAG miR-424* (MIMAT0004749):
Mature:
(SEQ ID NO: 88)
CAAAACGUGAGGCGCUGCUAU Stem loop:
(SEQ ID NO: 89)
CGAGGGGAUACAGCAGCAAUUCAUGUUUUGAAGUGUUCUAAAAUGGUUCAA

AACGUGAGGCGCUGCUAUACCCCCUCGUGGGGAAGGUAGAAGGUGGGG miR-454 (MIMAT0003885):
Mature:
(SEQ ID NO: 90)
UAGUGCAAUAUUGCUUAUAGGGU Stem loop:
(SEQ ID NO: 91)
UCUGUUUAUCACCAGAUCCUAGAACCCUAUCAAUAUUGUCUCUGCUGUGU

AAAUAGUUCUGAGUAGUGCAAUAUUGCUUAUAGGGUUUUGGUGUUUGGAA

AGAACAAUGGGCAGG miR-455-5p (MIMAT0003150):
Mature:
(SEQ ID NO: 92)
UAUGUGCCUUUGGACUACAUCG Stem loop:
(SEQ ID NO: 93)
UCCCUGGCGUGAGGGUAUGUGCCUUUGGACUACAUCGUGGAAGCCAGCAC

CAUGCAGUCCAUGGGCAUAUACACUUGCCUCAAGGCCUAUGUCAUC miR-337-3p (MIMAT0000754):
Mature:
(SEQ ID NO: 94)
CUCCUAUAUGAUGCCUUUCUUC Stem loop:
(SEQ ID NO: 95)
GUAGUCAGUAGUUGGGGGUGGGAACGGCUUCAUACAGGAGUUGAUGCAC

AGUUAUCCAGCUCCUAUAUGAUGCCUUUCUUCAUCCCCUUCAA miR-381 (MIMAT0000736):
Mature:
(SEQ ID NO: 96)
UAUACAAGGGCAAGCUCUCUGU Stem loop:
(SEQ ID NO: 97)
UACUUAAAGCGAGGUUGCCCUUUGUAUAUUCGGUUUAUUGACAUGGAAUA

UACAAGGGCAAGCUCUCUGUGAGUA miR-30e (MIMAT0000692):
Mature:
(SEQ ID NO: 98)
UGUAAACAUCCUUGACUGGAAG Stem loop:
(SEQ ID NO: 99)
GGGCAGUCUUUGCUACUGUAAACAUCCUUGACUGGAAGCUGUAAGGUGUU

CAGAGGAGCUUUCAGUCGGAUGUUUACAGCGGCAGGCUGCCA miR-181a (MI0000269)
Mature:
(SEQ ID NO: 100)
AACAUUCAACGCUGUCGGUGAGU Stem loop:
(SEQ ID NO: 101)
AGAAGGGCUAUCAGGCCAGCCUUCAGAGGACUCCAAGGAACAUUCAACGC

UGUCGGUGAGUUUGGGAUUUGAAAAAACCACUGACCGUUGACUGUACCUU

GGGGUCCUUA

In other aspects, a method for treating an individual with chondrosarcoma is provided by administering to the individual a therapeutically effective amount of a nucleic acid encoding one or more microRNA (miR) selected from the group consisting of miR-320c, miR-320b, miR-320a, miR-127-3p, miR-1260, miR-140-3p, miR-22, miR-146b-5p, miR-107, miR-320d, miR-423-5p, miR-1974, miR-455-3p, miR-193b*, miR-103, miR-432, miR-151-3p, miR-31, miR-664*, miR-486-5p, miR-99a, miR-24, miR-191, miR-99b, miR-574-5p, miR-151-5p, miR-193a-5p, miR-1246, miR-877, miR-940, miR-1281, miR-494, miR-125-b-2*, miR-210, miR-1249, miR-874, miR-23a*, miR-30b*, miR-296-5p, miR-744, miR-197, miR-27b*, miR-34a, miR-34b, miR-34c, miR-1280, miR-126, and miR-324-3p. In some embodiments, the nucleic acid is administered on a vector, for example, a viral vector or nanoparticle.

Nucleotide sequences of miR-encoding nucleic acids (such as miR-encoding nucleic acids which are part of a delivery construct, such as a viral vector) and combinations of the same (and their corresponding stem-loop forms) for use in the methods disclosed herein are listed below.

miR-320c (MIMAT0005793):
Mature:
(SEQ ID NO: 104)
AAAAGCUGGGUUGAGAGGGU

Stem loop:
(SEQ ID NO: 200)
UUUGCAUUAAAAAUGAGGCCUUCUCUUCCCAGUUCUUCCCAGAGUCAGGA

AAAGCUGGGUUGAGAGGGUAGAAAAAAAAAUGAUGUAGG miR-320b (MIMAT0005792):
Mature:
(SEQ ID NO: 105)
AAAAGCUGGGUUGAGAGGGCAA Stem loop:
(SEQ ID NO: 106)
AAUUAAUCCCUCUCUUUCUAGUUCUUCCUAGAGUGAGGAAAAGCUGGGUU

GAGAGGGCAAACAAAUUAACUAAUUAAUU miR-320a (MIMAT0000510):
Mature:
(SEQ ID NO: 107)
AAAAGCUGGGUUGAGAGGGCGA Stem loop:
(SEQ ID NO: 108)
GCUUCGCUCCCCUCCGCCUUCUCUUCCCGGUUCUUCCCGGAGUCGGGAAA

AGCUGGGUUGAGAGGGCGAAAAAGGAUGAGGU miR-127-3p (MIMAT0000446):
Mature:
(SEQ ID NO: 109)
UCGGAUCCGUCUGAGCUUGGCU Stem loop:
(SEQ ID NO: 110)
UGUGAUCACUGUCUCCAGCCUGCUGAAGCUCAGAGGGCUCUGAUUCAGAA

AGAUCAUCGGAUCCGUCUGAGCUUGGCUGGUCGGAAGUCUCAUCAUC miR-1260 (MIMAT0005911):
Mature:
(SEQ ID NO: 111)
AUCCCACCUCUGCCACCA Stem loop:
(SEQ ID NO: 112)
ACCUUUCCAGCUCAUCCCACCUCUGCCACCAAAAACACUCAUCGCGGGUC

AGAGGGAGUGCCAAAAAAGGUAA miR-140-3p (MIMAT0004597):
Mature:
(SEQ ID NO: 113)
UACCACAGGGUAGAACCACGG Stem loop:
(SEQ ID NO: 114)
UGUGUCUCUCUCUGUGUCCUGCCAGUGGUUUUACCCUAUGGUAGGUUACG

UCAUGCUGUUCUACCACAGGGUAGAACCACGGACAGGAUACCGGGGCACC miR-22 (MIMAT0000077):
Mature:
(SEQ ID NO: 115)
AAGCUGCCAGUUGAAGAACUGU Stem loop:
(SEQ ID NO: 116)
GGCUGAGCCGCAGUAGUUCUUCAGUGGCAAGCUUUAUGUCCUGACCCAGC

UAAAGCUGCCAGUUGAAGAACUGUUGCCCUCUGCC miR-146b-5p (MIMAT0002809):
Mature:
(SEQ ID NO: 117)
UGAGAACUGAAUUCCAUAGGCU Stem loop:
(SEQ ID NO: 118)
CCUGGCACUGAGAACUGAAUUCCAUAGGCUGUGAGCUCUAGCAAUGCCCU

GUGGACUCAGUUCUGGUGCCCGG miR-107 (MIMAT0000104):
Mature:
(SEQ ID NO: 119)
AGCAGCAUUGUACAGGGCUAUCA Stem loop:
(SEQ ID NO: 120)
CUCUCUGCUUUCAGCUUCUUUACAGUGUUGCCUUGUGGCAUGGAGUUCAA

GCAGCAUUGUACAGGGCUAUCAAAGCACAGA miR-320d (MIMAT0006764):
Mature:
(SEQ ID NO: 121)
AAAAGCUGGGUUGAGAGGA Stem loop:
(SEQ ID NO: 122)
UUCUCGUCCCAGUUCUUCCCAAAGUUGAGAAAAGCUGGGUUGAGAGGA miR-423-5p (MIMAT0004748):
Mature:
(SEQ ID NO: 123)
UGAGGGGCAGAGAGCGAGACUUU Stem loop:
(SEQ ID NO: 124)
AUAAAGGAAGUUAGGCUGAGGGGCAGAGAGCGAGACUUUUCUAUUUCCA

AAAGCUCGGUCUGAGGCCCCUCAGUCUUGCUUCCUAACCCGCGC miR-1974 (MIMAT0009449):
Mature:
(SEQ ID NO: 125)
UGGUUGUAGUCCGUGCGAGAAUA Stem loop:
(SEQ ID NO: 126)
UGUUCUUGUAGUUGAAAUACAACGAUGGUUUUUCAUAUCAUUGGUCGUGG

UUGUAGUCCGUGCGAGAAUA miR-455-3p (MIMAT0004784):
Mature:
(SEQ ID NO: 127)
GCAGUCCAUGGGCAUAUACAC Stem loop:
(SEQ ID NO: 128)
UCCCUGGCGUGAGGGUAUGUGCCUUUGGACUACAUCGUGGAAGCCAGCAC

CAUGCAGUCCAUGGGCAUAUACACUUGCCUCAAGGCCUAUGUCAUC miR-193b* (MIMAT0002819):
Mature:
(SEQ ID NO: 129)
AACUGGCCCUCAAAGUCCCGCU Stem loop:
(SEQ ID NO: 130)
GUGGUCUCAGAAUCGGGGUUUUGAGGGCGAGAUGAGUUUAUGUUUUAUCC

AACUGGCCCUCAAAGUCCCGCUUUUGGGGUCAU miR-103 (MIMAT0000101):
Mature:
(SEQ ID NO: 131)
AGCAGCAUUGUACAGGGCUAUGA Stem loop:
(SEQ ID NO: 132)
UUGUGCUUUCAGCUUCUUUACAGUGCUGCCUUGUAGCAUUCAGGUCAAGC

AGCUUGUACAGGGCUAUGAAAGAACCA miR-432 (MIMAT0002814):
Mature:
(SEQ ID NO: 133)
UCUUGGAGUAGGUCAUUGGGUGG Stem loop:
(SEQ ID NO: 134)
UGACUCCUCCAGGUCUUGGAGUAGGUCAUUGGGUGGAUCCUCUAUUUCCU

UACGUGGGCCACUGGAUGGCUCCUCCAUGUCUUGGAGUAGAUCA miR-151-3p (MIMAT0000757):
Mature:
(SEQ ID NO: 135)
CUAGACUGAAGCUCCUUGAGG Stem loop:
(SEQ ID NO: 136)
UUUCCUGCCCUCGAGGAGCUCACAGUCUAGUAUGUCUCAUCCCCUACUAG

ACUGAAGCUCCUUGAGGACAGGGAUGGUCAUACUCACCUC miR-31 (MIMAT0000089):
Mature:
(SEQ ID NO: 137)
AGGCAAGAUGCUGGCAUAGCU Stem loop:
(SEQ ID NO: 138)
GGAGAGGAGGCAAGAUGCUGGCAUAGCUGUUGAACUGGGAACCUGCUAUG

CCAACAUAUUGCCAUCUUUCC miR-664* (MIMAT0005948):
Mature:
(SEQ ID NO: 139)
ACUGGCUAGGGAAAAUGAUUGGAU Stem loop:
(SEQ ID NO: 140)
GAACAUUGAAACUGGCUAGGGAAAAUGAUUGGAUAGAAACUAUUAUUCUA

UUCAUUUAUCCCCAGCCUACAAAAUGAAAAAA miR-486-5p (MIMAT0002177):
Mature:
(SEQ ID NO: 141)
UCCUGUACUGAGCUGCCCCGAG Stem loop:
(SEQ ID NO: 142)
GCAUCCUGUACUGAGCUGCCCCGAGGCCCUUCAUGCUGCCCAGCUCGGGG

CAGCUCAGUACAGGAUAC miR-99a (MIMAT0000097):
Mature:
(SEQ ID NO: 143)
AACCCGUAGAUCCGAUCUUGUG Stem loop:
(SEQ ID NO: 144)
CCCAUUGGCAUAAACCCGUAGAUCCGAUCUUGUGGUGAAGUGGACCGCAC

AAGCUCGCUUCUAUGGGUCUGUGUCAGUGUG miR-24 (MIMAT0000080):
Mature:
(SEQ ID NO: 145)
UGGCUCAGUUCAGCAGGAACAG Stem loop:
(SEQ ID NO: 146)
CUCCGGUGCCUACUGAGCUGAUAUCAGUUCUCAUUUUACACACUGGCUCA

GUUCAGCAGGAACAGGAG miR-191 (MIMAT0000440):
Mature:
(SEQ ID NO: 147)
CAACGGAAUCCCAAAAGCAGCUG Stem loop:
(SEQ ID NO: 148)
CGGCUGGACAGCGGGCAACGGAAUCCCAAAAGCAGCUGUUGUCUCCAGAG

CAUUCCAGCUGCGCUUGGAUUUCGUCCCCUGCUCUCCUGCCU miR-99b (MIMAT0000689):
Mature:
(SEQ ID NO: 149)
CACCCGUAGAACCGACCUUGCG Stem loop:
(SEQ ID NO: 150)
GGCACCCACCCGUAGAACCGACCUUGCGGGGCCUUCGCCGCACACAAGCU

CGUGUCUGUGGGUCCGUGUC miR-574-5p (MIMAT0004795):
Mature:
(SEQ ID NO: 151)
UGAGUGUGUGUGUGUGAGUGUGU Stem loop:
(SEQ ID NO: 152)
GGGACCUGCGUGGGUGCGGGCGUGUGAGUGUGUGUGUGUGAGUGUGUGUC

GCUCCGGGUCCACGCUCAUGCACACACCCACACGCCCACACUCAGG miR-151-5p (MIMAT0004697):
Mature:
(SEQ ID NO: 153)
UCGAGGAGCUCACAGUCUAGU Stem loop:
(SEQ ID NO: 154)
UUUCCUGCCCUCGAGGAGCUCACAGUCUAGUAUGUCUCAUCCCCUACUAG

ACUGAAGCUCCUUGAGGACAGGGAUGGUCAUACUCACCUC miR-193a-5p (MIMAT0004614):
Mature:
(SEQ ID NO: 155)
UGGGUCUUUGCGGGCGAGAUGA Stem loop:
(SEQ ID NO: 156)
CGAGGAUGGGAGCUGAGGGCUGGGUCUUUGCGGGCGAGAUGAGGGUGUCG

GAUCAACUGGCCUACAAAGUCCCAGUUCUCGGCCCCCG miR-1246 (MIMAT0005898):
Mature:
(SEQ ID NO: 157)
AAUGGAUUUUUGGAGCAGG Stem loop:
(SEQ ID NO: 158)
UGUAUCCUUGAAUGGAUUUUUGGAGCAGGAGUGGACACCUGACCCAAAGG

AAAUCAAUCCAUAGGCUAGCAAU miR-877 (MIMAT0004949):
Mature:
(SEQ ID NO: 159)
GUAGAGGAGAUGGCGCAGGG Stem loop:
(SEQ ID NO: 160)
GUAGAGGAGAUGGCGCAGGGGACACGGGCAAAGACUUGGGGGUUCCUGGG

ACCCUCAGACGUGUGUCCUCUUCUCCCCUCCCCAG miR-940 (MIMAT0004983):
Mature:
(SEQ ID NO: 161)
AAGGCAGGGCCCCCGCUCCCC Stem loop:
(SEQ ID NO: 162)
GUGAGGUGUGGGCCCGGCCCCAGGAGCGGGGCCUGGGCAGCCCCGUGUGU

UGAGGAAGGAAGGCAGGGCCCCCGCUCCCCGGGCCUGACCCCAC miR-1281 (MIMAT0005939):
Mature:
(SEQ ID NO: 163)
UCGCCUCCUCCUCUCCC Stem loop:
(SEQ ID NO: 164)
AGGGGGCACCGGGAGGAGGUGAGUGUCUCUUGUCGCCUCCUCCUCUCCCC

CCUU miR-494 (MIMAT0002816):
Mature:
(SEQ ID NO: 165)
UGAAACAUACACGGGAAACCUC

Stem loop:
(SEQ ID NO: 166)
GAUACUCGAAGGAGAGGUUGUCCGUGUUGUCUUCUCUUUAUUUAUGAUGA

AACAUACACGGGAAACCUCUUUUUUAGUAUC miR-125b-2* (MIMAT0004603):
Mature:
(SEQ ID NO: 167)
UCACAAGUCAGGCUCUUGGGAC -continued Stem loop:
(SEQ ID NO: 168)
ACCAGACUUUUCCUAGUCCCUGAGACCCUAACUUGUGAGGUAUUUUAGUA

ACAUCACAAGUCAGGCUCUUGGGACCUAGGCGGAGGGGA miR-210 (MIMAT0000267):
Mature:
(SEQ ID NO: 169)
CUGUGCGUGUGACAGCGGCUGA Stem loop:
(SEQ ID NO: 170)
ACCCGGCAGUGCCUCCAGGCGCAGGGCAGCCCCUGCCCACCGCACACUGC

GCUGCCCCAGACCCACUGUGCGUGUGACAGCGGCUGAUCUGUGCCUGGGC

AGCGCGACCC miR-1249 (MIMAT0005901):
Mature:
(SEQ ID NO: 171)
ACGCCCUUCCCCCCCUUCUUCA Stem loop:
(SEQ ID NO: 172)
GGGAGGAGGGAGGAGAUGGGCCAAGUUCCCUCUGGCUGGAACGCCCUUCC

CCCCCUUCUUCACCUG miR-874 (MIMAT0004911):
Mature:
(SEQ ID NO: 173)
CUGCCCUGGCCCGAGGGACCGA Stem loop:
(SEQ ID NO: 174)
UUAGCCCUGCGGCCCCACGCACCAGGGUAAGAGAGACUCUCGCUUCCUGC

CCUGGCCCGAGGGACCGACUGGCUGGGC miR-23a* (MIMAT0004496):
Mature:
(SEQ ID NO: 175)
GGGGUUCCUGGGGAUGGGAUUU Stem loop:
(SEQ ID NO: 176)
GGCCGGCUGGGGUUCCUGGGGAUGGGAUUUGCUUCCUGUCACAAAUCACA

UUGCCAGGGAUUUCCAACCGACC miR-30b* (MIMAT0004589):
Mature:
(SEQ ID NO: 177)
CUGGGAGGUGGAUGUUUACUUC Stem loop:
(SEQ ID NO: 178)
ACCAAGUUUCAGUUCAUGUAAACAUCCUACACUCAGCUGUAAUACAUGGA

UUGGCUGGGAGGUGGAUGUUUACUUCAGCUGACUUGGA miR-296-5p (MIMAT0000690):
Mature:
(SEQ ID NO: 179)
AGGGCCCCCCCUCAAUCCUGU Stem loop:
(SEQ ID NO: 180)
AGGACCCUUCCAGAGGGCCCCCCCUCAAUCCUGUUGUGCCUAAUUCAGAG

GGUUGGGUGGAGGCUCUCCUGAAGGGCUCU miR-744 (MIMAT0004945):
Mature:
(SEQ ID NO: 181)
UGCGGGGCUAGGGCUAACAGCA Stem loop:
(SEQ ID NO: 201)
UUGGGCAAGGUGCGGGGCUAGGGCUAACAGCAGUCUUACUGAAGGUUUCC

UGGAAACCACGCACAUGCUGUUGCCACUAACCUCAACCUUACUCGGUC miR-197 (MIMAT0000227):
Mature:
(SEQ ID NO: 182)
UUCACCACCUUCUCCACCCAGC Stem loop:
(SEQ ID NO: 183)
GGCUGUGCCGGGUAGAGAGGGCAGUGGGAGGUAAGAGCUCUUCACCCUUC

ACCACCUUCUCCACCCAGCAUGGCC miR-27b* (MIMAT0004588):
Mature:
(SEQ ID NO: 184)
AGAGCUUAGCUGAUUGGUGAAC Stem loop:
(SEQ ID NO: 185)
ACCUCUCUAACAAGGUGCAGAGCUUAGCUGAUUGGUGAACAGUGAUUGGU

UUCCGCUUUGUUCACAGUGGCUAAGUUCUGCACCUGAAGAGAAGGUG miR-324-3p* (MIMAT0000762):
Mature:
(SEQ ID NO: 186)
ACUGCCCCAGGUGCUGCUGG Stem loop:
(SEQ ID NO: 187)
CUGACUAUGCCUCCCCGCAUCCCCUAGGGCAUUGGUGUAAAGCUGGAGAC

CCACUGCCCCAGGUGCUGCUGGGGGUUGUAGUC miR-126 (MI0000471):
Mature:
(SEQ ID NO: 188)
CAUUAUUACUUUUGGUACGCG Stem loop:
(SEQ ID NO: 189)
CGCUGGCGACGGGACAUUAUUACUUUUGGUACGCGCUGUGACACUUCAAA

CUCGUACCGUGAGUAAUAAUGCGCCGUCCACGGCA miR-34a (MI0000268)
Mature:
(SEQ ID NO: 190)
AACAUUCAACGCUGUCGGUGAGU Stem loop:
(SEQ ID NO: 191)
GGCCAGCUGUGAGUGUUUCUUUGGCAGUGUCUUAGCUGGUUGUUGUGAGC

AAUAGUAAGGAAGCAAUCAGCAAGUAUACUGCCCUAGAAGUGCUGCACGU

UGUGGGGCCC miR-34b (MI0000742)
Mature:
(SEQ ID NO: 192)
UAGGCAGUGUCAUUAGCUGAUU

Stem loop:
(SEQ ID NO: 193)
GUGCUCGGUUUGUAGGCAGUGUCAUUAGCUGAUUGUACUGUGGUGGUUAC

AAUCACUAACUCCACUGCCAUCAAAACAAGGCAC miR-34c (MI0000743)
Mature:
(SEQ ID NO: 194)
AGGCAGUGUAGUUAGCUGAUUGC -continued Stem loop:
(SEQ ID NO: 195)
AGUCUAGUUACUAGGCAGUGUAGUUAGCUGAUUGCUAAUAGUACCAAUCA

CUAACCACACGGCCAGGUAAAAGAUU miR-1280 (MI0006437)
Mature:
(SEQ ID NO: 196)
UCCCACCGCUGCCACCC Stem loop:
(SEQ ID NO: 197)
UCUGUCCCACCGCUGCCACCCUCCCCUCUGCCUCAGUGUGCCAGGCAUCA

GCACUCACUCACAGAGGCAGGCUGGAUGGCGGGUGGGACAACAG

MicroRNA inhibitors or nucleic acids encoding miRs (such as nucleic acid constructs, for example, vectors) can be administered in any number of ways including, without limitation, by nanopiece, via direct injection into a chondrosarcoma, or via intravenous administration.

The methods disclosed herein can be used to treat any form of chondrosarcoma, including, without limitation, conventional chondrosarcoma, periosteal chondrosarcoma, mesenchymal chondrosarcoma, dedifferentiated chondrosarcoma, clear-cell chondrosarcoma, or extraskeletal myxoid chondrosarcoma. In other embodiments, the methods for treating chondrosarcoma disclosed herein can further include administration of one or more additional anti-cancer therapies to the individual (for example, surgical ablation of the chondrosarcoma). The individual is preferably a mammal in need of such treatment, e.g., a subject that has been diagnosed with chondrosarcoma or a predisposition thereto. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, mammal is a human.

In other aspects, the invention provides a method for diagnosing an individual with chondrosarcoma by assessing the expression level of one or more miR(s) present in a biological sample obtained from the individual selected from miR-199a-3p, miR-26a, miR-762, miR-125a-5p, miR-let-7g, miR-16, miR-let-7f, miR-21, miR-let-7a, miR-638, miR-23a, miR-92a, miR-15b, miR-23b, miR-451, miR-483-5p, miR-15a, miR-27a, miR-26b, miR-let-7d, miR-27-b, miR-98, miR-145, miR-143, miR-1915, miR-149*, miR-7i, miR-7c, miR-7e, miR-936, miR-let-7b, miR-30c, miR-181d, miR-148a, miR-181c, miR-196a, miR-30a, miR-214, miR-187*, miR-663, miR-146a, miR-30d, miR-365, miR-424, miR-1231, miR-424*, miR-454, miR-455-5p, miR-337-3p, miR-381, miR-181a, and miR-30e. In one embodiment, the individual is diagnosed with chondrosarcoma if the expression levels of one or more of the miRs listed above are expressed at a higher level versus that of the corresponding miR(s) in a sample obtained from an individual without chondrosarcoma.

In yet other aspects, provided herein are methods for diagnosing an individual with chondrosarcoma by assessing the expression level of one or more miR(s) present in a biological sample obtained from the individual selected from miR-320c, miR-320b, miR-320a, miR-127-3p, miR-1260, miR-140-3p, miR-22, miR-146b-5p, miR-107, miR-320d, miR-423-5p, miR-1974, miR-455-3p, miR-193b*, miR-103, miR-432, miR-151-3p, miR-31, miR-664*, miR-486-5p, miR-99a, miR-24, miR-191, miR-99b, miR-574-5p, miR-151-5p, miR-193a-5p, miR-1246, miR-877, miR-940, miR-1281, miR-494, miR-125-b-2*, miR-210, miR-1249, miR-874, miR-23a*, miR-30b*, miR-296-5p, miR-744, miR-197, miR-27b*, miR-34a, miR-34b, miR-34c, miR-126, miR-1280, and miR-324-3p. In one embodiment, the individual is diagnosed with chondrosarcoma if the expression levels of one or more of the miRs listed above are expressed at a decreased level compared to that of the corresponding miR(s) in a sample obtained from an individual without chondrosarcoma or in normal tissue from an individual with chondrosarcoma.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF DESCRIPTION OF THE DRAWINGS

FIG. 14A shows a xenograft tumor in mouse injected with molecular beacon for GAPDH mRNA alone or in combination with nanopieces. FIG. 14B depicts miR-181a expression measured by qPCR in xenograft tumors treated with local injection of control miR or anti-miR-181a. delivered by nanopieces. FIG. 14C shows the effect on MMP1 expression as measured by ELISA.

DETAILED DESCRIPTION

Figure 1:
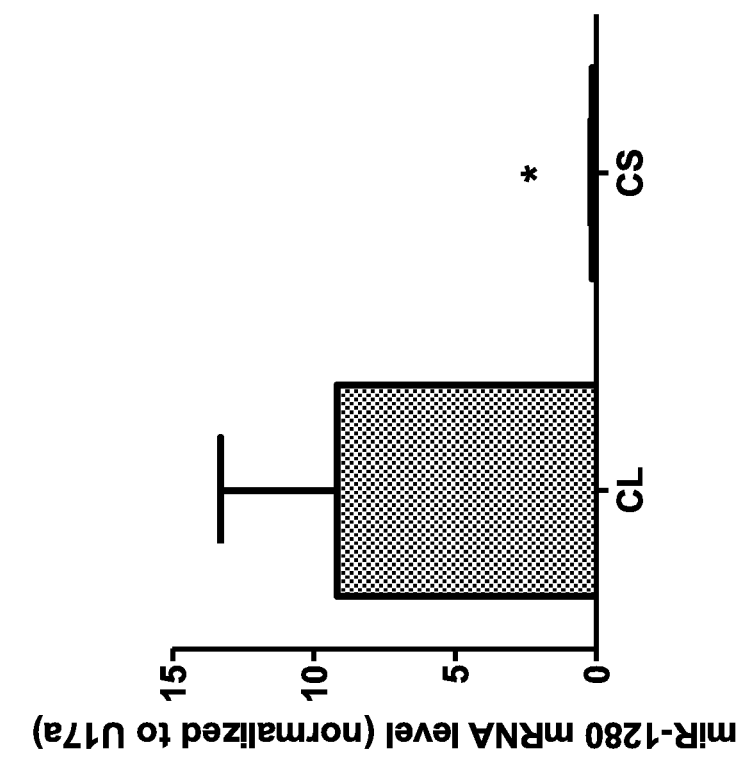
FIG. 1 depicts a graph showing miR-1280 RNA levels as measured by qRT-PCR in normal cartilage and chondrosarcoma tissue.

MicroRNAs (miRs) are small (about 22-nucleotide) RNAs that are derived from larger pre-mfrs. MiRs act as repressors of target mRNAs by promoting their degradation, when their sequences are perfectly complementary or inhibiting translation when their sequences contain mismatches. MicroRNAs are emerging as important regulators of cellular differentiation, their importance underscored by the fact that they are often dysregulated during carcinogenesis. Under a standardized nomenclature system, capitalized "miR-" refers to the mature form of the miRNA, while the uncapitalized "mir-" refers to the pre-miRNA, and "MIR" refers to the gene that encodes them.

Multiple species of miRs were found to be either underexpressed or overexpressed in chondrosarcoma cells in comparison to the expression of these miRs in normal chondrocytes. As such, the compositions and methods provided herein are directed to restoring normal miR expression in individuals with chondrosarcoma, thereby providing an alternative or an adjuvant-based treatment for this particularly radiation- and chemotherapy-resistant neoplasm. Thus, use of the methods and compositions disclosed herein can not only lead to earlier diagnosis of chondrosarcoma, but can also minimize or eliminate the need for disfiguring surgery for successful treatment of this disease.

I. Definitions

As used herein, "adjuvant-based therapy" or "adjuvant-based cancer treatment" refers to additional treatment (e.g., chemotherapy, radiotherapy), usually given after a primary treatment such as surgery (e.g., surgery for chondrosarcoma), where all detectable disease has been removed, but where there remains a statistical risk of relapse due to occult disease. Typically, statistical evidence is used to assess the risk of disease relapse before deciding on a specific adjuvant-based therapy. The aim of adjuvant treatment is to improve disease-specific and overall survival. Because the treatment is essentially for a risk, rather than for provable disease, it is accepted that a proportion of patients who receive adjuvant therapy will already have been cured by their primary surgery. The primary goal of adjuvant chemotherapy is to control systemic relapse of a disease to improve long-term survival. Adjuvant radiotherapy is given to control local and/or regional recurrence.

An "individual" can be a vertebrate, a mammal, or a human. Mammals include, but are not limited to, farm animals, sport animals, pets, primates, mice and rats. In one aspect, an individual is a human. An "individual in need thereof" refers to an individual diagnosed with or thought to have chondrosarcoma. An individual can be diagnosed with chondrosarcoma using any means known in the art including, without limitation, radiographs ("x-rays"), computerized tomography (CT), technesium bone scan, PET scan, and magnetic resonance imaging (MRI) (see Leddy et al., Cancer Treat Res. 2014; 162:117-30; Qasem et al. Semin Diagn Pathol. 2014 January; 31(1):10-20).

By the phrases "therapeutically effective amount," "in an amount effective" and "effective dosage" is meant an amount sufficient to produce a therapeutically (e.g., clinically) desirable result; the exact nature of the result will vary depending on the nature of the disorder being treated. For example, where the disorder to be treated is chondrosarcoma, the result can be inhibition of growth of chondrosarcoma cells and shrinkage of chondrosarcoma tumors. Therapeutically effective amount can also refer to the amount sufficient to decrease invasion or metastasis of chondrosarcoma (such as a decrease in invasion or metastasis by any of about 10%, 20%, 30%, 40%, 50%, 60%, 70%, 80%, 90%, or 100%, inclusive of values falling in between these percentages). The compositions described herein can be administered from one or more times per day to one or more times per week. A person having ordinary skill in the art will appreciate that certain factors can influence the dosage and timing required to effectively treat an individual, including but not limited to the severity of the disease or disorder, previous treatments, the general health and/or age of the individual, and other diseases present. Moreover, treatment of an individual with a therapeutically effective amount of the compositions of the invention can include a single treatment or a series of treatments. The effective amount is generally determined by the physician on a case-by-case basis and is within the skill of one in the art.

"Purified," as used herein, refers to molecules, either nucleic acid or amino acid sequences, that are removed from their natural environment and isolated or separated from at least one other component with which they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless defined otherwise herein, all technical and scientific terms used herein have the same meaning as commonly understood by one of ordinary skill in the art to which this invention pertains.

As used herein, the term "about" in the context of a numerical value or range means ±10% of the numerical value or range recited or claimed.

As used herein, the singular terms "a," "an," and "the" include the plural reference unless the context clearly indicates otherwise.

II. Methods of the Invention

Chondrosarcoma accounts for about 20% of primary malignant bone tumors, and shows the second highest occurrence frequency following that of osteosarcoma. It is histologically classified into conventional chondrosarcoma, periosteal chondrosarcoma, mesenchymal chondrosarcoma, dedifferentiated chondrosarcoma, clear-cell chondrosarcoma, extraskeletal myxoid chondrosarcoma, and the like. Typical chondrosarcoma frequently occurs in individuals aged 30 to 50, and slightly more frequently occurs in men. It tends to appear in the pelvic bone, but also regularly occurs in rib, proximal femur, proximal humerus, and distal femur. Mesenchymal chondrosarcoma usually occurs in persons from between the age of 10 and 19 but is also observed in people in their 30's. Mesenchymal chondrosarcoma frequently occurs in jaw, spine, iliac bone, rib, and the distal part of the femur. Dedifferentiated chondrosarcoma is a combination of a spindle cell sarcoma and benign or low-grade cartilage tumor. which can develop from conventional chondrosarcoma or benign cartilaginous tumors such as enchondroma. It occurs in individuals in their 50's or 60's, and most frequently occurs in femur but is also observed in pelvis and humerus. Clear-cell chondrosarcoma frequently occurs in persons in their 20's to 50's, and in about ⅔ of the patients, it occurs in the humeral head or femoral head. It also occurs in cranial bone, spine, and the bones of hand and foot. Extraskeletal myxoid chondrosarcoma frequently occurs in people in their 40's and 50's, and may occur in soft tissues of extremities such as thigh, as well as the distal portions of extremities, the mediastinum and the retroperitoneum.

Nearly all chondrosarcoma patients appear to be in good health. Often, patients are not aware of a growing sarcoma until there is a noticeable lump or pain. Earlier diagnosis is generally accidental, when a patient undergoes testing for another problem and physicians discover the cancer. Prognosis depends on how early the cancer is discovered and treated. For the least aggressive grade, about 90% of patients survive more than five years after diagnosis. People usually have a good survival rate at the low grade volume of cancer. However, for the most aggressive grade, only 10% of patients will survive one year.

Surgery is currently the main form of treatment for chondrosarcoma. Musculoskeletal tumor specialists or orthopedic oncologists are usually chosen to treat chondrosarcoma, unless it is located in the skull, spine, or chest cavity, in which case, a neurosurgeon or thoracic surgeon experienced with sarcomas is chosen. Often, a limb-sparing operation can be performed; however in some cases amputation is unavoidable. Amputation of the arm, leg, jaw, or half of the pelvis (called a hemipelvectomy) may be necessary in some cases.

A. Methods for Treating Chondrosarcoma

The present invention is directed, inter alia, to methods for inhibiting the symptoms or conditions (disabilities, impairments) associated chondrosarcoma as described in detail below. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for the condition, but rather, can encompass a result which includes reducing or preventing the symptoms that result from chondrosarcoma, reducing or preventing the occurrence of such symptoms (either quantitatively or qualitatively), reducing the severity of such symptoms or physiological effects thereof, and/or enhancing the recovery of the individual after experiencing chondrosarcoma symptoms.

Specifically, the therapies of the present invention, when administered to an individual, can treat or prevent one or more of the symptoms or conditions associated with chondrosarcoma and/or reduce or alleviate symptoms of or conditions associated with this disorder. As such, protecting an individual from the effects or symptoms resulting from chondrosarcoma includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present invention as compared to those that have not. In some embodiments, a positive or beneficial difference is a reduction in tumor size following treatment, such as a decrease of any of about 5%, 10%, 15%, 20%, 25%, 30%, 35%, 40%, 45%, 50%, 55%, 60%, 65%, 70%, 75%, 80%, 85%, 90%, 95%, or 100% in tumor size or weight, inclusive of values falling in between these percentages. In some embodiments, a positive or beneficial difference is prevention or a delay in the occurrence of metastatic disease, which is most commonly to the lungs, but can also be to other organs, including the skeleton. In some embodiments, a positive or beneficial difference is reduction in size of metastases or a decrease in rate of growth, such as a decrease of any of about 5%, 10%, 15%, 20%, 25%, 30%, 35%, 40%, 45%, 50%, 55%, 60%, 65%, 70%, 75%, 80%, 85%. 90%, 95%, or 100% in tumor size, or weight, inclusive of values falling in between these percentages.

The methods of the invention may be practiced in an adjuvant setting. "Adjuvant setting" refers to a clinical setting in which an individual has had a history of a proliferative disease, particularly a chondrosarcoma and generally (but not necessarily) has been responsive to therapy, which includes, but is not limited to, surgery, radiotherapy, and chemotherapy. However, because of a history of the proliferative disease (such as a chondrosarcoma), these individuals are considered at risk of developing a recurrence of that disease. In some embodiments, treatment or administration in the "adjuvant setting" refers to a subsequent mode of treatment.

The methods provided herein may also be practiced in a "neoadjuvant setting," that is, the method may be carried out before the primary/definitive therapy. In some aspects, the individual has previously been treated. In other aspects, the individual has not previously been treated. In some aspects, the treatment is a first line therapy. The individual may be a human or may be a non-human mammal.

1. Inhibition of miR Expression

Provided herein are methods for treating an individual with chondrosarcoma by administering to the individual a therapeutically effective amount of an inhibitor of one or more microRNA (miR) selected from the group consisting of miR-199a-3p, miR-26a, miR-762, miR-125a-5p, miR-let-7g, miR-16, miR-let-7f, miR-21, miR-let-7a, miR-638, miR-23a, miR-92a, miR-15b, miR-23b, miR-451, miR-483-5p, miR-15a, miR-27a, miR-26b, miR-let-7d, miR-27-b, miR-98, miR-145, miR-143, miR-1915, miR-149*, miR-7i, miR-7c, miR-7e, miR-93b, miR-let-7b, miR-30c, miR-181d, miR-148a, miR-181c, miR-196a, miR-30a, miR-214, miR-187*, miR-663, miR-146a, miR-30d, miR-365, miR-424, miR-1231, miR-424*, miR-454, miR-455-5p, miR-337-3p, miR-381, miR-let-7a-2*, miR-126, miR-181a, and miR-30e.

Suitable compounds for inhibiting miR gene expression include double-stranded RNA (such as short- or small-interfering RNA or "siRNA"), antagomirs, antisense nucleic acids, enzymatic RNA molecules such as ribozymes, or molecules capable of forming a triple helix with the miR gene. Another class of inhibitor compound can cause hypermethylation of the miR gene product promoter, resulting in reduced expression of the miR gene. Each of these compounds can be targeted to a given miR gene product to inhibit (e.g., destroy, induce the destruction of, or otherwise reduce the level of) the target miR.

For example, expression of a given miR can be inhibited by inducing RNA interference of the miR with an isolated double-stranded RNA ("dsRNA") molecule which has at least 90%, for example at least about 91%, 92%, 93%, 94%, 95%, 96%, 97%, 98%, 99%, or 100% sequence homology with at least a portion of the miR. In a particular embodiment, the dsRNA molecule is a "short or small interfering RNA" or "siRNA." siRNA useful in the present methods comprise short double-stranded RNA from about 17 nucleotides to about 29 nucleotides in length, or from about 19 to about 25 nucleotides in length. siRNAs have a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miR gene product. As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides. Further, the siRNA can also be engineered to contain certain "drug like" properties. Such modifications include chemical modifications for stability and cholesterol conjugation for delivery. Such modifications impart better pharmacological properties to the siRNA and using such modifications, pharmacologically active siRNAs can achieve broad biodistribution and efficient silencing of miRNAs in most tissues in vivo.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. :In one embodiment, the 3' overhang is present on both strands of the siRNA, and is 2 nucleotides in length. For example, each strand of the siRNA can comprise 3' overhangs of dithymidylic acid ("TT") or diuridylic acid ("uu").

siRNA can be produced chemically or biologically, or can be expressed from a recombinant plasmid or viral vector, as described above for the isolated miR gene products. Exemplary methods for producing and testing dsRNA or siRNA molecules are described in U.S. Patent Application Publication Nos. 2002/0173478 and 2004/0018176, the disclosures of which are incorporated herein by reference.

In another aspect, one or more antagomirs can be used to inhibit a microRNA in the methods of the disclosed invention. Antagomirs are single stranded, double stranded, partially double stranded and hairpin-structured chemically-modified oligonucleotides that specifically target a microRNA. Antagomirs have at least 12 or more contiguous nucleotides substantially complementary to an endogenous miRNA or pre-miRNA (stem-loop) nucleotide sequence. As used herein, "partially double stranded" refers to double stranded structures that contain less nucleotides than the complementary strand. An antagomir typically includes a nucleotide sequence sufficiently complementary to hybridize to a miRNA target sequence of about 12 to 25 nucleotides, (such as about 15 to 23 nucleotides, or any of about 12, 13, 14, 15, 16, 17, 18, 19, 20, 21, 22, 23, 24, or 25 nucleotides). Ideally, the target sequence differs by no more than 1, 2, or 3 nucleotides from the complementary antagomir sequence. Delivery of antagomirs is often facilitated by the attachment of a moiety that promotes cellular diffusion and transport. For example, the antagomir can include a non-nucleotide moiety, e.g., a cholesterol moiety. The non-nucleotide moiety can be attached, e.g., to the 3' or 5' end of the antagomir.

Antagomirs can be further stabilized against nucleolytic degradation such as by the incorporation of a modification, e.g., a nucleotide modification. For example, the antagomir can include a phosphorothioate moiety at the first, second, or third internucleotide linkage at the 5' or 3' end of the nucleotide sequence. In another non-limiting embodiment, the antagomir includes a 2'-modified nucleotide, e.g., a 2'-deoxy, 2'-deoxy-2'-fluoro, 2'-O-methyl, 2'-O-methoxyethyl (2'-O-M0E), 2'-O-aminopropyl (2'-O-AP), 2'-O-dimethylaminoethyl (2'-O-DMAOE), 2'-O-dimethylaminopropyl (2'-O-DMAP), dimethylaminoethyloxyethyl (2'-O-DMAEOE), or 2'-O-N-methylacetamido (2'-O-NMA). In other embodiments, the antagomir includes at least one 2'-O-methyl-modified nucleotide, and in some embodiments, all of the nucleotides of the antagomir include a 2'-O-methyl modification. Methods for synthesizing and validating a therapeutically effective antagomir engineered to silence miRNAs in vivo is described in Krutzfeldt J, et al. (2005), Silencing of microRNAs in vivo with 'antagomirs,' Nature 438(7068):685-9, the entire content of which is incorporated herein by reference.

Expression of a given miR gene can also be inhibited by an antisense nucleic acid. As used herein, an "antisense nucleic acid" refers to a nucleic acid molecule that stably binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary, such as any of about 55%, 60%, 65%, 70%, 75%, 80%, 85%, 90%, or 100% complementary to a contiguous nucleic acid sequence in a miR. Without wishing to be bound by any theory, it is believed that the antisense nucleic acids activate RNase H or another cellular nuclease that digests the miR gene product/antisense nucleic acid duplex.

For example, in eukaryotes, RNA polymerase catalyzes the transcription of a structural gene to produce mRNA. A DNA molecule can be designed to contain an RNA polymerase template in which the RNA transcript has a sequence that is complementary to that of a preferred mRNA. The RNA transcript is termed an "antisense RNA". Antisense RNA molecules can inhibit mRNA expression (for example, Rylova et al., Cancer Res, 62(3):801-8, 2002; Shim et al., Int. J. Cancer, 94(1):6-15, 2001). Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups. Antisense nucleic acids can be produced chemically or biologically, or can he expressed from a recombinant plasmid or viral vector, as described above for the isolated miR gene products. Exemplary methods for producing and testing are within the skill in the art; see, e.g., Stein and Cheng (1993), Science 261:1004 and U.S. Pat. No. 5,849,902 to Woolf et al., the entire disclosures of which are incorporated herein by reference.

Expression of a given miR can also be inhibited by an enzymatic nucleic acid. As used herein, an "enzymatic nucleic acid" refers to a nucleic acid comprising a substrate binding region that has complementarity to a contiguous nucleic acid sequence of a miR, and which is able to specifically cleave the miR. The enzymatic nucleic acid substrate binding region can be, for example, 50-100% complementary, 75-100% complementary, or 95-100%, such as any of about 55%, 60%, 65%, 70%, 75%, 80%, 85%, 90%, or 100% complementary to a contiguous nucleic acid sequence in an miR. The enzymatic nucleic acids can also comprise modifications at the base, sugar, and/or phosphate groups. An exemplary enzymatic nucleic acid for use in the present methods is a ribozyme.

Ribozymes are enzymatic RNA molecules capable of catalyzing the specific cleavage of RNA. A review is provided in Rossi, Current Biology, 4:469-471 (1994). The mechanism of ribozyme action involves sequence-specific hybridization of the ribozyme molecule to complementary target RNA, followed by an endonucleolytic cleavage. A composition of ribozyme molecules must include one or more sequences complementary to the target gene mRNA, and must include a well-known catalytic sequence responsible for mRNA cleavage (U.S. Pat. No. 5,093,246, incorporated by reference herein). Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the miR gene containing the cleavage site can be evaluated for predicted structural features, for example, secondary structure, that can render an oligonucleotide sequence unsuitable. The suitability of candidate sequences also can be evaluated by testing their accessibility to hybridization with complementary oligonucleotides, using ribonuclease protection assays.

Enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), Nucl. Acids Res. 23:2092-96; Hammann et al. 1999), Antisense and Nucleic Acid Drug Dev. 9:25-31; and U.S. Pat. No. 4,987,071 to Cech et al, the entire disclosures of which are incorporated herein by reference.

Triple helix forming molecules can be used in reducing the level of a target miR. Nucleic acid molecules that can associate together in a triple-stranded conformation (triple helix) and that thereby can be used to inhibit translation of a target gene, should he single helices composed of deoxynucleotides. The base composition of these oligonucleotides must be designed to promote triple helix formation via Hoogsteen base pairing rules, which generally require sizeable stretches of either purines or pyrimidines on one strand of a duplex. Nucleotide sequences can be pyrimidine-based, which will result in TAT and CCC triplets across the three associated strands of the resulting triple helix. The pyrimidine-rich molecules provide bases complementary to a purine -rich region of a single strand of the duplex in a parallel orientation to that strand. In addition, nucleic acid molecules can be chosen that are purine-rich, for example, those that contain a stretch of G residues. These molecules will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines on one strand of a duplex.

In some embodiments, inhibition of one or more microRNA (miR) selected from the group consisting of miR-199a-3p, miR-26a, miR-762, miR-125a-5p, miR-let-7g, miR-16, miR-let-7f, miR-21, miR-let-7a, miR-638, miR-23a, miR-92a, miR-15b, miR-23b, miR-451, miR-483-5p, miR-15a, miR-27a, miR-26b, miR-let-7d, miR-27-b, miR-98, miR-145, miR-143, miR-1915, miR-149*, miR-7i, miR-7c, miR-7e, miR-93b, miR-let-7b, miR-30c, miR-181d, miR-148a, miR-181c, miR-196a, miR-30a, miR-214, miR-187*, miR-663, miR-146a, miR-30d, miR-365, miR-424, miR-1231, miR-424*, miR-454, miR-455-5p, miR-337-3p, miR-381, miR-let-7a-2*, miR-181a, and miR-30e according to any of the methods disclosed herein results in decreased chondrosarcoma progression (tumor weight or size compared to tumors that are not treated with inhibitors of the one or more miRs, or delay in onset or progression of metastatic disease). The reduction in progression can be any of about 10%, 20%, 30%, 40%, 50%, 60%, 70%, 80%, 90%, or 100%, inclusive of values falling in between these percentages. In some embodiments, the miR inhibitor is an inhibitory nucleic acid such as, but not limited to, an antisense oligonucleotide or an siRNA. In other embodiments, the inhibitor is delivered to the chondrosarcoma cell by a nanopiece. In one embodiment, the miR inhibitor is an inhibitor of miR-181a. In a further embodiment, the miR inhibitor (such as miR-181a) is co-administered with a chemotherapeutic (such as, but not limited to AMD3100). In some embodiments, the treatment occurs under normoxic conditions. In other embodiments, the treatment occurs under hypoxic conditions.

In further embodiments, inhibition of one or more microRNA (miR) selected from the group consisting of miR-199a-3p, miR-26a, miR-762, miR-125a-5p, miR-let-7g, miR-16, miR-let-7f, miR-21, miR-let-7a, miR-638, miR-23a, miR-92a, miR-15b, miR-23b, miR-451, miR-483-5p, miR-15a, miR-27a, miR-26b, miR-let-7d, miR-27-b, miR-98, miR-145, miR-143, miR-1915, miR-149*, miR-7i, miR-7c, miR-7e, miR-93b, miR-let-7b, miR-30c, miR-181d, miR-148a, miR-181c, miR-196a, miR-30a, miR-214, miR-187*, miR-663, miR-146a, miR-30d, miR-365, miR-424, miR-1231, miR-424*, miR-454, miR-455-5p, miR-337-3p, miR-381, miR-let-7a-2*, miR-181a, and miR-30e according to any of the methods disclosed herein results in decreased expression of matrix metalloproteinase (MMP) (such as, but not limited to, MMP1), vascular endothelial growth factor (VEGF), or other molecules related to tumor growth and or metastasis, by chondrosarcoma cells compared to expression of molecules in cells that are not treated with inhibitors of the one or more miRs. The reduction in expression of MMP and other molecules can be any of about 10%, 20%, 30%, 40%, 50%, 60%, 70%, 80%, 90%, or 100%, inclusive of values falling in between these percentages. In some embodiments, the miR inhibitor is an inhibitory nucleic acid such as, but not limited to, an antisense oligonucleotide or an siRNA. In other embodiments, the inhibitor is delivered to the chondrosarcoma cell by a nanopiece. In one embodiment, the miR inhibitor is an inhibitor of miR-181a.

2. Restoration of miR Expression

In other aspects, provided herein are methods for treating chondrosarcoma in an individual in need thereof. The method is performed by administering to the individual a therapeutically effective amount of a nucleic acid encoding one or more microRNA (miR) selected from the group consisting of miR-320c, miR-320b, miR-320a, miR-127-3p, miR-1260, miR-140-3p, miR-22, miR-146b-5p, miR-107, miR-320d, miR-423-5p, miR-1974, miR-455-3p, miR-193b*, miR-103, miR-432, miR-151-3p, miR-31, miR-664*, miR-486-5p, miR-99a, miR-24, miR-191, miR-99b, miR-574-5p, miR-151-5p, miR-193a-5p, miR-1246, miR-877, miR-940, miR-1281, miR-494, miR-125-b-2*, miR-210, miR-1249, miR-874, miR-23a*, miR-30b*, miR-296-5p, miR-744, miR-197, miR-27b*, miR-34a, miR-34b, miR-34c, miR-126, miR-1280, and miR-324-3p.

The administered microRNA-encoding nucleic acids lead to transient or permanent overexpression of the desired microRNA(s) in the target cell or tissue (such as chondrosarcoma cells). Thus, the nucleic acids increase the level of an endogenous microRNA sequence expressed in a cell or tissue. Similarly, administration of microRNA delivery constructs such as lentiviruses lead to permanent expression of microRNAs (stem-loop sequence or mature sequence) in the cells.

In one embodiment, the administered nucleic acid is a microRNA mimic. As used herein, the term "microRNA mimic" refers to synthetic non-coding RNAs that are capable of entering the RNAi pathway and regulating gene expression. MicroRNA mimics imitate the function of endogenous microRNAs and can be designed as mature, double-stranded molecules or mimic precursors (e.g., pn- or pre-microRNAs). MicroRNA mimics can be comprised of modified or unmodified RNA, DNA, RNA-DNA hybrids or alternative nucleic acid chemistries. Accordingly, the invention provides microRNA mimics corresponding any of the miRs disclosed above which comprise a consensus sequence, wherein the microRNA mimics are capable of mimicking the endogenous activity of any naturally-expressed miR. Therefore, restoration of microRNA expression is achieved through the use of these microRNA mimics.

To improve efficiency, the methods of the presentinvention can employ a microRNA mimic comprising a structurally and chemically modified double-stranded RNA. In exemplary embodiments, non-toxic chemical modifications to the mimic sequence can be introduced to improve stability, reduce off-target effects and increase activity.

In particular embodiments, the microRNA mimics of the invention contemplate the use of nucleotides that are modified to enhance their activities. Such nucleotides include those that are at the 5' or 3' terminus of the RNA as well as those that are internal within the molecule.

In other aspects, modifications may be made to the sequence of a microRNA or a pre-microRNA without disrupting microRNA activity. As used herein, the term "functional variant" of a microRNA sequence refers to an oligonucleotide sequence that varies from the natural microRNA sequence, but retains one or more functional characteristics of the microRNA (e.g. enhancement of cancer cell susceptibility to chemotherapeutic agents, cancer cell proliferation inhibition, induction of cancer cell apoptosis, specific microRNA target inhibition). In some embodiments, a functional variant of a microRNA sequence retains all of the functional characteristics of the microRNA. In certain embodiments, a functional variant of a microRNA has a nucleobase sequence that is a least about 60%, 65%, 70%, 75%, 80%, 85%, 90%, 91%, 92%, 93%, 94%, 95%, 96%, 97%, 98% or 99% identical to the microRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the microRNA or precursor thereof under stringent hybridization conditions. Accordingly, in certain embodiments the nucleotide base sequence of a functional variant may be capable of hybridizing to one or more target sequences of the microRNA. Other modifications contemplated in the practice of the invention can be found in U.S. Patent Application Publication No. 2012/0259001, which is incorporated herein by reference in its entirety In some embodiments, administering to an individual (such as, for example, intravenous, intratumoral, or parentral administration) a therapeutically effective amount (e.g., from about 1 ng/kg to about 100 ng/kg of body weight) of a nucleic acid encoding one or more microRNA (miR) selected from the group consisting of miR-320c, miR-320b, miR-320a, miR-127-3p, miR-1260, miR-140-3p, miR-22, miR-146b-5p, miR-107, miR-320d, miR-423-5p, miR-1974, miR-455-3p, miR-193b*, miR-103, miR-432, miR-151-3p, miR-31, miR-664*, miR-486-5p, miR-99a, miR-24, miR-191, miR-99b, miR-574-5p, miR-151-5p, miR-193a-5p, miR-1246, miR-877, miR-940, miR-1281, miR-494, miR-125-b-2*, miR-210, miR-1249, miR-874, miR-23a*, miR-30b*, miR-296-5p, miR-744, miR-197, miR-27b*, miR-34a, miR-34b, miR-34c, miR-126, miR-1280, and miR-324-3p results in decreased expression of one or more angiogenesis or metastasis-promoting molecules by chondrosarcoma cells. These angiogenesis or metastasis-promoting molecules can include, without limitation, matrix metalloproteinases (MMP), vascular endothelial growth factor (VEGF), placental growth factor (PGF), thrombospondin-1 (TSP-1) and/or Met. In some embodiments, administration of one or more of the miRs above results in decreased expression of the one or more angiogenesis-promoting molecules by any of about 10%, 20%, 30%, 40%, 50%, 60%, 70%, 80%, 90%, or 100%, inclusive of values falling in between these percentages compared to chondrosarcoma cells that are not administered the one or more miRs. In some embodiments, the one or more miRs are delivered to the chondrosarcoma cell by a nanopiece. In another embodiment, the miR is one or more of miR-126, miR-34a, miR-34b, miR-34c, and/or miR1280.

In other embodiments, administering to an individual (such as, for example, intravenous, intratumoral, or parentral administration) a therapeutically effective amount (e.g., from about 1 ng/kg to about 100 ng/kg of body weight) of a nucleic acid encoding one or more microRNA (miR) selected from the group consisting of miR-320c, miR-320b, miR-320a, miR-127-3p, miR-1260, miR-140-3p, miR-22, miR-146b-5p, miR-107, miR-320d, miR-423-5p, miR-1974, miR-455-3p, miR-193b*, miR-103, miR-432, miR-151-3p, miR-31, miR-664*, miR-486-5p, miR-99a, miR-24, miR-191, miR-99b, miR-574-5p, miR-151-5p, miR-193a-5p, miR-1246, miR-877, miR-940, miR-1281, miR-494, miR-125-b-2*, miR-210, miR-1249, miR-874, miR-23a*, miR-30b*, miR-296-5p, miR-744, miR-197, miR-27b*, miR-34a, miR-34b, miR-34c, miR-126, miR-1280, and miR-324-3p results in decreased proliferation by chondrosarcoma cells. In some embodiments, administration of one or more of the miRs above results in decreased proliferation of chondrosarcoma cells by any of about 10%, 20%, 30%, 40%, 50%, 60%, 70%, 80%, 90%, or 100%, inclusive of values falling in between these percentages compared to chondrosarcoma cells that are not administered the one or more miRs. In some embodiments, the one or more miRs are delivered to the chondrosarcoma cell by a nanopiece. In another embodiment, the miR is one or more of miR-126, miR-34a, miR-34b, miR-34c, and/or miR1280.

3. Delivery of miR Inhibitors and/or Nucleic Acid Constructs

The inhibitors and miR nucleic acid for use in the methods disclosed herein can be introduced into a cell (such as a chondrosarcoma cell) by any method known, e.g., transfection or transduction. Transfection is the process of introducing nucleic acids into cells by non-viral methods, and transduction is the process whereby foreign DNA is introduced into another cell via a viral vector (such as a lentiviral vector or an adenoviral vector). The invention also includes use of nanopieces either de novo or linked with polyethylene glycol (PEG), aptamers, and or peptides to deliver microRNAs and miR inhibitors alone or in combination.

Other methods of administering nucleic acids are well known in the art. In particular, the routes of administration already in use for nucleic acid therapeutics, along with formulations in current use, provide preferred routes of administration and formulation for the nucleic acids. Nucleic acid compositions can he administered by a number of routes including, but not limited to: intratumoral, oral, intravenous, intrapleural, intraperitoneal, intramuscular, transdermal, subcutaneous, topical, sublingual, or rectal means.

In some embodiments, miR inhibitors or miR nucleic acid constructs are administered to an organism using one or more reagents that facilitate or enhance delivery, e.g., a compound which enhances transit through the cell membrane. Such reagents can include, without limitation, a lipophilic moiety; a transfection agent (e.g., an ion or other substance which substantially alters cell permeability to an oligonucleotide agent); or (iii) a commercial transfecting agent such as Lipofectamine™ (Invitrogen, Carlsbad, Calif.), Lipofectamine 2000™, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In other embodiments, the miR inhibitors or miR nucleic acid constructs are administered using a Nanopiece delivery vehicle. Nanopieces are co-assembled rosette nanotubes (RNTs) and nucleic acids (such as an inhibitory nucleic acid, for example, an siRNA). The RNT and the nucleic acid cargo are joined by completely non-covalent bindings. Once Nanopieces deliver their nucleic acid cargo, their degradation products are highly biocompatible due to the biomimetic G^C base motif of the RNT. The ability of Nanopiece to deliver cargo effectively and degrade safely allows minimal levels of cytotoxicity, a prerequisite for in vivo therapeutic applications. Furthermore, Nanopieces have a nano-rod-like shape, 20-30 nm in diameter. This is more than 2000 times smaller in volume than Lipofectamine™ spherical particles, allowing the Nanopiece to transfect cells that are shielded by dense extracellular matrix. Information related to constructing and using nanostructures, e.g., nanopieces, for delivering nucleic acids and other therapeutics to cells can be found in PCT/US2015/020801 (International Patent Application Publication No. WO 2015/139051) and International Patent Application No.: PCT/US2015/061193, the disclosures of which are incorporated by reference herein in its entirety. Exemplary NPs useful in the therapeutic methods described herein include those with a length of 1 nm to 200 nm, e.g. a length of about 100 nm, and a width or diameter of 1 nm to 60 nm, e.g., 20 nm. For example, the length is in the range of 50-150 nm and the width/diameter is in the range of 20-40 nm. Typically, the nanopieces are characterized by a length of about 100 nm and width/diameter of about 20 nm.

In one embodiment, a recombinant vector can be used for delivering one or more miR inhibitor or miR nucleic acid constructs (such as any of those disclosed herein) to the individual. This can include both systemic delivery and delivery localized to a particular region of the body (such as, the location of a chondrosarcoma). Any vector capable of enabling recombinant production of one or more miR inhibitor or miR nucleic acid and/or which can deliver one or more oligo miR inhibitors or miR nucleic acid into a host cell (such as a chondrosarcoma cell). The vector can be either RNA or DNA, either prokaryotic or eukaryotic, and typically is a virus or a plasmid. The vector can be part of a DNA vaccine or used as part of any other method for delivering a heterologous gene for expression in a host cell that is known to one having skill in the art. Recombinant vectors are capable of replicating when transformed into a suitable host cell. Viral vectors infect a wide range of non-dividing human cells and have been used extensively in live vaccines without adverse side effects. A viral vector (such as, but not limited to, an adenoviral vector or an adeno-associated viral (AAV) vector (e.g. AAV-1, AAV-2, AAV-3, AAV-4, AAV-5, AAV-6, etc. or hybrid AAV vectors comprising the same) is an example of a vector for use in the present methods for delivering one or more miR inhibitor or miR nucleic acid constructs to chondrosarcoma cancer cells (see, e.g. U.S. Patent Application Publication No. 2004/0224389, the disclosure of which is incorporated by reference herein).

4. Other Anti-Cancer Therapies

In some aspects, any of the methods of treatment described herein can comprise administering one or more additional anti-cancer therapies to the individual. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating-like agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are vinca alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

In some aspects, the anti-cancer therapeutics can be selected from remicade, docetaxel, celecoxib, melphalan, dexamethasone (Decadron®), steroids, gemcitabine, cis-platinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, or etoposide.

In other embodiments, the anti-cancer therapeutics can be selected from bortezomib, cyclophosphamide, dexamethasone, doxorubicin, interferon-alpha, lenalidomide, melphalan, pegylated interferon-alpha, prednisone, thalidomide, or vincristine.

In other embodiments, the anti-cancer therapeutic is AMD3100 (plerixafor).

B. Methods for Diagnosing Chondrosarcoma

Also provided herein are methods for diagnosing chondrosarcoma in an individual via detecting the expression level of one or more (such as 2, 3, 4, 5, 6, 7, 8 9, 10, 11, 12, 13, 14, 15, 16, 17, 18, 19, 20, 25, 30, 35, 40, 45, or 50) microRNAs (miRs) selected from the group consisting of miR-199a-3p, miR-26a, rniR-762, miR-125a-5p, miR-let-7g, miR-16, miR-let-7f, miR-21, miR-let-7a, miR-638, miR-23a, miR-92a, miR-15b, miR-23b, miR-451, miR-483-5p, miR-15a, miR-27a, miR-26b, miR-let-7d, miR-27-b miR-98, miR-145, miR-143, miR-1915, miR-149*, miR-7i, miR-7c, miR-7e, miR-936, miR-let-7b, miR-30c, miR-181d, miR-148a, miR-181c, miR-196a, miR-30a, miR-214, miR-187*, miR-663, miR-146a, miR-30d, miR-365, miR-424, miR-1231, miR-424*, miR-454, miR-455-5p, miR-337-3p, miR-381, miR-181a, and miR-30e in a biological sample obtained from the individual; wherein the individual is diagnosed with chondrosarcoma if expression of one or more of the miRs is increased relative to the expression level of said one or more miRs in a biological sample obtained from an individual without chondrosarcoma or relative to normal tissue from the individual with chondrosarcoma. In some embodiments, the individual is diagnosed with chondrosarcoma if expression of one or more of the miRs listed above is any of about 10%, 20%, 30%, 40%, 50%, 60%, 70%, 80%, 90%, or 100% increased in the biological sample from the individual relative to the expression level of the corresponding miR(s) from a sample derived from an individual without chondrosarcoma or relative to normal tissue from the individual with chondrosarcoma. In other embodiments, the individual is diagnosed with chondrosarcoma if expression of one or more of the miRs listed above is any of about 2, 3, 4, 5, 6, 7, 8, 9, or 10 fold more highly expressed in the biological sample from the individual relative to the expression level of the corresponding miR(s) from a sample derived from an individual without chondrosarcoma or relative to normal tissue from the individual with chondrosarcoma.

Further, also provided herein is a method for diagnosing chondrosarcoma in an individual by detecting the expression level of one or more (such as 2, 3, 4, 5, 6, 7, 8, 9,10, 11, 12, 13, 14, 15, 16, 17, 18, 19, 20, 25, 30, 35, 40, 45, or 50) miR(s) selected from the. group consisting of miR-320c, miR-320b, miR-320a, miR-127-3p, miR-1260, miR-140-3p, miR-22, miR-146b-5p, miR-107, miR-320d, miR-423-5p, miR-1974, miR-455-3p, miR-193b*, miR-103, miR-432, miR-151-3p, miR-31, miR-664*, miR-486-5p, miR-99a, miR-24, miR-191, miR-99b, miR-574-5p, miR-151-5p, miR-193a-5p, miR-1246, miR-877, miR-940, miR-1281, miR-494, miR-125-b-2*, miR-210, miR-1249, miR-874, miR-23a*, miR-30b*, miR-296-5p, miR-744, miR-197, miR-27b*, miR-34a, miR-34b, miR-34c, miR-126, miR-1280, and miR-324-3p in the biological sample obtained from the individual, wherein the individual is diagnosed with chondrosarcoma if expression of one or more of the miR(s) of is decreased relative to the expression level of said one or more miRs in a biological sample obtained from an individual without chondrosarcoma or relative to nomal tissue from the individual with chondrosarcoma. In some embodiments, the individual is diagnosed with chondrosarcoma if expression of one or more of the miRs listed above is any of about 10%, 20%, 30%, 40%, 50%, 60%, 70%, 80%, 90%, or 100% decreased in the biological sample from the individual relative to the expression level of the corresponding miR(s) from a sample derived from an individual without chondrosarcoma or relative to normal tissue from the individual with chondrosarcoma. In other embodiments, the individual is diagnosed with chondrosarcoma if expression of one or more of the miRs listed above is any of about 2, 3, 4, 5, 6, 7, 8, 9, or 10 fold less highly expressed in the biological sample from the individual relative to the expression level of the corresponding miR(s) from a sample derived from an individual without chondrosarcoma or relative to normal tissue from the individual with chondrosarcoma.

The assessment of miR expression is at the level of the transcribed RNA. Assessment of RNA expression levels of gene transcripts is routine and well known in the art. For example, one flexible and sensitive quantitative method for assessing RNA expression levels derived from a biological sample (such as a biopsy) is by quantitative RT-PCR (qRT-PCR) or by any other comparable quantitative PCR-based method. Additional methods for assessing RNA expression include, but are not limited to, Northern blotting, microarrays, in situ hybridization, serial analysis of gene expression (SAGE), dot blot, oligonucleotide arrays for chimeric RNA and antisense chimeric RNAs, amplification of the RNA by in vitro transcription mediated amplification (TMA), or ribonuclease protection assays.

In other embodiments, chondrosarcoma is diagnosed using additional methods. Imaging studies—including radiographs ("x-rays"), technesium bone scan, PET scan, computerized tomography (CT), and magnetic resonance imaging (MRI)—can also be used to make a presumptive diagnosis of chondrosarcoma. Further, a definitive diagnosis may also be made based on the identification of malignant cancer cells which produce cartilage in a biopsy specimen.

In yet other embodiments, the methods for diagnosing chondrosarcoma described above can further include treatment of the individual (using any of the methods for treating chondrosarcoma described above) if the diagnostic method indicates that the individual has chondrosarcoma III. Compositions of the Invention Also provided herein are compositions containing one or more inhibitors of a microRNA (miR) selected from the group consisting of miR-199a-3p, miR-26a, miR-762, miR-125a-5p, miR-let-7g, miR-16, miR-let-7f, miR-21, miR-let-7a, miR-638, miR-23a, miR-92a, miR-15b, miR-23b, miR-451, miR-483-5p, miR-15a, miR-27a, miR-26b, miR-let-7d, miR-27-b, miR-98, miR-145, miR-143, miR-1915, miR-149*, miR-7i, miR-7c, miR-7e, miR-936, miR-let-7b, miR-30c, miR-181d, miR-148a, miR-181c, miR-196a, miR-30a, miR-214, miR-187*, miR-663, miR-146a, miR-30d, miR-365, miR-424, miR-1231, miR-424*, miR-454, miR-455-5p, miR-337-3p, miR-181a, miR-381, and miR-30e in an amount effective to inhibit growth of human chondrosarcoma cell. Any inhibitor or combination of inhibitors of the miRs described above is suitable for use in the pharmaceutical compositions of the present invention, including those inhibitors disclosed herein. Furthermore, the miR inhibitors disclosed herein can be suitably formulated for delivery according to any of the delivery methods described herein.

Additionally, provided herein are compositions containing one or more nucleic acids encoding one or more microRNA (miR) selected from the group consisting of miR-320c, miR-320b, miR-320a, miR-127-3p, miR-1260, miR-140-3p, miR-22, miR-146b-5p, miR-107, miR-320d, miR-423-5p, miR-1974, miR-455-3p, miR-193b*, miR-103, miR-432, miR-151-3p, miR-31, miR-664*, miR-486-5p, miR-99a, miR-24, miR-191, miR-99b, miR-574-5p, miR-151-5p, miR-193a-5p, miR-1246, miR-877, miR-940, miR-1281, miR-494, miR-125-b-2*, miR-210, miR-1249, miR-874, miR-23a*, miR-30b*, miR-296-5p, miR-744, miR-197, miR-27b*, miR-34a, miR-34b, miR-34c, miR-126, miR-1280, and miR-324-3p; and a pharmaceutically acceptable carrier or diluent. Any nucleic acid or combination of nucleic acids encoding one or more of the miRs described above is suitable for use in the pharmaceutical compositions of the present invention, including those disclosed herein. Furthermore, nucleic acids encoding the miRs disclosed herein can be suitably formulated for delivery according to any of the delivery methods described herein.

A. Pharmaceutical Compositions

Any of the therapies for chondrosarcoma (such as nucleic-acid-based therapies, for example, use of antagomir miR-inhibitors) disclosed herein can be administered in the form of pharmaceutical compositions. These compounds can be administered by a variety of routes including intratumoral, oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. When employed as oral compositions, the oligonucleotides and another disclosed herein are protected from acid digestion in the stomach by a pharmaceutically acceptable protectant.

Specifically, this invention also includes pharmaceutical compositions which contain, as the active ingredient, one or more of the miR inhibitor, miR inhibitor expressing constructs, miR-encoding nucleic acid, or miR-expressing nucleic acid constructs disclosed herein associated with one or more pharmaceutically acceptable excipients or carriers. In making the compositions of this invention, the active ingredient (e.g., miR inhibitor or miR-expressing nucleic acid construct) is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 1%, 2%, 3%, 4%, 5%, 6%, 7%, 8%, 9%, or 10% by weight of the active compound, soft and hard gelatin capsules, suppositories, sterile injectable solutions, and sterile packaged powders.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The miR inhibitor or miR nucleic acid compositions can be formulated in a unit dosage form, each dosage containing from about 1 ng to about 100 mg or more, such as any of about 1 ng to about 25 ng, about 1 ng to about 50 ng, about 1 ng to about 100 ng, about 1 ng to about 500 ng, about 1 ng to about 1000 ng, about 1 ng to about 1500 ng, about 1 ng to about 5000 ng, about 1 ng to about 7500 ng, about 1 to about 1, about 100 ng to about 500 ng, about 500 ng to about 2000 ng, about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier. It will be understood, however, that the amount of the anti-cancer therapies actually administered will be determined by a physician, in the light of the relevant circumstances, including the condition to be treated, the chosen route of administration, the actual compound administered, the age, weight, and response of the individual patient, the severity of the patient's symptoms, and the like.

In general, dosage is from about 1 ng/kg to about 100 ng/kg of body weight (such as any of about 1 ng/kg, 2 ng/kg, 3 ng/kg, 4 ng/kg, 5 ng/kg, 6 ng/kg, 7 ng/kg, 8 ng/kg, 9v, 10 ng/kg, 11 ng/kg, 12 ng/kg, 13 ng/kg, 14 ng/kg, 15 ng/kg, 16 ng/kg, 17 ng/kg, 18 ng/kg, 19 ng/kg, 20 ng/kg, 21 ng/kg, 22 ng/kg, 23 ng/kg, 24 ng/kg, 25 ng/kg, 26 ng/kg, 27 ng/kg, 28 ng/kg, 29 ng/kg, 30 ng/kg, 31 ng/kg, 32 ng/kg, 33 ng/kg, 34 ng/kg, 35 ng/kg, 36 ng/kg, 37 ng/kg, 38 ng/kg, 39 ng/kg, 40 ng/kg, 41 ng/kg, 42 ng/kg, 43 ng/kg, 44 ng/kg, 45 ng/kg, 46 ng/kg, 47 ng/kg, 48 ng/kg, 49 ng/kg, 50 ng/kg, 51 ng/kg, 52 ng/kg, 53 ng/kg, 54 ng/kg, 55 ng/kg, 56 ng/kg, 57 ng/kg, 58 ng/kg, 59 ng/kg, 60 ng/kg, 61 ng/kg, 62 ng/kg, 63 ng/kg, 64 ng/kg, 65 ng/kg, 66 ng/kg, 67 ng/kg, 68 ng/kg, 69 ng/kg, 70 ng/kg, 71 ng/kg, 72 ng/kg, 72 ng/kg, 74 ng/kg, 75 ng/kg, 76 ng/kg, 77 ng/kg, 78 ng/kg, 79 ng/kg, 80 ng/kg, 81 ng/kg, 82 ng/kg, 83 ng/kg, 84 ng/kg, 85 ng/kg, 86 ng/kg, 87 ng/kg, 88 ng/kg, 89 ng/kg, 90 ng/kg, 91 ng/kg, 92 ng/kg, 93 ng/kg, 94 ng/kg, 95 ng/kg, 96 ng/kg, 97 ng/kg, 98 ng/kg, 99 ng/kg, or 100 ng/kg of body weight), from about 100 ng/kg to 500 ng/kg, from about 250 ng/kg to 750 ng/kg, from about 500 ng/kg to 1000 ng/kg, from about 750 ng/kg to 1250 ng/kg, from about 1000 ng/kg to 1500 ng/kg, from about 1250 ng/kg to 1750 ng/kg, from about 1500 ng/kg to 2000 ng/kg, from about 1750 ng/kg to 2250 ng/kg, from about 2000 ng/kg to 2500 ng/kg, from about 2250 ng/kg to 2750 ng/kg, from about 2500 ng/kg to 3000 ng/kg, from about 2750 ng/kg to 3250 ng/kg, from about 3000 ng/kg to 3500 ng/kg, from about 3250 ng/kg to 3750 ng/kg, from about 3500 ng/kg to 4000 ng/kg, from about 3750 ng/kg to 4250 ng/kg, from about 4000 ng/kg to 4500 ng/kg, from about 4250 ng/kg to 4750 ng/kg, from about 4500 ng/kg to 5000 ng/kg, from about 4750 ng/kg to 5250 ng/kg, from about 5000 ng/kg to 5500 ng/kg, from about 5250 ng/kg to 5750 ng/kg, from about 5500 ng/kg to 6000 ng/kg, from about 5750 ng/kg to 6250 ng/kg, from about 6000 ng/kg to 6500 ng/kg, from about 6250 ng/kg to 6750 ng/kg, from about 6500 ng/kg to from about 7000 ng/kg, from about 6750 ng/kg to 7250 ng/kg, from about 7000 ng/kg to 7500 ng/kg, from about 7250 ng/kg to 7750 ng/kg, from about 7500 ng/kg to 8000 ng/kg, from about 7750 ng/kg to 8250 ng/kg, from about 8000 ng/kg to 8500 ng/kg, from about 8250 ng/kg to 8750 ng/kg, from about 8500 ng/kg to 9000 ng/kg, from about 8750 ng/kg to 9250 ng/kg, from about 9000 ng/kg to 9500 ng/kg, from about 9250 ng/kg to 9750 ng/kg, from about 9500 ng/kg to 10 µg/kg, from about 0.01 µg to 100 g per kg of body weight, from 0.1 µg to 10 g per kg of body weight, from 1.0 µg to 1 g per kg of body weight, from 10.0 µg to 100 mg per kg of body weight, from 100 µg to 10 mg per kg of body weight, or from 1 mg to 5 mg per kg of body weight, and may be given once or more daily, weekly, monthly or yearly.

Pharmaceutical compositions which contain, as the active ingredient, one or more of the miR inhibitor, miR inhibitor expressing constructs, miR-encoding nucleic acid, or miR-expressing nucleic acid constructs disclosed herein are effective over a wide dosage range and are generally administered in a therapeutically effective amount. It will be understood, however, that the amount of the composition actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

Tablets or pills of the present invention can be coated or otherwise compounded to provide a dosage form affording the advantage of prolonged action and to protect the one or more of the miR inhibitor, miR inhibitor expressing constructs, miR-encoding nucleic acid, or miR-expressing nucleic acid constructs disclosed herein compounds from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the pharmaceutical compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles. Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described above. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner B. Oligonucleotide Modifications The naturally occurring internucleoside linkage of RNA and DNA is a 3' to 5 phosphodiester linkage. The oligonucleotides (for example, an antisense oligonucleotide or an siRNA oligonucleotide or an synthetic oligonucleotide used to compensate or restore expression of a naturally-occurring counterpart) used for treating chondrosarcoma according to any of the compositions or methods disclosed herein can have one or more modified, i.e. non-naturally occurring, internucleoside linkages. With respect to therapeutics, modified internucleoside linkages are often selected over oligonucleotides having naturally occurring internucleoside linkages because of desirable properties such as, for example, enhanced cellular uptake, enhanced affinity for target nucleic acids, and increased stability in the presence of nucleases.

Oligonucleotides (such as an antisense oligonucleotide an siRNA oligonucleotide) having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In one embodiment, oligonucleotides (such as antisense oligonucleotides) targeted to the miR molecules disclosed herein comprise one or more modified internucleoside linkages. In some embodiments, the modified internucleoside linkages are phosphorothioate linkages. In other embodiments, each internucleoside linkage of an oligonucleotide compound is a phosphorothioate internucleoside linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked. to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage. Specific though nonlimiting examples of oligonucleotides (such as antisense oligonucleotides or siRNA oligonucleotides) useful in the methods of the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In some embodiments, modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof) can also he employed. Various salts, mixed salts and free acid forms are also included. Oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other embodiments, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Representative United States patents that teach the preparation of the above phosphorus-containing and non-phosphorus-containing linkages include, but are not limited to, U.S. Pat. Nos. 5,541,306; 5,550,111; 5,563,253; 5,571,799; 5,587,361; 5,194,599; 5,565,555; 5,527,899; 5,721,218; 5,672,697 and 5,625,050, 5,596,086; 5,602,240; 5,610,289; 5,602,240; 5,608,046; 5,610,289; 5,618,704 5,623,070; 5,663,312; 5,633,360; 5,677,437; 5,792,608; 5,646,269 and 5,677,439, each of which is herein incorporated by reference.

Modified oligonucleotides (such as antisense oligonucleotides) used as anticancer therapies in conjunction with any of the methods or compositions disclosed herein may also contain one or more substituted sugar moieties. For example, the furanosyl sugar ring can be modified in a number of ways including substitution with a substituent group, bridging to form a bicyclic nucleic acid "BNA" and substitution of the 4'-O with a heteroatom such as S or N(R) as described in U.S. Pat. No. 7,399,845, hereby incorporated by reference herein in its entirety. Other examples of BNAs are described in published International Patent Application No. WO 2007/146511, hereby incorporated by reference herein in its entirety.

In other embodiments, the modified oligonucleotide comprises a bicyclic sugar moiety having a bridge group between the 2' and the 4'-carbon atoms. in certain such embodiments, the bridge group comprises from 1 to linked biradical groups. in certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)—, —C(R1)(R2)—, —C(R1)=C(R1)—, —C(R1)=N—, —Si(R1)(R$_2$)—, —S(=O)$_2$—, —S(O)—, —C(=O)— and 13 C(=S)—; where each R1 and R2 is, independently, H, hydroxyl, C1-C12 alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted. $C_5$-$C_{20}$ aryl, a heterocycle radical, a substituted hetero-cycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfonyl; and each substituent group is, independently, halogen, $C_1$-$C_{12}$ alkyl, substituted $C_1$-C alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ amino alkyl, $C_1$-$C_{12}$ aminoalkoxy, substituted $C_1$-$C_{12}$ aminoalkyl, substituted $C_1$-$C_{12}$ aminoalkoxy or a protecting group.

Oligonucleotides (such as antisense oligonucleotides) for use in any of the methods disclosed herein may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to oligonucleotide compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an oligonucleotide compound (such as an antisense oligonucleotide compound) for a target nucleic acid (such as a miR). Representative United States patents that teach the preparation of certain of the above noted modified nucleobases as well as other modified nucleobases include, but are not limited to, U.S. Pat. Nos. 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, each of which is herein incorporated by reference.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

EXAMPLES

Example 1

Identification of miRNAs Over and Underexpressed in Human Chondrosarcoma

As a first step in identifying miRNAs that are aberrantly expressed in human chondrosarcoma, miRNA array analysis was performed on two human chondrosarcomas (Grade II and III) with their normal articular cartilage used as a control.

Materials and Methods

RNA isolation and MicroRNA Microarray: Total RNA including miRNA was isolated from two human chondrosarcoma (Grades II and III), the same patients' normal articular cartilage, which were then pooled, primary chondrocytes, chondrocyte cell line CS-1, using a miRNeasy Mini Kit (Qiagen, Valencia, Calif., USA) following the manufacturer's instructions. The concentration and purity of total RNA were determined by a NanoDrop 2000C spectrophotometer (Thermo Fisher Scientific, Waltham, Mass., USA). Human microarray assay containing 894 human miRNA sequences was performed (LC Sciences, Houston, Tex., USA) using miRNA from the individual tumors and the pooled normal cartilage samples. The specific miRNA that were over- and underexpressed compared with the pooled normal articular cartilage (with p<0.01, Student's t-test) were identified for further analysis. Institutional review board approval was obtained for the study.

Results

Using the criteria of statistically significant differences in expression between tumor and normal cartilage in both tumors, the overexpressed and underexpressed miRs shown in Table 1 were identified.

TABLE 1

Over and underexpressed miRs identified in microarray experiments.
CS1 = chondrosarcoma human tumor 1; CL1 = cartilage control 1;
CS2 = human tumor 2; CL2 = cartilage control 2.

| miR | p-value CS1/CL1 | CS1 mean relative expression | CL1 mean relative expression | p-value CS2/CL2 | CS2 mean relative expression | CL2 mean relative expression |
| --- | --- | --- | --- | --- | --- | --- |
| hsa-miR-199a-3p | 1.34E−10 | 15,413 | 5,662 | 4.69E−06 | 18,800 | 5,662 |
| hsa-miR-26a | 3.29E−08 | 29,197 | 10,912 | 3.46E−02 | 95 | 6 |
| hsa-miR-762 | 1.17E−07 | 9,177 | 3,943 | 1.44E−07 | 9,568 | 3,943 |
| hsa-miR-125a-5p | 9.74E−07 | 5,933 | 3,735 | 6.84E−06 | 6,606 | 3,735 |
| hsa-let-7g | 1.20E−06 | 14,801 | 7,116 | 4.90E−07 | 13,929 | 7,116 |
| hsa-miR-16 | 1.43E−06 | 5,894 | 1,950 | 3.78E−07 | 6,968 | 1,950 |
| hsa-let-7f | 3.47E−06 | 39,289 | 20,457 | 2.99E−05 | 29,699 | 20,457 |
| hsa-miR-21 | 4.18E−06 | 14,652 | 232 | 4.45E−06 | 13,347 | 232 |
| hsa-let-7a | 4.77E−06 | 44,857 | 22,244 | 2.93E−05 | 35,011 | 22,244 |
| hsa-miR-638 | 8.95E−06 | 14,477 | 8,444 | 1.45E−05 | 14,065 | 8,444 |
| hsa-miR-23a | 8.97E−06 | 20,252 | 9,221 | 1.79E−05 | 17,645 | 9,221 |
| hsa-miR-92a | 9.63E−06 | 3,834 | 2,025 | 1.68E−04 | 2,843 | 2,025 |
| hsa-miR-15b | 1.10E−05 | 3,995 | 1,917 | 7.55E−04 | 2,658 | 1,917 |
| hsa-miR-23b | 2.69E−05 | 21,344 | 10,678 | 1.56E−05 | 18,412 | 10,678 |
| hsa-miR-451 | 3.48E−05 | 7,053 | 816 | 6.57E−06 | 4,866 | 816 |
| hsa-miR-483-5p | 4.58E−05 | 8,749 | 4,836 | 1.16E−06 | 15,561 | 4,836 |
| hsa-miR-15a | 6.75E−05 | 1,548 | 97 | 1.30E−05 | 1,175 | 97 |
| hsa-miR-27a | 9.29E−05 | 8,140 | 4,592 | 1.05E−05 | 7,069 | 4,592 |
| hsa-miR-26b | 9.30E−05 | 13,046 | 2,605 | 4.07E−05 | 21,074 | 2,605 |
| hsa-let-7d | 9.63E−05 | 37,833 | 21,780 | 5.70E−04 | 29,131 | 21,780 |
| hsa-miR-27b | 9.90E−05 | 9,054 | 6,307 | 5.79E−04 | 7,387 | 6,307 |
| hsa-miR-98 | 1.08E−04 | 16,759 | 10,737 | 8.14E−04 | 13,406 | 10,737 |
| hsa-miR-145 | 1.12E−04 | 2,555 | 154 | 5.01E−04 | 903 | 154 |
| hsa-miR-143 | 1.45E−04 | 1,203 | 63 | 2.99E−04 | 649 | 63 |
| hsa-miR-1915 | 1.79E−04 | 1,857 | 1,287 | 2.28E−06 | 3,557 | 1,287 |
| hsa-miR-149* | 2.02E−04 | 4,407 | 2,436 | 2.05E−06 | 6,594 | 2,436 |
| hsa-let-7i | 2.50E−04 | 14,711 | 10,284 | 7.88E−06 | 15,770 | 10,284 |
| hsa-let-7c | 2.53E−04 | 39,082 | 23,088 | 1.79E−03 | 31,121 | 23,088 |
| hsa-let-7e | 2.58E−04 | 29,233 | 16,914 | 7.47E−04 | 24,514 | 16,914 |
| hsa-let-7b | 3.21E−04 | 33,841 | 23,114 | 7.92E−03 | 27,705 | 23,114 |
| hsa-miR-30c | 6.85E−04 | 2,836 | 1,191 | 1.82E−03 | 1,875 | 1,191 |
| hsa-miR-181d | 7.96E−04 | 1,304 | 68 | 8.76E−03 | 203 | 68 |
| hsa-miR-148a | 9.69E−04 | 1,477 | 704 | 7.23E−05 | 4,071 | 704 |
| hsa-miR-181c | 1.00E−03 | 710 | 41 | 1.14E−03 | 291 | 41 |
| hsa-miR-196a | 1.11E−03 | 702 | 274 | 1.08E−04 | 928 | 274 |
| hsa-miR-30a | 1.67E−03 | 946 | 191 | 1.39E−03 | 1,025 | 191 |
| hsa-miR-214 | 2.59E−03 | 14,210 | 12,212 | 2.32E−03 | 14,481 | 12,212 |
| hsa-miR-187* | 3.60E−03 | 648 | 144 | 2.12E−03 | 612 | 144 |
| hsa-miR-663 | 4.00E−03 | 2,205 | 1,340 | 9.08E−04 | 2,252 | 1,340 |
| hsa-miR-146a | 4.19E−03 | 510 | 75 | 4.95E−03 | 463 | 75 |
| hsa-miR-30d | 5.42E−03 | 1,335 | 939 | 2.25E−03 | 1,448 | 939 |
| hsa-miR-365 | 5.56E−03 | 804 | 183 | 2.47E−03 | 844 | 183 |
| hsa-miR-424 | 6.27E−03 | 1,374 | 45 | 8.85E−03 | 875 | 45 |
| hsa-miR-1231 | 8.56E−03 | 492 | 246 | 3.17E−04 | 795 | 246 |
| hsa-miR-424* | 8.21E−04 | 110 | 23 | 2.87E−03 | 52 | 23 |
| hsa-miR-454 | 1.20E−03 | 215 | 24 | 4.29E−04 | 181 | 24 |
| hsa-miR-455-5p | 1.66E−03 | 181 | 95 | 3.60E−03 | 153 | 95 |
| hsa-miR-337-3p | 4.22E−03 | 57 | 12 | 8.16E−04 | 91 | 12 |
| hsa-miR-381 | 5.48E−03 | 26 | 10 | 2.53E−03 | 47 | 10 |
| hsa-miR-30e | 8.50E−03 | 311 | 43 | 8.91E−03 | 292 | 43 |
| hsa-miR-320c | 1.93E−09 | 3,908 | 22,585 | 7.03E−05 | 7,531 | 22,585 |
| hsa-miR-320b | 4.15E−09 | 3,597 | 22,088 | 7.61E−05 | 7,422 | 22,088 |
| hsa-miR-720 | 2.27E−08 | 1,193 | 29,654 | 1.32E−05 | 172 | 29,654 |
| hsa-miR-320a | 4.64E−08 | 4,104 | 23,550 | 3.16E−05 | 6,754 | 23,550 |
| hsa-miR-127-3p | 4.71E−08 | 177 | 1,445 | 3.47E−08 | 200 | 1,445 |

TABLE 1-continued

Over and underexpressed miRs identified in microarray experiments.
CS1 = chondrosarcoma human tumor 1; CL1 = cartilage control 1;
CS2 = human tumor 2; CL2 = cartilage control 2.

| miR | p-value CS1/CL1 | CS1 mean relative expression | CL1 mean relative expression | p-value CS2/CL2 | CS2 mean relative expression | CL2 mean relative expression |
|---|---|---|---|---|---|---|
| hsa-miR-1260 | 7.52E−08 | 12 | 6,444 | 1.03E−07 | 5 | 6,444 |
| hsa-miR-140-3p | 1.21E−07 | 8,171 | 19,485 | 3.59E−05 | 9,375 | 19,485 |
| hsa-miR-22 | 2.06E−07 | 655 | 2,138 | 5.72E−05 | 257 | 2,138 |
| hsa-miR-146b-5p | 2.69E−07 | 247 | 719 | 6.50E−05 | 317 | 719 |
| hsa-miR-107 | 8.81E−07 | 1,159 | 2,340 | 5.60E−07 | 871 | 2,340 |
| hsa-miR-320d | 1.73E−06 | 3,067 | 22,085 | 8.91E−03 | 292 | 43 |
| hsa-miR-1280 | 4.67E−06 | 915 | 24,004 | 3.75E−06 | 200 | 24,004 |
| hsa-miR-423-5p | 6.83E−06 | 2,133 | 6,213 | 1.57E−05 | 1,693 | 6,213 |
| hsa-miR-455-3p | 1.76E−05 | 2,877 | 11,567 | 7.27E−08 | 1,015 | 11,567 |
| hsa-miR-193b* | 2.02E−05 | 60 | 1,233 | 1.89E−05 | 131 | 1,233 |
| hsa-miR-103 | 2.04E−05 | 1,162 | 2,289 | 1.08E−04 | 882 | 2,289 |
| hsa-miR-432 | 2.23E−05 | 341 | 1,497 | 1.37E−05 | 234 | 1,497 |
| hsa-miR-151-3p | 2.54E−05 | 296 | 645 | 7.96E−05 | 296 | 645 |
| hsa-miR-31 | 2.66E−05 | 50 | 911 | 8.60E−06 | 15 | 911 |
| hsa-miR-664* | 4.61E−05 | 58 | 695 | 1.04E−04 | 41 | 695 |
| hsa-miR-1978 | 4.98E−05 | 632 | 2,360 | 1.42E−07 | 235 | 2,360 |
| hsa-miR-486-5p | 8.60E−05 | 379 | 662 | 3.29E−06 | 151 | 662 |
| hsa-miR-99a | 3.31E−04 | 3,683 | 6,554 | 5.85E−04 | 4,133 | 6,554 |
| hsa-miR-24 | 3.43E−04 | 5,623 | 7,317 | 2.31E−03 | 5,276 | 7,317 |
| hsa-miR-191 | 3.65E−04 | 2,992 | 4,694 | 3.05E−05 | 2,052 | 4,694 |
| hsa-miR-99b | 5.10E−04 | 672 | 1,888 | 8.62E−05 | 555 | 1,888 |
| hsa-miR-574-5p | 7.12E−04 | 1,897 | 5,214 | 9.83E−04 | 1,896 | 5,214 |
| hsa-miR-151-5p | 7.18E−04 | 2,207 | 2,684 | 4.94E−05 | 1,900 | 2,684 |
| hsa-miR-193a-5p | 7.91E−04 | 369 | 1,319 | 1.02E−04 | 303 | 1,319 |
| hsa-miR-1246 | 1.51E−03 | 19,632 | 21,591 | 8.58E−04 | 13,676 | 21,591 |
| hsa-miR-877 | 2.85E−03 | 87 | 364 | 3.88E−04 | 58 | 364 |
| hsa-miR-940 | 3.43E−03 | 475 | 1,254 | 2.91E−04 | 70 | 1,254 |
| hsa-miR-1281 | 3.61E−03 | 176 | 713 | 5.85E−05 | 50 | 713 |
| hsa-miR-494 | 3.85E−03 | 88 | 526 | 4.66E−03 | 98 | 526 |
| hsa-miR-125b-2* | 4.93E−06 | 32 | 169 | 1.42E−04 | 30 | 169 |
| hsa-miR-210 | 5.71E−06 | 70 | 468 | 2.04E−03 | 241 | 468 |
| hsa-miR-1249 | 6.02E−05 | 29 | 124 | 3.00E−03 | 14 | 124 |
| hsa-miR-874 | 1.24E−03 | 33 | 137 | 1.01E−03 | 39 | 137 |
| hsa-miR-23a* | 1.62E−03 | 28 | 166 | 1.79E−05 | 17,645 | 9,221 |
| hsa-miR-30b* | 2.26E−03 | 33 | 75 | 4.14E−03 | 40 | 75 |
| hsa-miR-296-5p | 3.35E−03 | 29 | 101 | 2.69E−04 | 18 | 101 |
| hsa-miR-744 | 4.34E−03 | 76 | 170 | 3.26E−04 | 53 | 170 |
| hsa-miR-197 | 7.61E−03 | 110 | 300 | 2.42E−03 | 63 | 300 |
| hsa-miR-27b* | 8.00E−03 | 56 | 172 | 7.66E−04 | 32 | 172 |
| hsa-miR-324-3p | 9.98E−03 | 33 | 115 | 1.62E−03 | 21 | 115 |

With respect to miR-1280, a qRT-PCR analysis confirms that expression of this miR is significantly decreased and/or absent in chondrosarcoma tissue (CS1, CS2) relative to its expression in normal cartilage (CL1, CL2; FIG. 1).

Example 2

Expression or Restoration of miR-126 Expression Inhibits Growth of Chondrosarcoma Cells This Example demonstrates that enhancing expression of miR-126 in chondrosarcoma cells is associated with decreased expression of the angiogenesis-promoting proteins vascular endothelial growth factor (VEGF), placental growth factor (PGF), and thrombospondin-1 (TSP-1), decreased cellular proliferation, and decreased Met protein expression.

Materials and Methods

Cell lines: Human primary chondrocytes and chondrosarcoma cell lines were cultured as previously described (Kulshreshtha et al., Cell Cycle. 2007; 6:1426-1431). CS-1 (a gift from Dr. Francis Hornicek, Harvard Medical School, Boston, Mass.) was cultured in Gibco RPMI 1640 Medium (Life Technologies, Grand Island, N.Y.), with 10% FBS in a humidified incubator (NuAire Inc, Plymouth, Minn.) under 5% CO2 and either normoxia (ambient oxygen) or hypoxia (2% O2)(11). CS-1 was derived from human grade III chondrosarcoma and metastasizes in a xenograft mouse model(Susa M, Morii T, Yabe H, Horiuchi K, Toyama Y, Weissbach L, et al. Alendronate inhibits growth of high-grade chondrosarcoma cells. *Anticancer Res.* 2009 June; 29(6):1879-88.). All cells were cultured in a humidified incubator (NuAire Inc, Plymouth, Minn., USA) under 5% CO2 and either normoxia or hypoxia (2% O2) (Lin et al., *J Orthop Res.* 2004; 22:1175-1181).

Transfection with microRNA, anti-microRNA: Transient miR knockdown or overexpression was achieved with syn-hsa-miR-181a, 34a, 126 or others miScript miRNA mimic, control miR, anti-hsa-miR-181a, 34a, 126 or others miScript miRNA inhibitor, and miScript inhibitor negative control (Applied Biosystems). Transfections were performed with GenMute transfection reagent (SignaGen Laboratories, Gaithersburg, Md.). pmiRZIP lentivector expressing anti-miR-181a or control sequence (SBI, Mountain View, Calif.) was used for permanent miR-181a knockdown experiments. Transduction-ready FIV-based pseudoviral particles were generated using pPACK-H1 Lentivector Packaging System together with 293TN cell line (SBI), at a titer of $1.06 \times 10^9$ IFU/ml. Control was Lenti-scramble Hairpin control pseudoviral particles at a titer of $1 \times 10^9$ IFU/ml. Cells were cultured in 12-well plates at a density of $1 \times 10^5$/well for 1 day, infected by pseudoviral particles (using a multiplicity of infection of 100 viruses per cell) and cultured for 72 hrs, then selected for puromycin (5 µg/ml) resistance for stable cell lines. Stably transduced cells were used for vitro and in vivo experiments.

Angiogenesis antibody array: Human Angiogenesis Array Kit is a membrane-based sandwich immunoassay. Samples are mixed with a cocktail of biotinylated detection antibodies and then incubated with the array membrane which is spotted in duplicate with capture antibodies to specific target proteins. Captured proteins are visualized using chemiluminescent detection reagents. The signal produced is proportional to the amount of bound analyte. It is sensitive and economical tool to simultaneously detect the relative levels of 55 angiogenesis-related proteins in a single sample.

ELISA: Conditioned medium was obtained 72 hours after transfection. Soluble VEGF-165 and MMP1 were detected using VEGF and MMP1 Immunoassay kits (R&D Systems, Minneapolis, Minn.) according to manufacturer's instructions. VEGF-165 and MMP1 levels were measured two times for each condition and with normalization to the number of cells at the end of the culture period. Each experiment was repeated three times. Twenty mg of xenograft tumor tissue in RIPA buffer containing proteinase inhibitors (Roche) was homogenized on ice using TissueRuptor (Qiagen). Tissue lysates were centrifuge at 14000 rpm for 30 min, supernatant saved at −80° C. for later use. VEGF-165 levels in xenograft tumor lysates were normalized to total protein.

qRT-PCR: miR expression evaluated with qRT-PCR using Hs_miR-181a primer 5'-AACAUUCAACGCUGU-CG-GUGAGU-3' (SEQ ID NO:198) and 1280: 5'UCC-CACCGCUGCCACCC-3' (SEQ ID NO:199) (Qiagen). The comparative threshold cycle (Ct) method, i.e., $2-\Delta\Delta Ct$ method is used to calculate fold amplification. For quantification of mRNA, total RNA was isolated from chondrocytes, CS-1 cells, and xenograft mouse tumors using the RNAqueous® Kit (Ambion, Austin, Tex., USA). SYBR real-time PCR was carried out using two-step real-time qRT-PCR (Qiagen) with normalization to 18S rRNA (18S). The comparative threshold cycle (Ct) method, i.e., the $2-\Delta\Delta Ct$ method, was used for the calculation of fold amplification. Each experiment was evaluated with three PCR reactions and each experiment was repeated three times, the sample size necessary to maintain power at 0.80 to detect a 50% decrease with an alpha of 0.025 (one-tailed t-test).

Western blot: Cell or tumor lysates containing forty µg of protein were separated via SDS-PAGE (Bio-Rad, Hercules, Calif.) and probed with antibodies for VEGF (VEGFA), MMP-1, SSX, and actin (Santa Cruz Biotechnology, Santa Cruz, Calif.). The fluorescent signals were detected using a fluorescently-labeled secondary goat anti-rabbit antibody (Alexa Fluor 680) (Molecular Probes, Eugene, Oreg.) and analyzed on Licor Odyssey Scanner (LI-COR Biosciences, Lincoln, Nebr.). Western Blot analyses were performed as previously described with specific antibodies (IMGNEX, San Diego, Calif.) and actin antibody (Santa Cruz Biotechnology, Santa Cruz, Calif.). Protein concentrations were determined using the Quick Start Bradford protein assay (Bio-Rad).

Cell proliferation assay: CyQUANT® Cell Proliferation Assay Kit according to manufacturer's protocol Results VEGF is a signal protein produced by cells that stimulates vasculogenesis and angiogenesis. When VEGF is overexpressed, it can contribute to disease. Solid cancers cannot grow beyond a limited size without an adequate blood supply; cancers that can express VEGF are able to grow and metastasize. Overexpression of VEGF can also cause vascular disease in the retina of the eye and other parts of the body.

Figure 2:
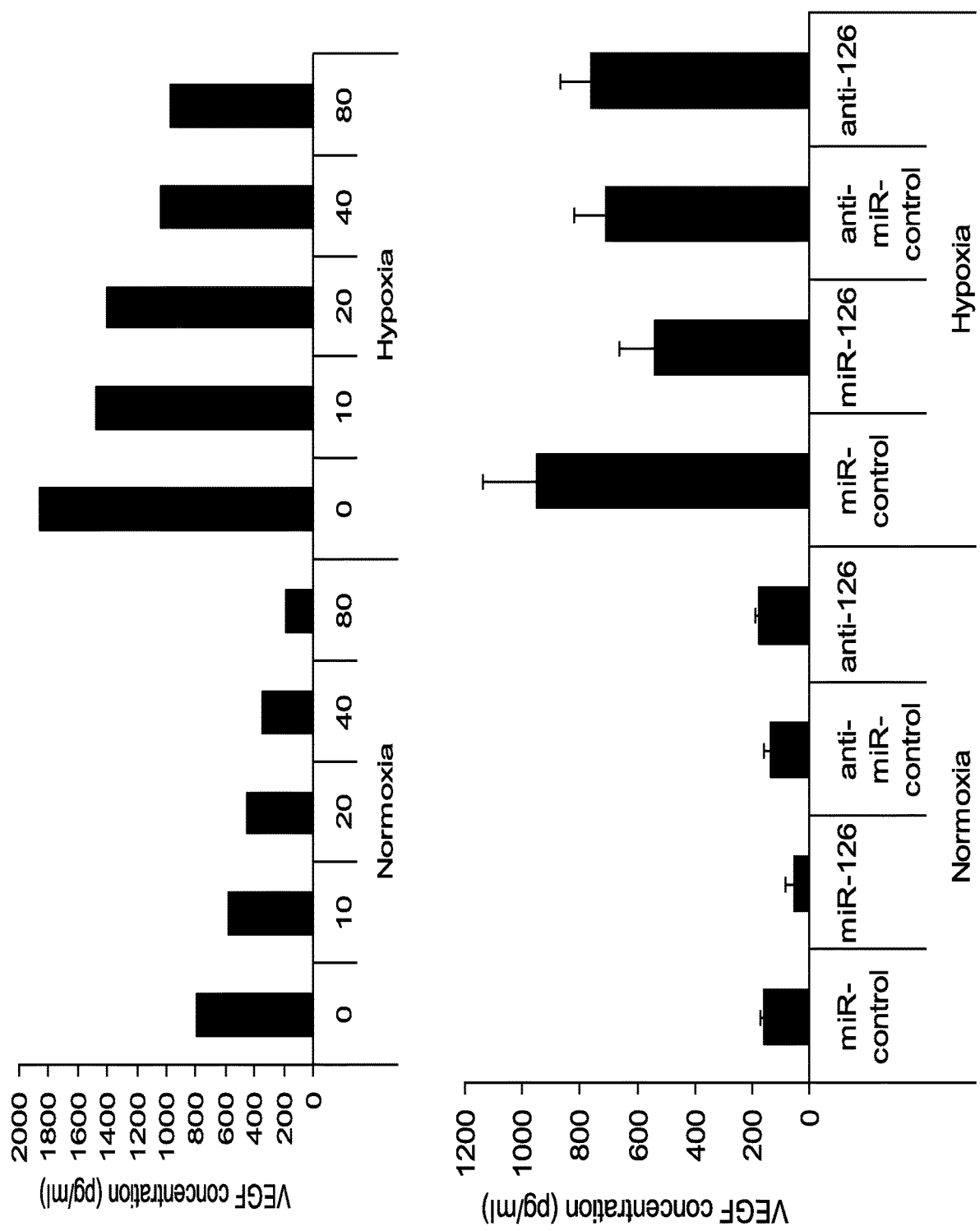
FIG. 2 depicts graphs showing the results of an ELISA measuring VEGF expression in chondrosarcoma cells. miR-126 was administered under both normoxic and hypoxic conditions in concentrations from 10-80 nM (top). VEGF concentration was also assessed following administration of miR-126 or anti-miR-126 under both normoxic and hypoxic conditions (bottom). Upper panel concentrations in nM. Lower panel 20 nM for miR-126 and 80 nM for anti-miR-126. Hypoxia is 2% oxygen concentration.

As shown in FIG. 2 (top), miR-126 inhibited VEGF expression in a dose-dependent manner (10-80 nM of miR-126) in chondrosarcoma cells under both normoxia and hypoxia as measured by ELISA. FIG. 2 (bottom) also shows that transient transfection of chondrosarcoma cells with miR-126 resulted in reduced VEGF expression under both normoxic and hypoxic conditions. However, this effect was obviated when cells were administered an anti-miR-126 antagomir.

Figure 3:
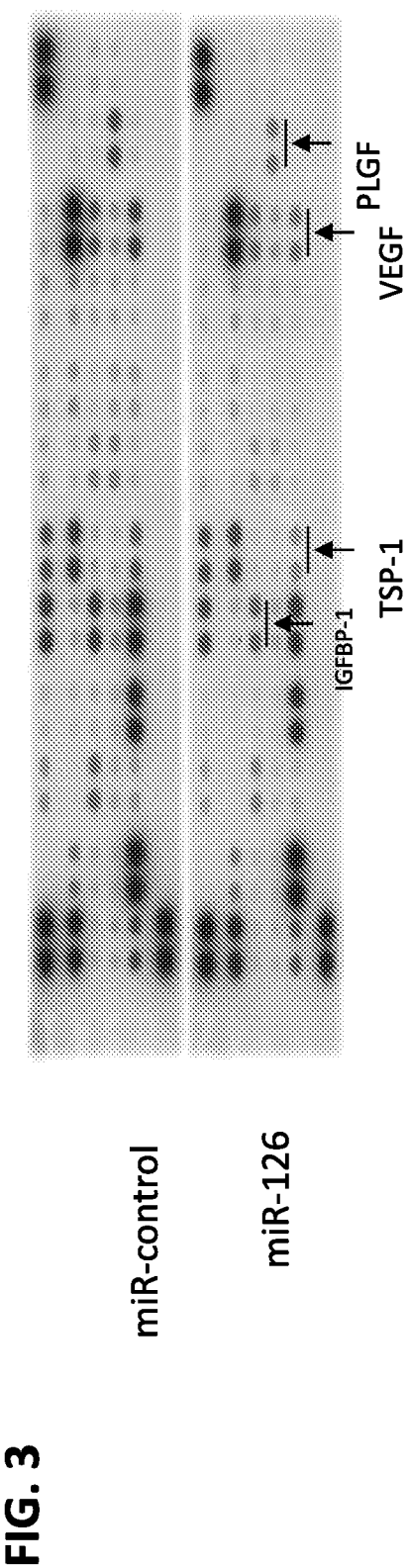
FIG. 3 depicts the results of an angiogenesis antibody array analysis in chondrosarcoma cells following treatment with a miR control (top) and miR-126 (bottom).

Similarly, as shown in FIG. 3, an angiogenesis antibody array showed miR-126 reduces the expression of not only VEGF, but also placental growth factor (PLGF) and thrombospondin-1 (TSP-1). PLGF is a member of the VEGF sub-family and is considered to be a key molecule in angiogenesis and vasculogenesis, in particular during embryogenesis and neovascularization (Moons et al., *Circulation*, 2005, 111(21):2828-2836). TSP-1 is an adhesive glycoprotein that mediates cell-to-cell and cell-to-matrix interactions. Various domains of and receptors for TSP1 have been shown to have pro-adhesive and chemotactic activities for cancer cells, suggesting that this molecule may have a direct effect on cancer cell biology (Taraboletti et al., *J. Cell Biol.*, 1987, 105(5):2409-15).

Figure 4:
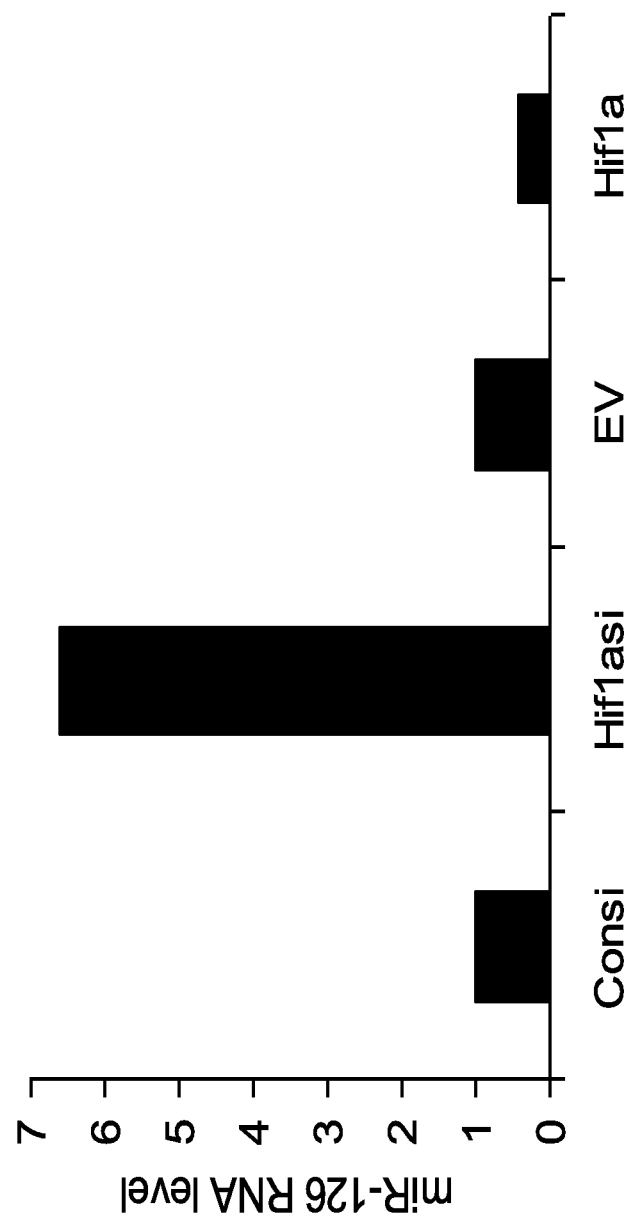
FIG. 4 depicts a graph showing miR-126 RNA expression as measured by qRT-PCR following overexpression of hif1a (Hif1a) in chondrosarcoma cells or treatment with an antisense inhibitor of hif1a expression (Hif1asi). EV is empty vector control.

Based on the observation that VEGF expression goes up under hypoxic conditions (FIG. 2), expression of miR-126 was examined in response to expression of hypoxia-inducible factor 1-alpha (hif11a). Hif11a is a subunit of a heterodimeric transcription factor hypoxia-inducible factor 1 (HIF-1) and is considered as the "master" transcriptional regulator of cellular and developmental response to hypoxia (Wang et al., *PNAS*, 1995, 92(12):5510-5514). As shown in FIG. 4, hif1a regulated miR-126 expression as measured by qRT-PCR. Specifically, reduction of hif1a expression by a specific hif1a siRNA (20 nM) increased miR-126 expression while overexpression of hif1a by transfection with an hif1a-expressing construct decreased miR-126 expression in under normoxic conditions. These results show that tumor hypoxia effects are partially mediated by expression of microRNA 126

Figure 5:
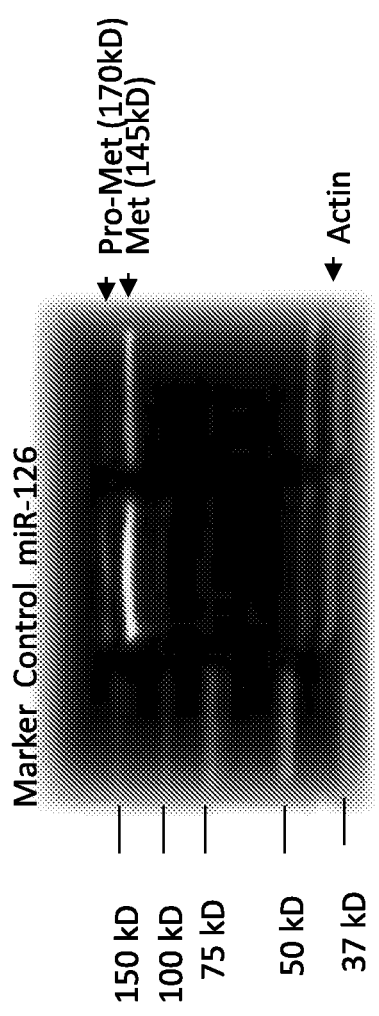
FIG. 5 depicts a western blot showing Met protein level under control miRNA conditions and after overexpression of miR-126 in chondrosarcoma cells. Expression of actin protein is used as a loading control.

In addition, by restoring expression of miR-126, expression of Met protein decreased in chondrosarcoma cells compared to cells treated with an miRNA control, as shown in FIG. 5. Met has been shown to play important roles in the development of cancer through activation of key oncogenic pathways (e.g., RAS, PI3K, STAT3, beta-catenin); induction of angiogenesis; and cellular dissociation due to metalloprotease production, which often leads to metastasis.

Figure 6:
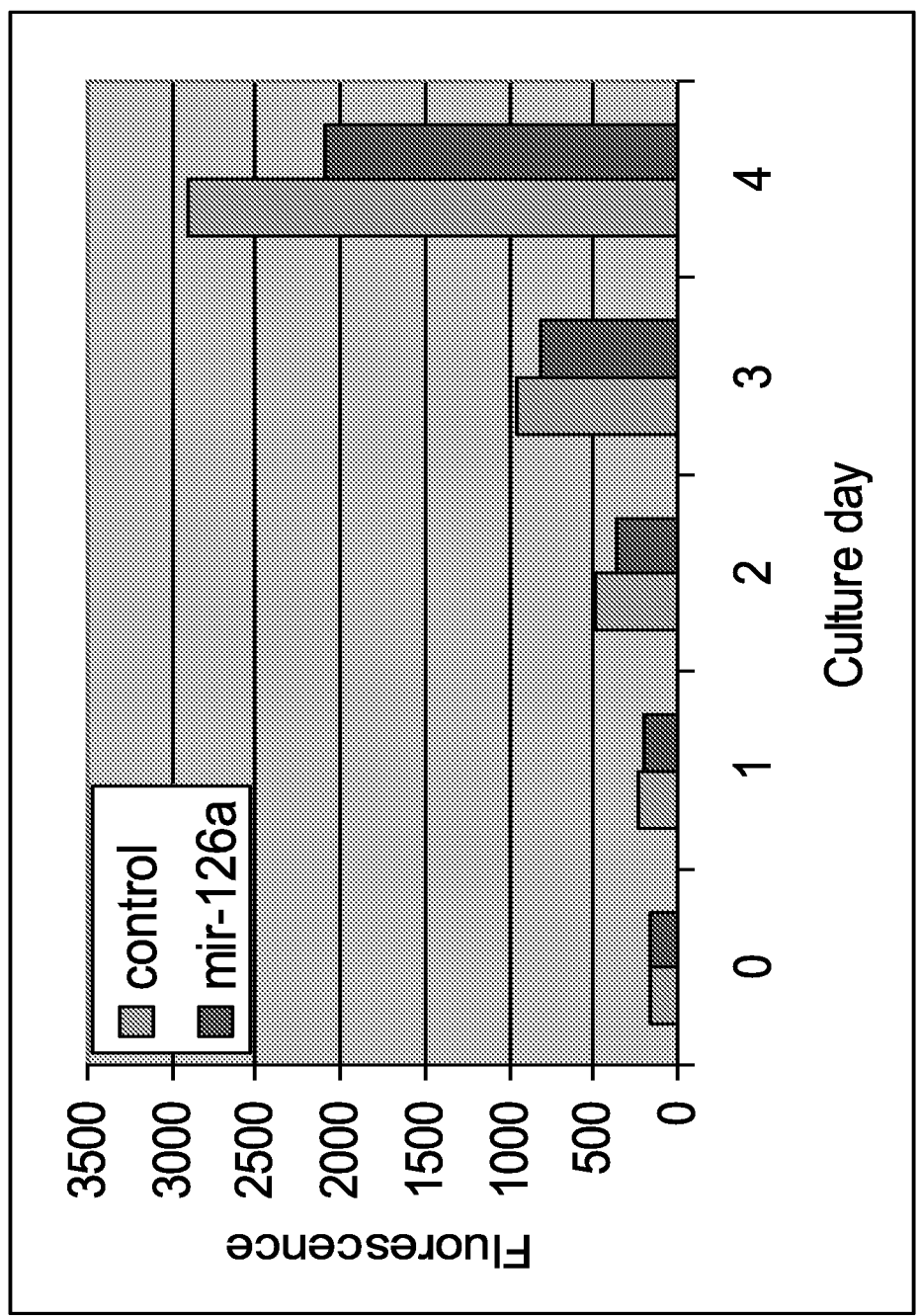
FIG. 6 depicts a graph showing proliferation of chondrosarcoma cells treated with both a control miR and miR-126a over time as measured by fluorescence.

Finally, chondrosarcoma cells transfected with 20 nM miR-126 grew more slowly over time compared to cells treated with a control miR as measured by as measured by CyQUANT® Cell Proliferation Assay Kit (FIG. 6).

In summary, expression of miR-126 in chondrosarcoma cells is associated with downregulation of multiple pro-angiogenic and metastasis-promoting factors, including VEGF, PLGF, TSP-1, and Met. Moreover, hif1a appears to negatively regulate the expression of miR-126 under hypoxic conditions. Following transfection with miR-126, chondrosarcoma cells were observed to grow more slowly over time as compared to control-treated cells.

Example 3

Figure 7B:
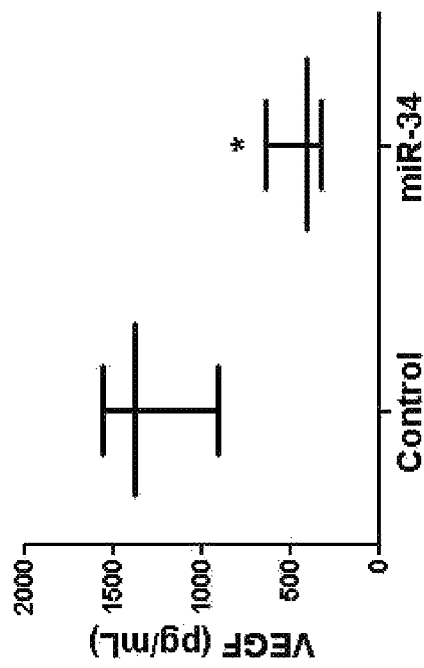
FIG. 7B depicts a graph showing VEGF protein expression in chondrosarcoma cells transfected with miR-34a relative to transfection with control miR in chondrosarcoma cells (* p<0.02, n=3).
Figure 7A:
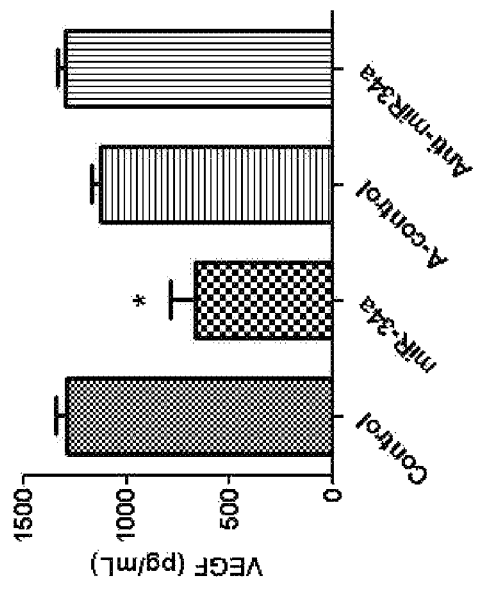
FIG. 7A depicts a graph showing VEGF protein expression in chondrosarcoma cells transfected with control miR, miR-34a, an antisense control oligonucleotide, or an anti-sense-miR34a oligonucleotide as measured by ELISA.
Figure 7C:
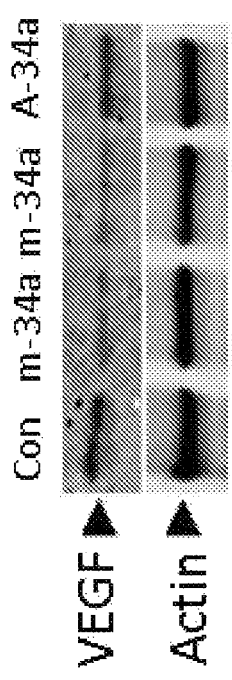
FIG. 7C depicts a western blot showing VEGF protein expression in chondrosarcoma cells transfected with miR-34a compared to control cells and cells transfected with an anti-miR-34a construct. m-34a is miR-34a mimic, the same sequence as miR-34a. A-34a is the antagomir, (antisense sequence).
Figure 8:
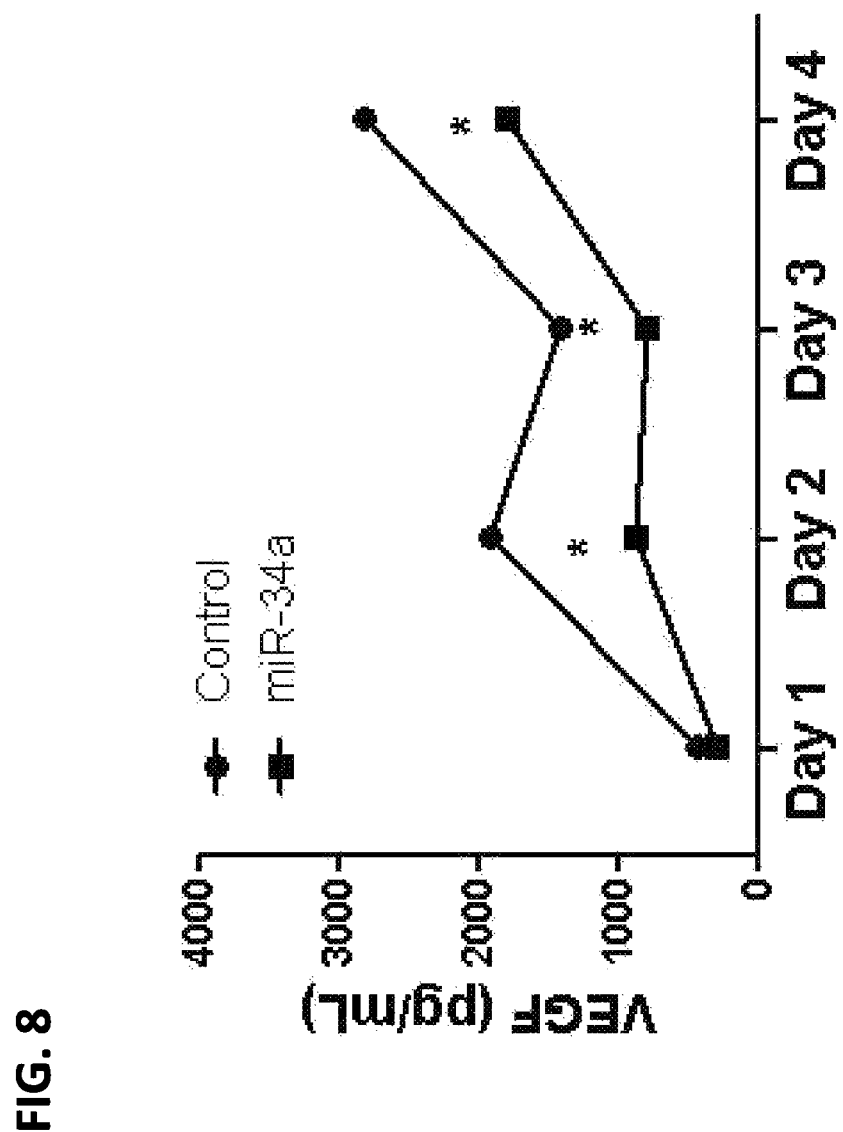
FIG. 8 depicts a graph showing expression of VEGF protein secreted from chondrosarcoma cells transfected with control miR and miR-34a over time as measured by ELISA (* p<0.001).
Figure 9:
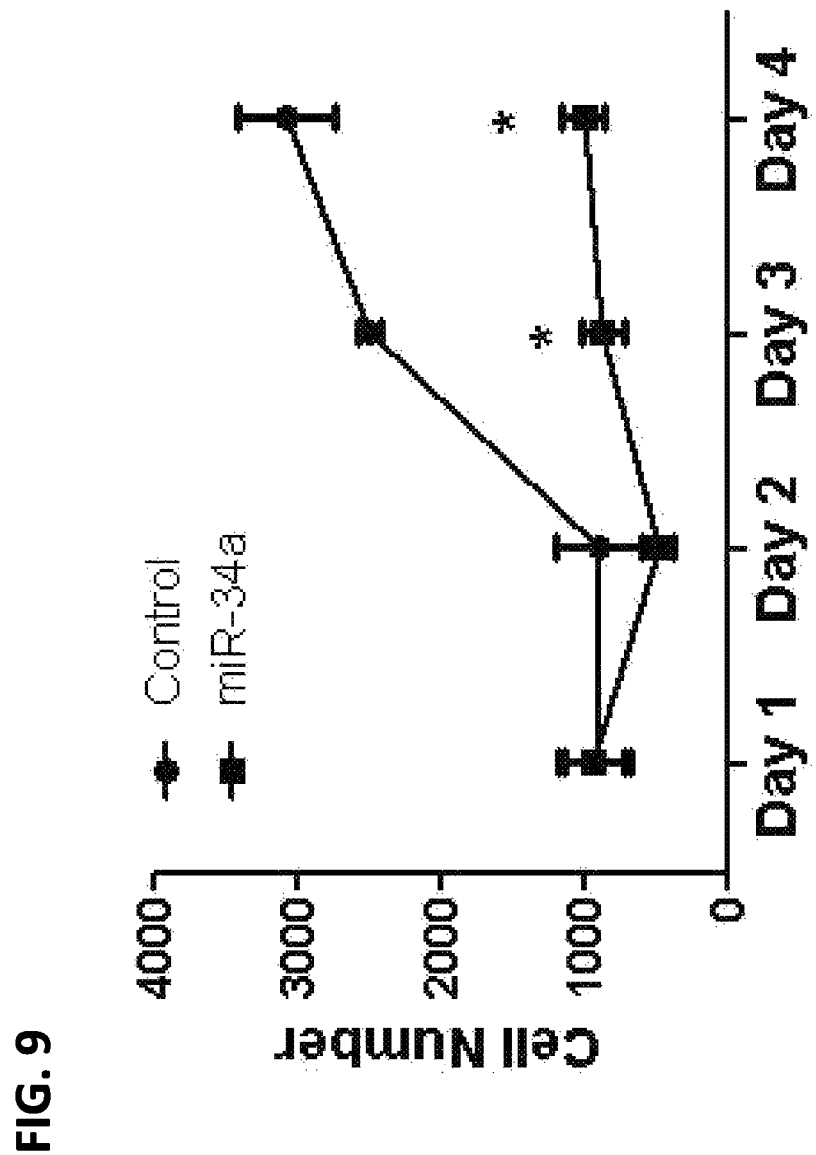
FIG. 9 depicts a graph showing chondrosarcoma cell proliferation over time in cells transfected with miR-34a compared to cells transfected with control miR (*p<0.001).

Expression or Restoration of miR-34a Expression Inhibits Expression of VEGF and Growth of Chondrosarcoma Cells This Example shows that increased or restored miR-34a expression in chondrosarcoma cells results in decreased VEGF and SSX-1 expression as well as decreased cellular proliferation.
Materials and Methods
ELISA, western blot, qRT-PCR, and cell proliferation assays were performed as described above.
Results
Transfection of chondrosarcoma cells with miR-34 (20 nM) significantly decreased expression of VEGF protein compared to control cells (cells treated with control miR or control anti-miR sequences) or cells treated with an anti-miR-34a construct (FIG. 7A-7C). Transfection with miR-34a was also associated with decreased VEGF expression over time as measured by ELISA, as shown in FIG. 8. Additionally, as shown in FIG. 9, chondrosarcoma cells transfected with miR-34a exhibited significantly decreased growth rates over time compared to control cells.

Figure 10A:
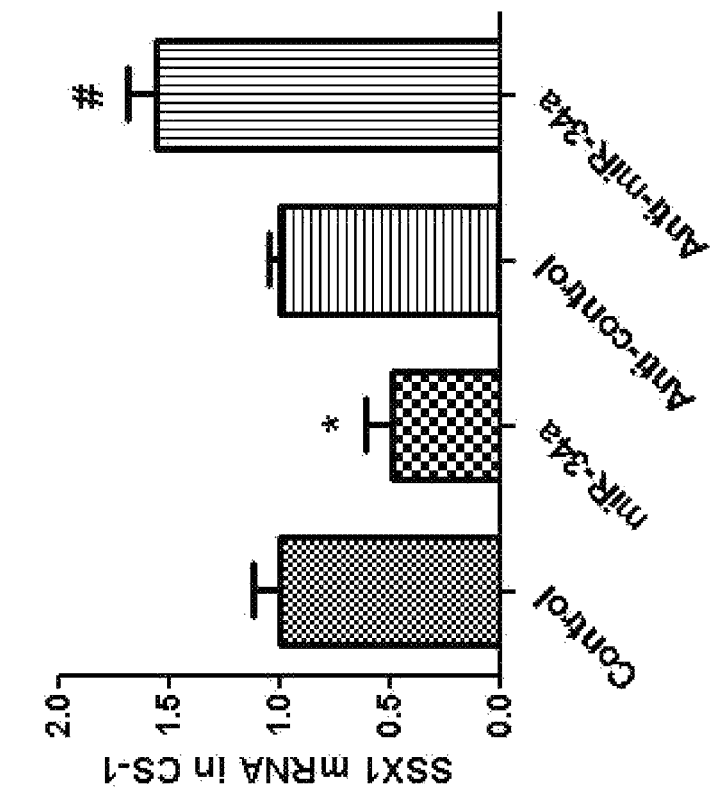
FIG. 10A depicts a graph showing expression of SSX1 mRNA in chondrosarcoma cells transfected with control miR, miR-34a, anti-miR control sequence, and cells transfected with an antisense-miR-34a oligonucleotide as measured by qRT-PCR.
Figure 10B:
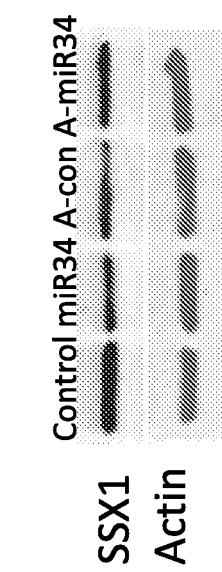
FIG. 10B depicts a western blot showing SSX1 protein expression in chondrosarcoma cells after the same transfections in FIG. 10A.
Figure 11A:
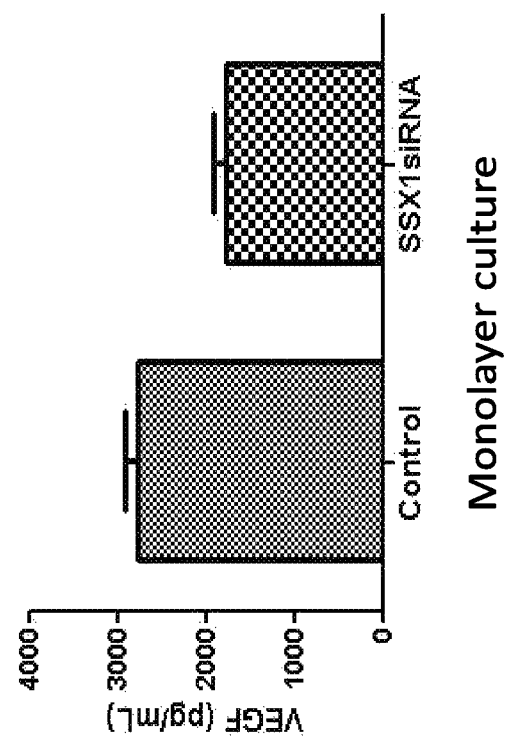
FIG. 11A depicts a graph showing expression of VEGF mRNA in chondrosarcoma cells transfected with an SSX1 siRNA compared to control siRNA and cells transfected with an SSX4 siRNA as measured by qRT-PCR.
Figure 11B:
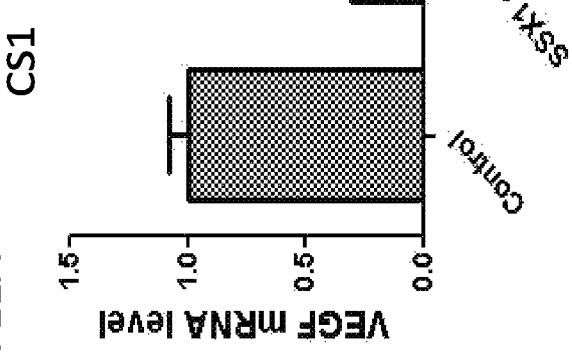
FIG. 11B is a graph showing expression of VEGF protein in a monolayer culture of chondrosarcoma cells transfected with an SSX1 siRNA compared to control siRNA as measured by ELISA.
Figure 11C:
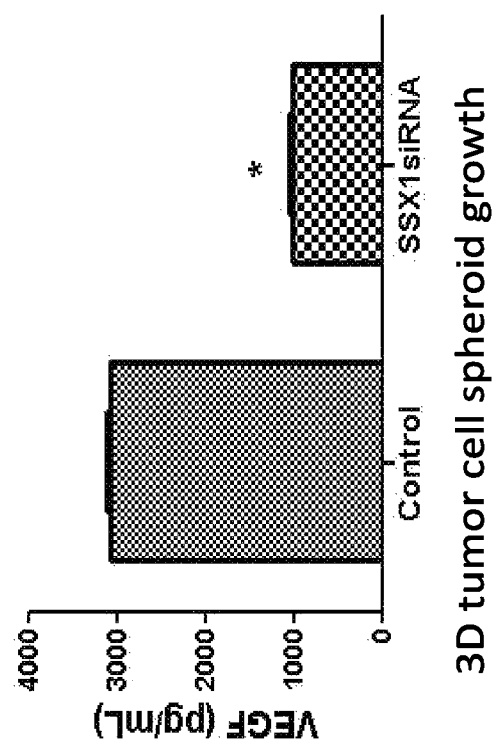
FIG. 11C depicts a graph showing expression of VEGF protein in a 3D tumor cell spheroid growth culture of chondrosarcoma cells transfected with an SSX1 siRNA compared to control siRNA as measured by ELISA.

Synovial sarcoma X-1 (SSX1) is a tumor antigen involved in the t(X;18) translocation characteristically found in all synovial sarcomas. This translocation results in the fusion of the synovial sarcoma translocation gene on chromosome 18 to one of the SSX genes on chromosome X. The encoded hybrid proteins are thought to be responsible for transforming activity (Sun et al., *Oncogene*, 25(7):1042-52). As shown in FIG. 10A, transfection of chondrosarcoma cells with miR-34a (20 nM) resulted in decreased SSX1 mRNA expression as measured by qRT-PCR compared to control cells or cells treated with an anti-miR-34a oligonucleotide construct. Similar results were observed with respect to SSX1 protein expression following transfection of chondrosarcoma cells with miR-34a (FIG. 10B). However, an siRNA directed against SSX4 did not result in decreased VEGF mRNA expression (FIG. 10A). Further, as shown in FIG. 11A-C, transfection with an SSX1 siRNA (20 nM) resulted in decreased VEGF mRNA and protein expression in chondrosarcoma cells both in monolayer and a 3D tumor cell spheroid growth culture conditions (Matrigel suspension).

Figure 12:
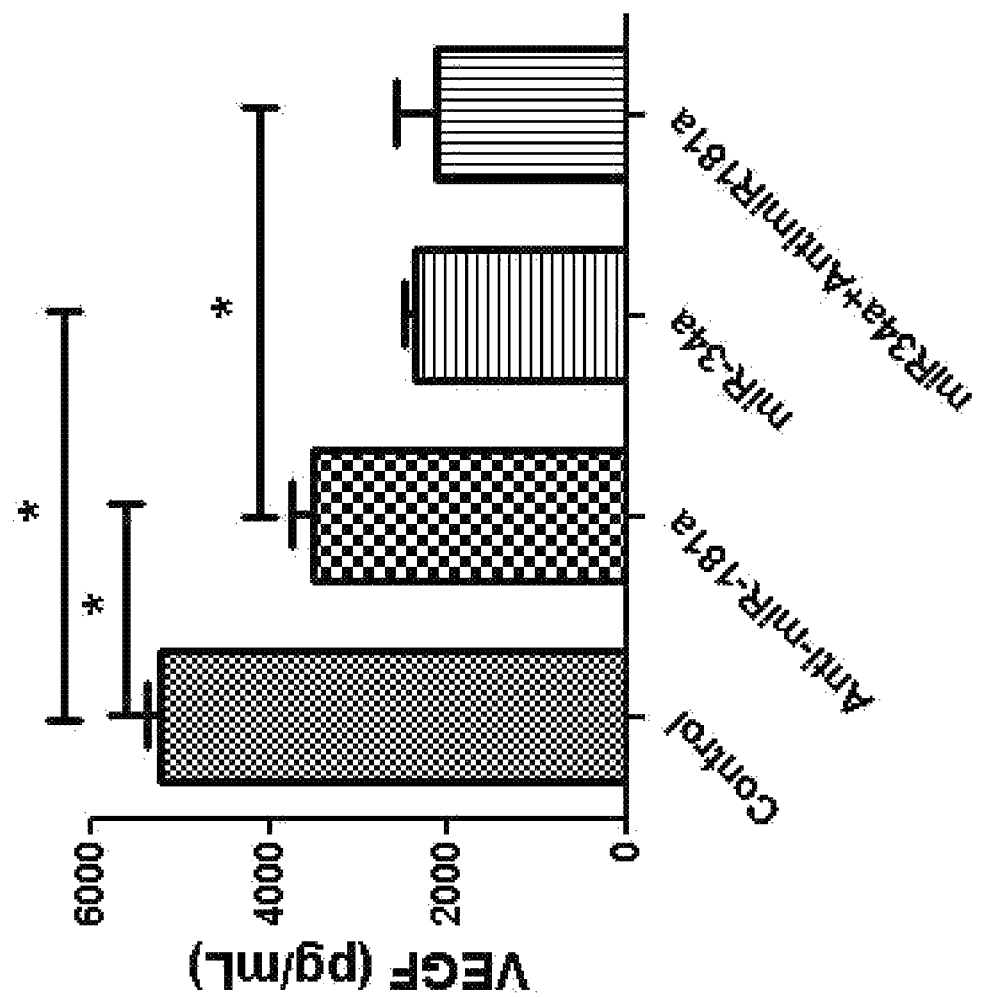
FIG. 12 depicts a graph showing VEGF expression in chondrosarcoma cells transfected with and-miR-181a oligonucleotides, transfected with miR-34a, or combination treatment with an anti-miR-181a and with miR-34a compared to control cells as measured by ELISA.

As shown in FIG. 12, co-administration of miR-34a with an anti-miR181a oligonucleotide (20 nM) construct resulted in decreased VEGF protein expression in chondrosarcoma cells.

In summary, this example shows that expression of miR-34a results in decreased expression of VEGF and SSX1 as well as significantly decreased proliferation in chondrosarcoma cells. As shown in FIG. 10-11, miR-34a may exert some of its effects on VEGF expression by decreasing the expression of SSX1.

Example 4

Nanopiece Delivery of a miR-181a Inhibitor to Chondrosarcoma Cells

This example shows that nanopieces can be used to enhance transfection of chondrosarcoma cells with nucleotide sequences (oligos and molecular beacons) both in vitro and in vivo.

Materials and Methods
Preparation of nanopieces (NP) for IV injection into nude mice: the antagomir amount needed is calculated as below: each IV injection for one mouse is 6 µL (50 µM). siRNA and JAK (AAT or RNT) were thawed at room temperature. ["JAK": Janus base with Amine or lysine (K), and "AAT": fused Amino Adenine with Thymine]. The following were mixed in an Eppendorf tube: siRNA: 6 µL, water: 60 µL, AAT/RNT: 90 µL. The tube was sonicated in Qsonica Sonicator for 2.5 minutes. The Eppendorf tubes were then centrifuged to spin down aqueous droplets in the tube. Next, 3.9 µL sterile PEG (polyetelyne glycol) 400 and 2.16 µL sterile 45% glucose were added into the Eppendorf tube containing assembled NP (total volume is 162 µL). The NP was stored on ice before animal injection. Exemplary NPs useful in the therapeutic methods described herein include those with a length of 1 nm to 200 nm, e.g. a length of about 100 nm, and a width or diameter of 1 nm to 60 nm, e.g., 20 nm. For example, the length is in the range of 50-150 nm and the width/diameter is in the range of 20-40 nm. Typically, the nanopieces are characterized by a length of about 100 nm and width/diameter of about 20 nm.

Cell line and xenograft tumor model: CS-1 cells (100 µl of 1×10$^6$ cells) were mixed with 300 µL Matrigel™ (BD Biosciences, San Jose, Calif.) and injected subcutaneously in the back of nude mice (nu/nu 6-8 week old female, Charles River Laboratory, Wilmington, Mass.).

FMT assays: in vivo bioimaging with fluorescence-based tomography (FMT, PerkinElmer, Waltham, Mass.) was performed at three weeks after injection of tumor cells. Twenty-four hours before imaging, mice were injected via tail vein with 2 nmol MMPSense 680 and Angiosense 750 (PerkinElmer, Waltham, Mass.). Mice were anesthetized with ketamine (ip) during FMT imaging. FMT is acquired with a continuous wave-type scanner capable of acquiring transillumination, reflectance and absorption data at 680 nm excitation and 700 nm emission or 750 nm excitation and 780 nm emission (PerkinElmer). AngioSense and MMPSense content in xenograft tumors was determined by region of interest analysis. Fluorochrome concentration in the target was calculated from reconstructed images and expressed as femtomoles of fluorochrome per defined target volume (the primary tumor).

Figure 13A:
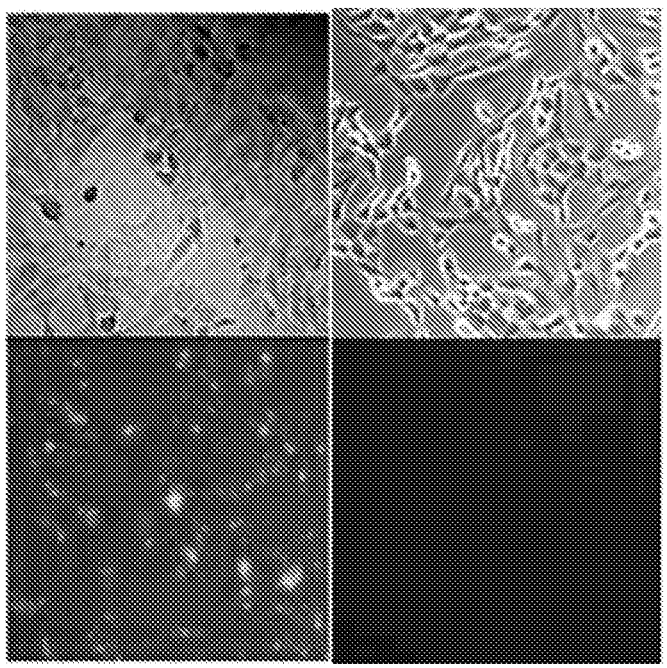
FIG. 13A depicts fluorescent (left) and bright field (right) micrographs showing transfection of chondrosarcoma cells with a fluorescently labeled anti-miR-control carried by nanopieces (top, left), and anti-miR-control alone (bottom, left) indicating cells are transfected when nanopieces are used for delivery.
Figure 13B:
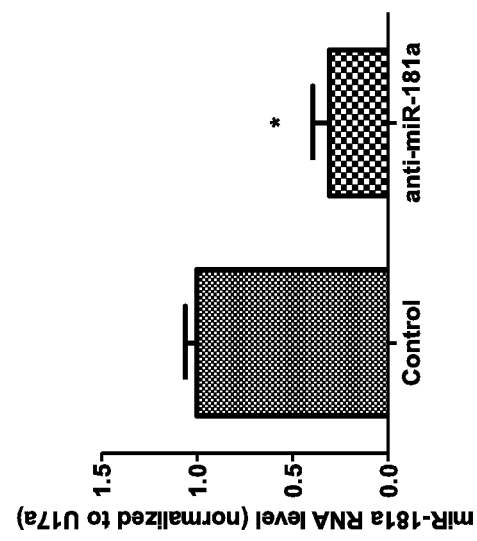
FIG. 13B depicts a graph showing miR-181a RNA levels as measured by qRT-PCR in control miR/nanopiece versus anti-miR-181a/nanopiece-treated chondrosarcoma cells.

Results
Oligonucleotide sequences cannot gain entry into a cell unless the cell membrane is permeabilized as is done in cell culture experiments with lipophilic agents, or by utilizing a vector, such as a virus, or utilizing nanopieces. Chondrosarcoma cells treated with fluorescent labeled control oligonucleotide for 24 hours followed by washing do not fluoresce, indicating lack of entry to the cell (FIG. 13A (bottom)). In contrast, if the oligos are delivered with nanopieces for 24 hours and then washed, the cells do fluoresce, indicating that the nanopieces have transfected the cells with the oligonucleotides (FIG. 13A (top)). Bright field views (FIG. 13A) demonstrate the presence of cells in both conditions. When the experiment is repeated with control antagomiR and one directed against miR-181a, expression of miR-181a is decreased when measured by qPCR (FIG. 13B).

Figure 14B:
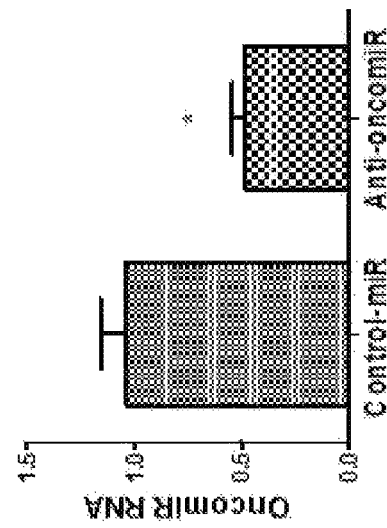
FIGS. 14A-C depict intracellular nanopiece delivery of nucleotide sequences.
Figure 14A:
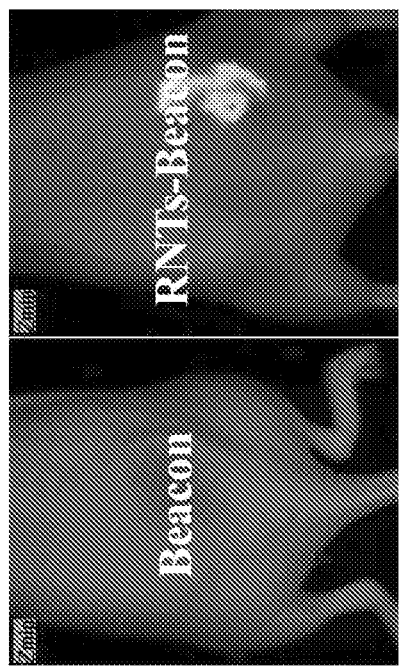
Figure 14C:
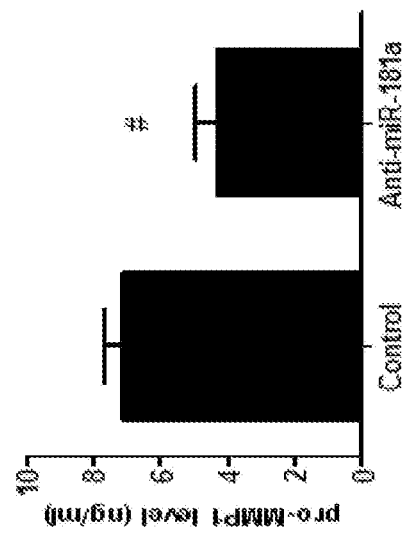

To provide further proof that nanopieces can deliver either antagomirs or replacement miR oligonucleotides to tumors, nanopieces with a molecular beacon or molecular beacon alone were injected into xenograft chondrosarcoma tumors. Molecular beacon is complementary to the mRNA sequence for the house keeping gene GAPDH and only fluoresces if the beacon hybridizes to GAPDH mRNA. GAPDH mRNA only exists inside the cell, so that flouresence indicates the beacon is intracellular. As shown in FIG. 14A, fluorescence is produced only if the beacon is injected into the tumor with nanopieces (RNT). When the experiment was repeated using an antagomir to miR-181a instead of the molecular beacon, expression of miR-181 was decreased in the tumor compared to control sequence (FIG. 14B) and MMP1 protein in the tumor decreased when measured by ELISA (FIG. 14C).

Figure 15:
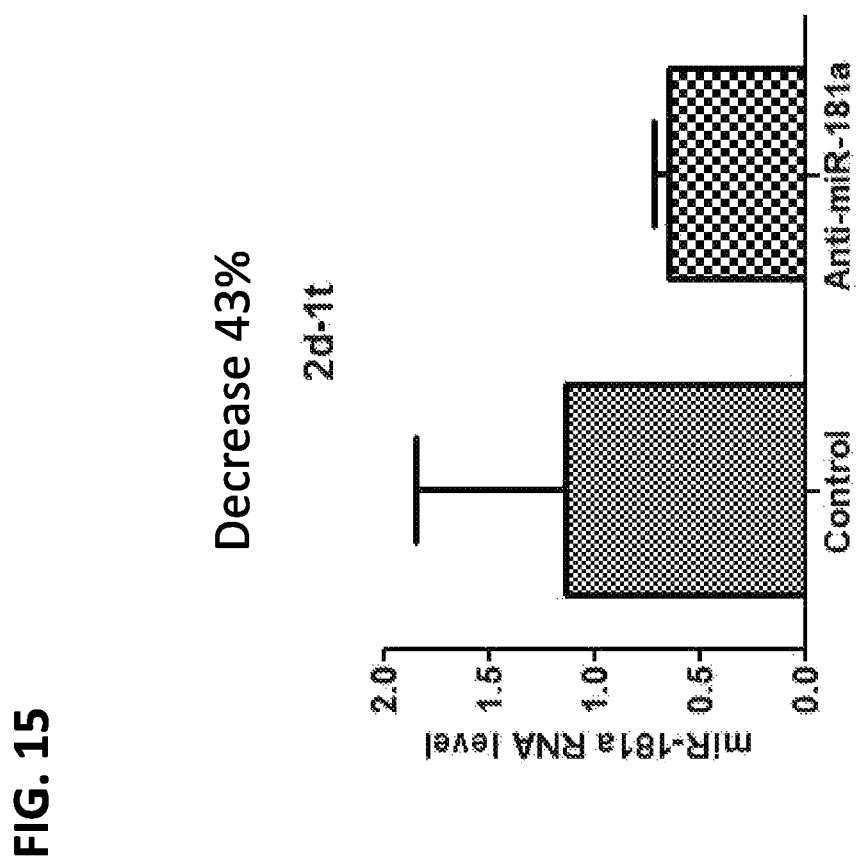
FIG. 15 depicts the in vivo effect of nanopiece plus anti-miR-181a delivered via tail vein injection on miR-181a expression 2 days after 1 injection compared to nanopiece plus control anti-miR.
Figure 16:
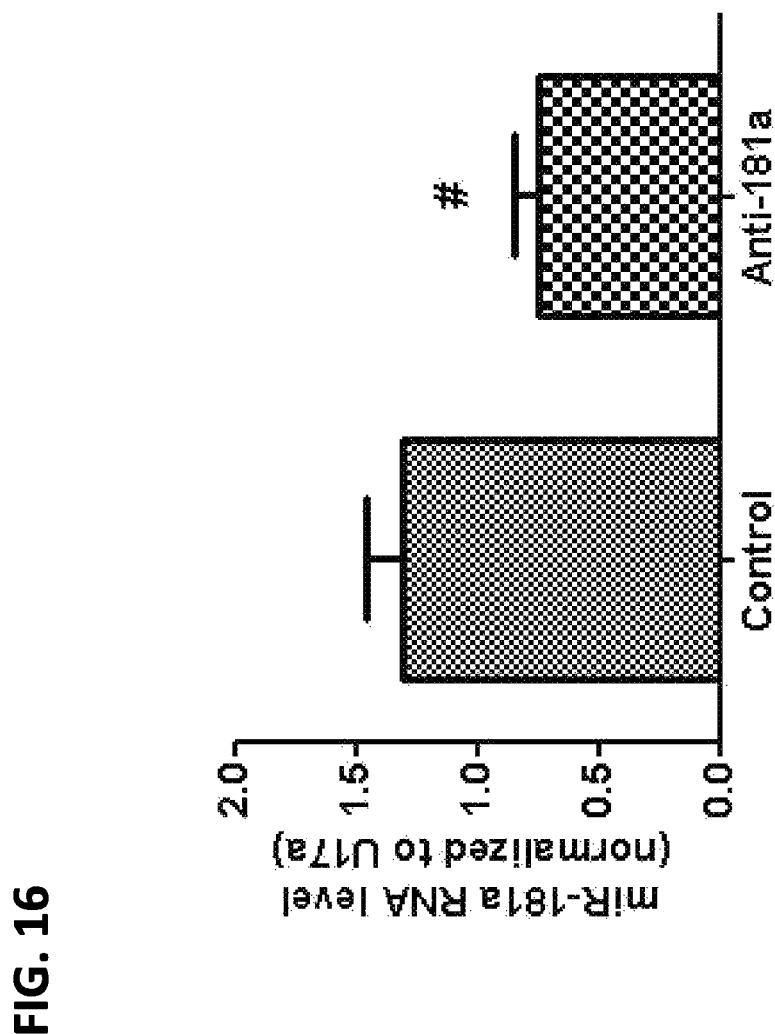
FIG. 16 is a graph depicting the results of a qRT-PCR analysis of mir-181a RNA expression levels after seven injections over three weeks under both control conditions as well as following treatment with anti-mir-181a, indicating sustained suppression of miR-181a. mir-181a RNA levels are normalized to expression of U17a (#, p<0.01).
Figure 17:
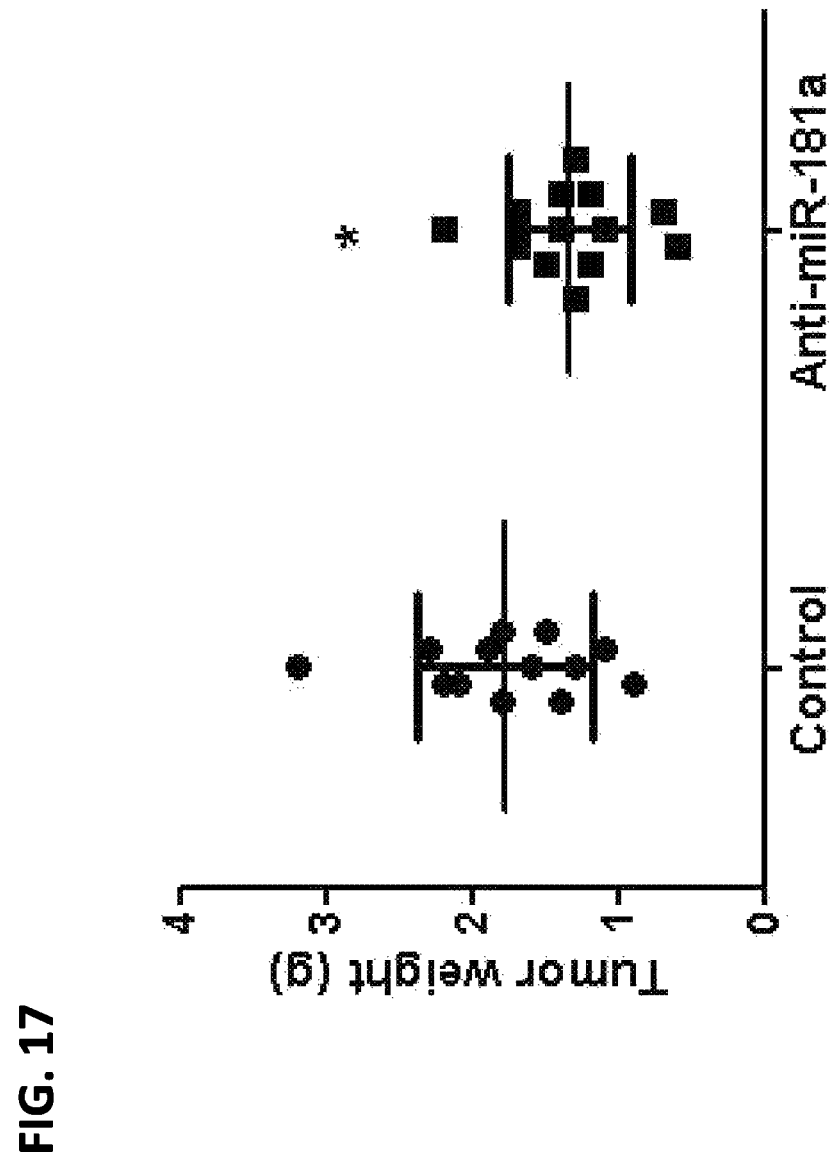
FIG. 17 is a graph depicting tumor weight in a mouse xenograft cancer model of chondrosarcoma following seven injections over three weeks under both control conditions as well as following treatment with anti-mir-181a (*, p<0.037).
Figure 18:
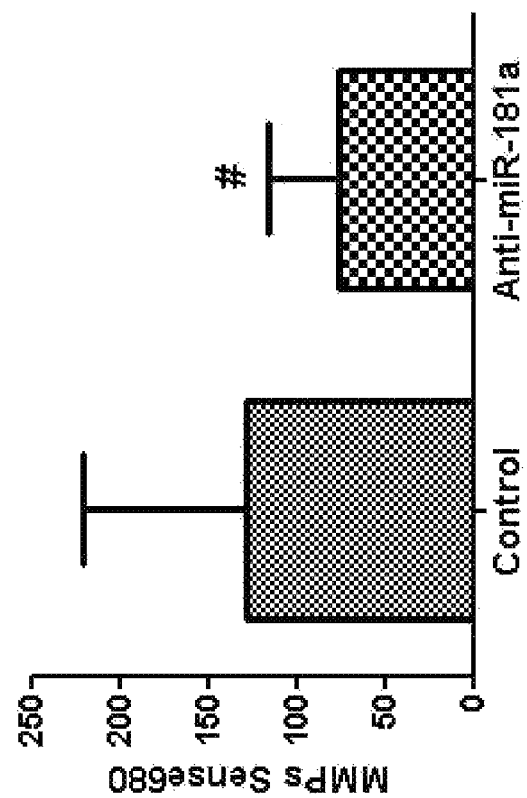
FIG. 18 is a graph depicting MMP probe content as measured by Fluorescence Molecular Tomography (FMT) in an in vivo mouse tumor model of chondrosarcoma following seven injections over three weeks under both control conditions as well as following treatment with anti-mir-181a (#, p<0.043).

To further demonstrate the feasibility of using a systemic treatment approach to altering microRNA expression using nanopieces for delivery, anti-miR181a in combination with nanopieces was delivered via tail vein injection into mice harboring xenograft tumors. After a single injection, this resulted in decreased miR-181 expression in the tumors (FIG. 15). After seven injections over a three week time span after establishment of xenograft tumors, miR-181a expression was again decreased (FIG. 16) tumor weight was decreased (FIG. 17), as was MMP activity as measured by FMT bioimaging (FIG. 18).

These results indicate that anti-miR-181a therapy is effective for reducing tumor burden in a mouse model of chondrosarcoma.

Taken together, the Examples demonstrate that analysis of specific chondrosarcoma tumors with microRNA array can be used to identify over and underexpressed microRNAs that are relevant biologic targets whose expression can be inhibited in the case of those overexpressed and restored in the case of those underexpressed via delivery of nucleotide sequences with nucleotide based nanopieces, resulting in inhibition of tumor progression.

Example 5

Treatment with anti-miR181a Enhances the Sensitivity of Chemotherapy in Chondrosarcoma Cells This Example shows the ability of anti-miR-181a treatment to enhance the sensitivity of chemotherapy in chondrosarcoma cells under both hypoxic and normoxic conditions.

Materials and Methods

Cell culture, transfection, and FMT assays were performed as described above.

Results

Figure 19:
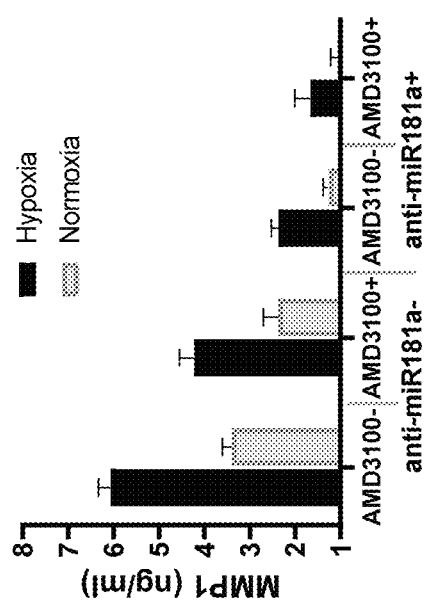
FIG. 19 is a graph showing MMP1 expression in chondrosarcoma cells following treatment with AMD3100 (plerixafor) and/or anti-miR-181a under both hypoxic and normoxic conditions.

AMD3100 (plerixafor) is an immunostimulant used to mobilize hematopoietic stem cells in cancer patients into the bloodstream and which also has been shown to reduce metastasis in mice (Sun et al., Mol Cancer Ther. 2013 July; 12(7):1163-70; Smith et al., Cancer Research, 2004, 64(23): 8604-8612). AMD3100 was administered alone and in combination with anti-miR-181a (80 nM under both normoxia and hypoxia (2% oxygen)). As shown in FIG. 19, co-administration of anti-miR-181a and AMD3100 synergistically decreased MMP1 expression under both normoxic and hypoxic conditions. Expression of metalloproteases, such as MMP1, can lead to cellular dissociation of cancer cells from underlying basal lamina and subsequent metastasis.

These results indicate that anti-miR-181a therapy can synergistically enhance the anti-tumor effects of AMD3100 when co-administered to chondrosarcoma cells under both hypoxic and normoxic conditions.

We claim:

1. A method for treating chondrosarcoma in an individual in need thereof, the method comprising identifying an individual diagnosed with chondrosarcoma or a predisposition thereto and administering to the individual a therapeutically effective amount of one or more chondrosarcoma-inhibiting microRNA (miR), wherein the miR comprises miR-34a, wherein said method results in decreased expression of vascular endothelial growth factor (VEGF), synovial sarcoma X-1 (SSX1), and tyrosine-protein kinase Met (Met), and wherein said method results in decreased chondrosarcoma cellular proliferation, invasion, or metastasis.

2. The method of claim 1, further comprising administering a chemotherapeutic to the individual.

3. The method of claim 2, wherein said chemotherapeutic is AMD3100.

4. The method of claim 1, further comprising administering an inhibitor of miR-181a.

5. The method of claim 1, wherein the individual is diagnosed with conventional chondrosarcoma, periosteal chondrosarcoma, mesenchymal chondrosarcoma, dedifferentiated chondrosarcoma, clear-cell chondrosarcoma, or extraskeletal myxoid chondrosarcoma.

6. The method of claim 1, wherein the method further comprises administration of one or more additional anti-cancer therapies to the individual.

7. The method of claim 6, wherein said one or more additional anti-cancer therapies is surgical ablation of the chondrosarcoma.

8. The method of claim 1, wherein the miR is administered by a nanopiece comprising a length of about 100 nm and width/diameter of about 20 nm.

9. The method of claim 1, wherein the chondrosarcoma-inhibiting microRNA (miR) is administered to a tumor bed of the chondrosarcoma in the individual following surgical resection of a tumor.

* * * * *